United States Patent [19]
Cochran et al.

[11] Patent Number: 6,136,318
[45] Date of Patent: Oct. 24, 2000

[54] RECOMBINANT FOWLPOX VIRUSES AND USES THEREOF

[76] Inventors: Mark D. Cochran, 4506 Horizon Dr., Carlsbad, Calif. 92008; David E. Junker, 6901 Galewood St., San Diego, Calif. 92120

[21] Appl. No.: 08/486,414

[22] Filed: Jun. 7, 1995

Related U.S. Application Data

[63] Continuation-in-part of application No. PCT/US94/02252, Feb. 28, 1994, which is a continuation of application No. 08/024,156, Feb. 26, 1993, abandoned.

[51] Int. Cl.⁷ .................. A61K 39/12; A61K 39/275; C12N 15/00; C12N 7/01
[52] U.S. Cl. .................. 424/199.1; 424/232.1; 435/235.1; 435/320.1; 435/69.1; 435/69.3; 935/65
[58] Field of Search .................. 435/235.1, 320.1, 435/69.1, 69.3, 172.3; 424/199.1, 93.2, 232.1; 935/65

[56] References Cited

U.S. PATENT DOCUMENTS

| | | |
|---|---|---|
| 5,093,258 | 3/1992 | Cohen et al. . |
| 5,174,993 | 12/1992 | Paoletti . |
| 5,180,675 | 1/1993 | Drillien et al. . |
| 5,182,210 | 1/1993 | Binns et al. . |
| 5,204,243 | 4/1993 | Paoletti . |
| 5,258,294 | 11/1993 | Boyle et al. . |
| 5,286,639 | 2/1994 | Yanagida et al. . |
| 5,310,671 | 5/1994 | Binns et al. . |
| 5,332,676 | 7/1994 | Binns et al. . |
| 5,368,855 | 11/1994 | Boyle et al. . |
| 5,369,025 | 11/1994 | Nazerian et al. . |
| 5,374,558 | 12/1994 | Binns et al. . |
| 5,387,519 | 2/1995 | Yanagida et al. . |
| 5,403,582 | 4/1995 | Nazerian et al. . |
| 5,443,831 | 8/1995 | Keeler et al. . |
| 5,505,941 | 4/1996 | Paoletti . |
| 5,514,375 | 5/1996 | Paoletti et al. . |
| 5,529,780 | 6/1996 | Paoletti et al. . |

FOREIGN PATENT DOCUMENTS

| | | |
|---|---|---|
| 404576 A3 | 12/1990 | European Pat. Off. . |
| 517292 A1 | 12/1992 | European Pat. Off. . |
| 520753 A1 | 12/1992 | European Pat. Off. . |
| 538496 A1 | 4/1993 | European Pat. Off. . |
| 314569 B1 | 3/1994 | European Pat. Off. . |
| 308220 B1 | 6/1994 | European Pat. Off. . |
| 284416 B1 | 2/1995 | European Pat. Off. . |
| 338807 B1 | 11/1995 | European Pat. Off. . |
| WO8802022 | 3/1988 | WIPO . |
| WO8903429 | 4/1989 | WIPO . |
| WO8903879 | 5/1989 | WIPO . |
| WO8907644 | 8/1989 | WIPO . |
| WO8912684 | 12/1989 | WIPO . |
| WO9004638 | 5/1990 | WIPO . |
| WO9012882 | 11/1990 | WIPO . |
| WO9112318 | 8/1991 | WIPO . |
| WO9102072 | 3/1992 | WIPO . |
| WO9203545 | 3/1992 | WIPO . |
| WO9222641 | 12/1992 | WIPO . |
| WO9303145 | 2/1993 | WIPO . |
| WO9314219 | 7/1993 | WIPO . |

OTHER PUBLICATIONS

Reeck et al. "Homology in Proteins and Nucleic Acids: A Terminology Muddle and Way out of it". Cell. vol. 50:667, 1987.

Boswell et al. "Sequence comparison and alignment: the measurement and interpretation of sequence similarity". Computational Molecular Biology. Arthur Lesk. eds. Oxford University Press. pp. 161–178, 1988.

Boursnell et al. "Insertion of the fusion Gene from Newcastle disease virus into a non–essential region in the terminal repeats of fowlpox virus and demonstration of protective immunity induced by the recombinant". Journal of General Virology. vol. 71:621, 1990.

Perkus et al. "Recombinant Vaccinia Virus: Immunization Against Multiple Pathogens". Science. vol. 229:981–984, 1985.

Leong et al. "Selective Induction of Immune Responses by Cytokines Coexpressed in Recombinant Fowlpox Virus". Journal of Virology. vol. 68(12):8125–8130, 1994.

Schnitzlein et al. "Genomic and antigenic characterization of avipoxviruses". Virus Research. vol. 10:65–76, 1988.

Klasing et al. "Avian Leukocytic Cytokine". Poultry Science. vol. 73(7):1035–1043, 1994.

Boursnell, Michael E.G. et al. (1992) "Avipoxvirus Vectors", Recomb. Poxviruses (1992), 269–83. Editors(s): Binns, Matthew, M.; Smith, Geoffrey L. Publisher: CRC, Boca Raton, Fla. Coden (Exhibit B).

Zantinge J.L. et al., "Analysis Of Fowlpox Virus DNA Replication And Mapping" Can. J. Microbiol., vol. 41, No. 4–5, 1995, pp. 378–387 (Exhibit C).

Mueller, H.K. et al. (1977) "Comparison of 5 Poxvirus Genomes By Analysis With Restriction Endonucleases Hin–D–III Bam–I and Eco–R–I", Virology 38:135–148.

Boyle, D.B. and Coupar B.E.H. (1986) "Identification and Cloning of the Fowlpox Virus Thymidine Kinase Gene Using Vaccinia Virus", Virology 67:1591–1600.

Boyle, D.B. et al. (1987) "Fowlpox Virus Thymidine Kinase Nucleotide Sequence and Relationships to Other Thymidine Kinases", Virology 156:355–365.

Schnitzlein, W.M. et al. (1988) "Genomic and Antigenic Characterization of Avipoxviruses", Virus Research 10:65–76.

(List continued on next page.)

*Primary Examiner*—Mary E. Mosher
*Assistant Examiner*—Ali R. Salimi
*Attorney, Agent, or Firm*—John P. White; Cooper & Dunham LLP

[57] ABSTRACT

This invention provides a recombinant fowlpox virus comprising a foreign DNA sequence inserted into the fowlpox virus genomic DNA, wherein the foreign DNA sequence is inserted within a 3.5 kB EcoRI fragment of the fowlpox virus genomic DNA and is capable of being expressed in a fowlpox virus infected host cell. The invention further provides homology vectors, vaccines and methods of immunization.

29 Claims, 11 Drawing Sheets

OTHER PUBLICATIONS

Boyle, D.B. and Coupar, B.E.H. (1988) "Construction of Recombinant Fowlpox Viruses as Vectors For Poultry Vaccines", Virus Research 10:343–356.

Tomley, F. et al. (1988) "Sequence Analysis of an 11.2 Kilobase Near–Terminal Bam–H–I Fragment of Fowlpox Virus", Journal of General Virology 69:1025–1040.

Binns, M.M. et al. (1988) "Comparison of A Conserved Region In Fowlpox Virus And Vaccinia Virus Genomes and the Translocation of the Fowlpox Virus Thymidine Kinase Gene", Journal of General Virology 69:1275–1284.

Taylor, J. And Paoletti, E. (1988) "Fowlpox Virus as a Vector in Non–Avian Species", Vaccine 6:466–468.

Campbell, J.I.A. et al. (1989) "Tandem Repeated Sequences With The Terminal Region of the Fowlpox Virus Genome", Journal of General Virology 70:145–154.

Taylor, J. et al. (1988) "Recombinant Fowlpox Virus Inducing Protective Immunity In Non–Avian Species", Vaccine 6:497–503.

Taylor, J. et al. (1988) "Protective Immunity Against Avian Influenza Induced By A Fowlpox Virus Recombinant", Vaccine 6:504–508.

Yanagida, N. et al. (Xxxx) "Protective Immunity Against Newcastle Disease Virus Induced By Fowlpox Virus Recombinants", Vaccines 90, Cold Spring Harbor Laboratory Press 85–89.

Spehner, D. et al. (1990) "Construction of Fowlpox Virus Vectors With Intergenic Insertions Expression of the Beta Galactosidase Gene and the Measles Virus Fusion Gene", Journal of Virology 64:1441–1450.

Kumar S. and Boyle, D.B. (1990) "Mapping of a Major Early–Late Gene of Fowlpox Virus", Virus Research 15:175–186.

Taylor, J. et al. (1990) "Newcastle Disease Virus Fusion Protein Expressed in a Fowlpox Virus Recombinant Confers Protection in Chickens", Journal of Virology 64:1441–1450.

Boursnell, M.E.G. et al. (1990) "Insertion of the Fusion Gene from Newcastle Disease Virus Into A Non–Essential Region In The Terminal Repeats of Fowlpox Virus and Demonstration of Protective Immunity Induced by the Recombinant", Virology 71:621–628.

Dhawale, S.S. and Nazerian K. (1990) "Construction of Recombinant Fowlpox Virus Expressing Bacterial Betagalactosidase in Chick Embryo Fibroblasts", Abstr Annu Meet Am Soc Microbiol 90:333.

Tripathy, D.N. and Wittek, R. (1990) "Regulation of Foreign Gene in Fowlpox Virus By a Vaccinia Virus Promoter", Avain Diseases 34:218–220.

Prideaux, C.T. et al. (1990) "Comparative Analysis of Vaccinia Virus Promoter Activity in Fowlpox and Vaccinia Virus Recombinants", Virus Res 16:43–58.

Tartaglia, J. et al. (1990) "Nucleotide Sequence Analysis of a 10.5 Kbp Hin–D–III Fragment of Fowlpox Virus Relatedness to the Central Portion of the Vaccinia Virus Hin–D–III D Region", Virology 71:1517–1524.

Kumar, S. and Boyle D.B. (1990) "Activity of a Fowlpox Virus Late Gene Promoter in Vaccinia and Fowlpox Virus Recombinants", Archives of Virology 112:139–148.

Boursnell, M.E.G. et al. (1990) "A Recombinant Fowlpox Virus Expressing the Hemagglutinin–Neuraminidase Gene To Newcastle Disease Virus NDV Protects Chickens Against Challenge By NDV", Virology 178:297–300.

Kumar, S. and Boyle D.B. (1990) "A Poxvirus Bidirectional Promoter Element With Early–Late and Late Functions", Virology 179:151–158.

Coupar, B.E.H. et al. (1990) "Restriction Endonuclease Mapping of the Fowlpox Virus Genome", Virology 179:159–167.

Wild, F. et al. (1990) "Fowlpox Virus Recombinant Encoding the Measles Virus Fusion Protein Protection of Mice Against Fatal Measles Encephalitis", Vaccine 8:441–442.

Ogawa, R. et al. (1990) "Recombinant Fowlpox Viruses Inducing Protective Immunity Against Newcastle Disease and Fowlpox Virus", Vaccine 8:486–490.

Edbauer, C. et al. (1990) "Protection of Chickens With a Recombinant Fowlpox Virus Expressing the Newcastle Disease Virus Hamagglutinin–Neuraminidase Gene", Virology 179:901–904.

Binns, M.M. et al. (1990) "Analysis of the Fowlpox Virus Genome Region Corresponding to the Vaccinia Virus D6 to A1 Region Location of and Variation in Non–Essential Genes in Poxviruses", Journal of General Virology 71:2873–2882.

Nazerian, K. And Dhawale, S. (1991) "Structural Analysis of Unstable Intermediate and Stable Forms of Recombinant Fowlpox Virus", Virology 72:2792–2795.

Tripathy, D.N. and Schnitzlein, W.M. (1991) "Expression of Avian Influenza Virus Hemmagglutinin By Recombinant Fowlpox Virus", Avain Diseases 35:186–191.

Taylor, J. et al. (1991) "Efficacy Studies on a Canarypox–Rabies Recombinant Virus", Vaccine 9:190–193.

Webster, R.G. et al. (1991) "Efficacy of Nucleoprotein and Hemagglutinin Antigens Expressed In Fowlpox Virus as Vaccine For Influenza in Chickens", Vaccine 9:303–308.

Beard, C.W. et al. (1991) "Protection of Chickens Against Highly Pathogenic Avian Influenza Virus H5N2 By Recombinant Fowlpox Viruses", Avian Disease 35:356–359.

Iritani, Y. et al. (1991) "Antibody Response To Newcastle Disease Virus NDV of Recombinant Fowlpox Virus Fpv Expressing a Hemagglutinin–Neuraminidase of Ndv into Chickens in the Presence of Antibody to NDV of FPV", Avain Diseases 35:659–661.

Bayliss, C.D. et al. (1991) "A Recombinant Fowlpox Virus That Expresses the Vp2 Antigen of Infectious Bursal Disease Virus Induces Protection Against Mortality Caused By the Virus", Archives of Virology 120:193–205.

Yanagida, N. et al. (1992) "Recombinant Fowlpox Viruses Expressing the Glycoprotein B Homolog and the Pp38 Gene Marek's Disease Virus", Journal of Virology 66:1402–1408.

Nazerian, K. et al. (1992) "Protection Against Marek's Disease By a Fowlpox Virus Recombinant Expressing the Glycoprotein B or Marek's Disease Virus", Journal of Virology 66:1409–1413.

Boyle D.B. (1992) "Quantitative Assessment of Poxvirus Promoters in Fowlpox and Vaccinia Virus Recombinants", Virus Genes 6:281–290.

Mockett, B. et al. (1992) "Comparison of the Locations of Homologous Fowlpox and Vaccinia Virus Genes Reveals Major Genome Reorganization", Journal of General Virology 73:2662–2668.

Calvert, J.G. et al. (1992) "Identification and Functional Analysis of the Fowlpox Virus Homolog of the Vaccinia Virus P37k Major Envelope Antigen Gene", Virology 191:783–792.

Beard, C.W. et al. (1992) "Effect of Route of Administration of the Efficacy of A Recombinant Fowlpox Virus Against H5n2 Avain Influenza", Avian Dis 36:1052–1055.

Baxby, D. and Paoletti, E. (1992) "Potential Use of Non–Replicating Vectors as Recombinant Vaccines", Vaccine 10:8–9.

Ogawa, R. et al. (1993) "Insertional Inactivation of a Fowlpox Virus Homologue of the Vaccinia Virus Fl2L Gene Inhibits the Release of Enveloped Virions", Journal of General Virology 74:55–64.

Calvert, J.G. et al. (1993) "Fowlpox Virus Recombinants Expressing the Envelope Glycoprotein of an Avian Reticuloendotheliosis Retrovirus Induce Neutralizing Antibodies and Reduce Viremia in Chickens", J Virol 67:3069–3076 (Ex. 4).

Heine, H.G. and Boyle, D.B. (1993) "Infectious Bursal Disease Virus Structural Protein Vp2 Expressed By a Fowlpox Virus Recombinant Confers Protection Against Disease in Chickens", Arch Virol 131:277–292 (Ex. 5).

Boyle, D.B. and Heine, H.G. (1993) "Recombinant Fowlpox Virus Vaccines For Poultry", Immun and Cell Biol 71:391–397 (Ex. 6).

Qingzhong, Y. et al. (1994) "Protection Against Turkey Rhinotracheitis Pneumovirus (TRTV) Induces By A Fowlpox Virus Recombinant Expressing the TRTV Fusion Glycoprotein (F)", Vaccine 12:569–573 (Ex. 7).

Konishi, E. et al. (1994) "Avipox Virus–Vectored Japanese Encephalitis Virus Vaccines: Use As Vaccine Candidates In Combination With Purified Subunit Immunogens", Vaccine 12:633–638 (Ex. 8).

Kent, S.J. et al. (1994) "Analysis of Cytotoxic T Lymphocyte Responses to SIV Proteins In SIV–Infected Macaques Using Antigen–Specific Stimulation With Recombinant Vaccinia and Fowl Poxviruses", AIDS Research and Human Retroviruses 10:551–560 (Ex. 9).

Yoshida, S. et al. (1994) "The Glycoprotein B Genes of Marek's Disease Virus Serotypes 2 and 3: Identification and Expression By Recombinant Fowlpox Viruses", Virology 200:484–493 (Ex. 10).

Parks, R.J. et al. (1994) "Studies of Fowlpox Virus Recombination in the Generation of Recombinant Vaccines", Virus Research 32:283–297 (Ex. 11).

Heine, H.G. et al. (1994) "Modificatin of Infectious Bursal Disease Virus Antigen VP2 For Cell Surface Location Fails to Enhance Immunogenicity", Virus Research 32:313–328 (Ex. 12).

McMillen, J.K. et al. (1993) "The Safe and Effective Use OF Fowlpox virus As A Vector For Poultry Vaccines", Brown, F. (Ed.). Developments in Biological Standardization, vol. 82. Recombinant Vectors In Vaccine Deveoplment; Symposium, Albany, NY, USA, May 23–26, 1993. viii+268p.S. Karger AG: Basel, Switzerland; New York, New York, USA (Ex. 13).

Paoletti, E. et al. (1993) "Highly Attenuated Poxvirus Vaccine Vectors: NYVAC and ALVAC", AIDS Research and Human Retroviruses 1994. S48. (Ex. 14).

Skinner, M.A. et al. (1994) "Deletion of Fowlpox Virus Homologues of Vaccinia Virus Genes Between the 3–Beta–Hydroxysteroid Dehydrogenase (A44L) and DNA Ligase (A540R) Genes", Jour Gen Virol 75:2495–2498 (Ex. 15).

Leong, K.H. et al. (1994) "Selective Induction of Immune Responses By Cytokines Coexpressed in Recombinant Fowlpox Virus", Jour Virol 68:8125–8130 (Ex. 16).

Wang, M. et al. (1995) "Active Immunotherapy of Cancer With A Nonreplicating Recombinant Fowlpox Virus Encoding A Model Tumor–Associated Antigen", Journal of Immunology 154:4685–4692 (Ex. 17).

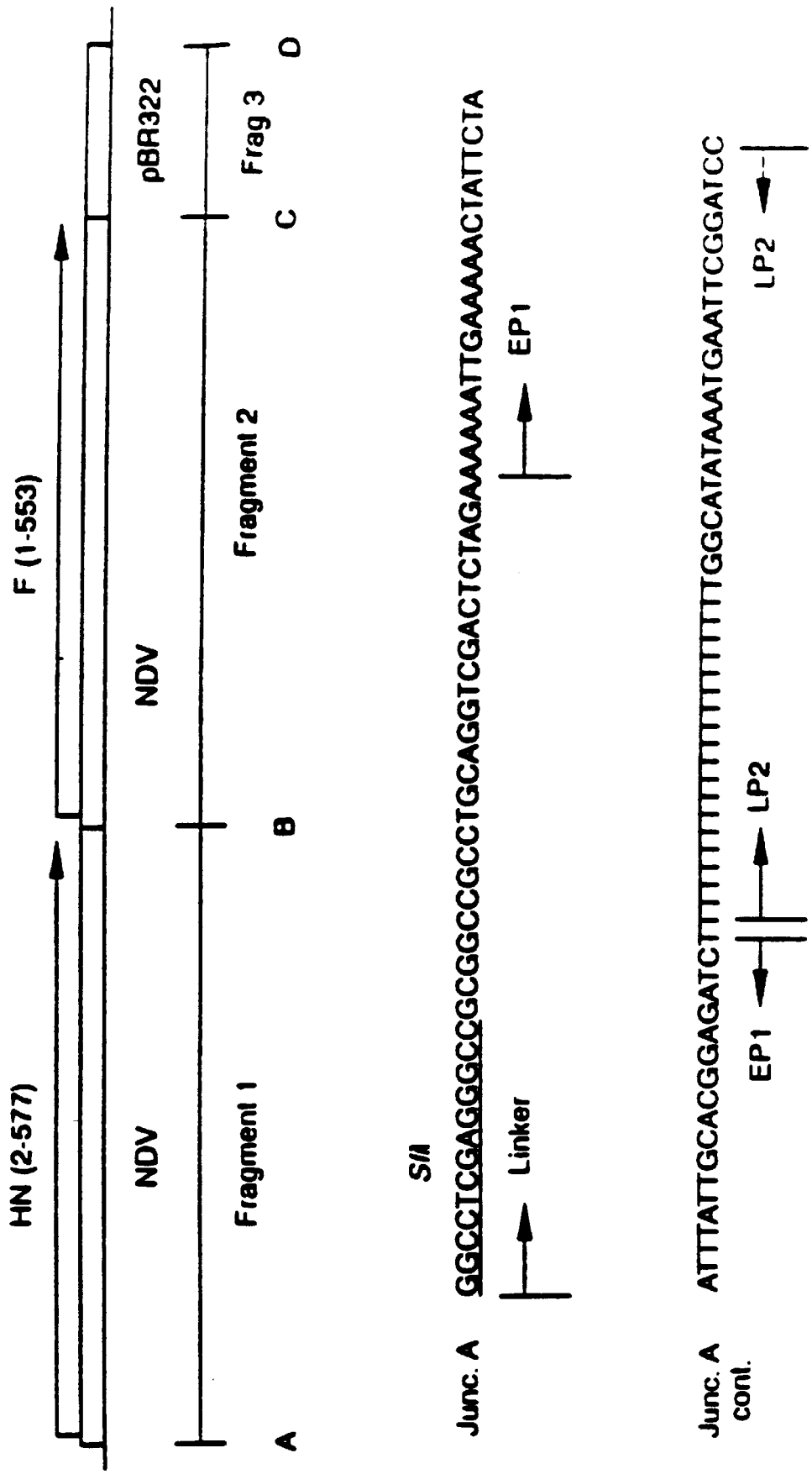

Figure 1C

Junc. C  AAAACCCCCCCCCCCTGCAGGCATCGTGGTGTCACGCGTCGTCGT
　　　　　　　　　　　　　　　　　Pstl
　　　　　　　　　Fragment 2  Fragment 3
　　　　　　　　　　NDV　　　　pBR322

Junc. D  ATAATTCTCTTACTGTCATGCCATCCGTAAGATGCTTTCTGTGTGACTGGTGAGTGATCCA
　　　　　　　　　　　　　　　　　[ScaI]
　　　　　　　　　　　　　　　　　　　　　　　　Fragment 3 ←→ Linker

| DNA | Origin | Sites | Size |
|---|---|---|---|
| Vector | pSP64 | EcoR I–EcoR I | ~2999 BP |
| Fragment 1 | FPV 2.8 kb EcoR I | EcoR I–SnaB I | ~1626 BP |
| Fragment 2 | chicken IFN | EcoR I†–Bgl II† | ~577 BP |
| Fragment 3 | pJF751 | Bam HI–Pvu II | ~3002 BP |
| Fragment 4 | FPV 2.8 kb EcoR I | SnaB I–EcoR I | ~1164 BP |

†Restriction sites introduced by PCR cloning

Figure 2A-1

751-07.D1; FPV-099, FPV-101

Junction A    GA TCC CCG GGC GAG CTC GAA TTC AAT ATT CAT CGC CGA TAG
                  Smal              EcoRI
                                         ← 2.8 kb FPV genomic fragment →
                                    pSP64

Junction B    TAC GGC GGC CGC CTG CAG GTC GAC TCT AGA TTT TTT TTT TTT TTG GCA TAT AAA
              [SnaBI] NotI                  SalI  XbaI
              ← 2.8 kb FPV                                                      LP2
                genomic
                fragment Junction B    TAG ATC TGT ATC CTA AAA TTG AAT TGT AAT TAT CGA TAA TAA AT
Continued        BglII                                  EP2

Junction B    GAA TTC GAT GGC TGT GCC TGC AAG CCC ACA GCA
Continued        EcoRI        → cIFN (aa 1-193)

SEQUENCE LISTING (1) GENERAL INFORMATION:

(iii) NUMBER OF SEQUENCES: 20

(2) INFORMATION FOR SEQ ID NO:1:

(i) SEQUENCE CHARACTERISTICS:
      (A) LENGTH: 28 base pairs
      (B) TYPE: nucleic acid
      (C) STRANDEDNESS: double
      (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:1:

CATAAGGCGG CCGCGGCCCT CGAGGCCA          28

(2) INFORMATION FOR SEQ ID NO:2:

(i) SEQUENCE CHARACTERISTICS:
        (A) LENGTH: 28 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:2:

```
CATAATGGCC TCGAGGGCCG CGGCCGCC                                              28
```

(2) INFORMATION FOR SEQ ID NO:3:

(i) SEQUENCE CHARACTERISTICS:
        (A) LENGTH: 1507 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: CDS
        (B) LOCATION: 260..1411

(xi) SEQUENCE DESCRIPTION: SEQ ID NO:3:

```
CTACTTCATA AAAGTTTAA ACCTTCCGAA AGATTTTTGG ATAAAAGTAG AGAACTCGCA           60

TTGCGATTAT GCTCTAGGAC AATCCTGTAA AGTGTCTCGA TCTTAGCATA TAGATAAATG          120

TTTGAACTAA TATCCTAAAG CCTGTATGTA ACAGTTGGTG CCTATTGAAA GATACTGATT          180

ATCAAGGAGA AGAATAATAT AAATCGTAAA AATAATACTT ATTATATAAT ATAATGTATA          240

ATAATATACA AAAACAGCC ATG ATA CGT ATT ATA ATA TTA TCG TTA TTA TTT          292
                     Met Ile Arg Ile Ile Ile Leu Ser Leu Leu Phe
                      1               5                  10

ATT AAC GTA ACA ACA GAT AGT CAA GAA TCT TCA AAA AAT ATA CAA AAT           340
Ile Asn Val Thr Thr Asp Ser Gln Glu Ser Ser Lys Asn Ile Gln Asn
           15                   20                   25

GTA TTG CAC GTT ACA GAA TAT AGT AGA ACT GGT GTA ACA GCT TGC TCG           388
Val Leu His Val Thr Glu Tyr Ser Arg Thr Gly Val Thr Ala Cys Ser
       30                  35                  40

TTA CAT TGT TTT GAT CGT TCC AAA GGT TTA GAT CAA CCA AAA ACA TTT           436
Leu His Cys Phe Asp Arg Ser Lys Gly Leu Asp Gln Pro Lys Thr Phe
   45                  50                  55

ATC CTG CCT GGT AAA TAT AGC AAT AAC AGT ATA AAA CTA GAA GTA GCT           484
Ile Leu Pro Gly Lys Tyr Ser Asn Asn Ser Ile Lys Leu Glu Val Ala
60                  65                  70                  75

ATT GAT ACA TAT AAA AAA GAT AGC GAC TTC AGT TAT TCT CAC CCA TGT           532
Ile Asp Thr Tyr Lys Lys Asp Ser Asp Phe Ser Tyr Ser His Pro Cys
               80                  85                  90

CAA ATA TTC CAG TTC TGT GTG TCT GGT AAT TTT AGT GGT AAA CGG TTC           580
Gln Ile Phe Gln Phe Cys Val Ser Gly Asn Phe Ser Gly Lys Arg Phe
           95                  100                 105

GAT CAT TAT CTA TAT GGG TAT ACA ATT TCC GGA TTT ATA GAT ATT GCT           628
Asp His Tyr Leu Tyr Gly Tyr Thr Ile Ser Gly Phe Ile Asp Ile Ala
```

-continued

```
               110                     115                     120
CCA AAA TAT TAT AGC GGT ATG TCT ATA AGT ACT ATT ACT GTT ATG CCA        676
Pro Lys Tyr Tyr Ser Gly Met Ser Ile Ser Thr Ile Thr Val Met Pro
    125                     130                     135

TTA CAA GAA GGA TCA TTA AAG CAT GAT GAT GCC GAT GAC TAT GAC TAC        724
Leu Gln Glu Gly Ser Leu Lys His Asp Asp Ala Asp Asp Tyr Asp Tyr
140                     145                     150                     155

GAT GAT GAT TGT GTT CCT TAT AAA GAA ACC CAG CCT CGA CAT ATG CCA        772
Asp Asp Asp Cys Val Pro Tyr Lys Glu Thr Gln Pro Arg His Met Pro
                    160                     165                     170

GAA TCG GTA ATA AAA GAA GGA TGT AAA CCC ATT CCA CTA CCA AGG TAT        820
Glu Ser Val Ile Lys Glu Gly Cys Lys Pro Ile Pro Leu Pro Arg Tyr
            175                     180                     185

GAT GAA AAT GAC GAT CCT ACT TGT ATT ATG TAT TGG GAT CAC TCG TGG        868
Asp Glu Asn Asp Asp Pro Thr Cys Ile Met Tyr Trp Asp His Ser Trp
        190                     195                     200

GAT AAT TAC TGT AAT GTT GGA TTT TTT AAT TCT CTA CAG AGT GAT CAC        916
Asp Asn Tyr Cys Asn Val Gly Phe Phe Asn Ser Leu Gln Ser Asp His
    205                     210                     215

AAT CCT CTG GTT TTT CCG TTA ACA AGT TAT TCT GAT ATA AAC AAT GCA        964
Asn Pro Leu Val Phe Pro Leu Thr Ser Tyr Ser Asp Ile Asn Asn Ala
220                     225                     230                     235

TTT CAT GCT TTT CAA TCA TCT TAT TGT AGA TCA CTA GGC TTT AAC CAA       1012
Phe His Ala Phe Gln Ser Ser Tyr Cys Arg Ser Leu Gly Phe Asn Gln
                    240                     245                     250

TCA TAC AGT GTA TGC GTA TCT ATA GGT GAT ACA CCA TTT GAG GTT ACG       1060
Ser Tyr Ser Val Cys Val Ser Ile Gly Asp Thr Pro Phe Glu Val Thr
            255                     260                     265

TAT CAT AGT TAT GAA AGT GTT ACT GTT GAT CAG TTA TTA CAA GAA ATT       1108
Tyr His Ser Tyr Glu Ser Val Thr Val Asp Gln Leu Leu Gln Glu Ile
        270                     275                     280

AAA ACA CTA TAT GGA GAA GAT GCT GTA TAT GGA TTA CCG TTT AGA AAT       1156
Lys Thr Leu Tyr Gly Glu Asp Ala Val Tyr Gly Leu Pro Phe Arg Asn
    285                     290                     295

ATA ACT ATA AGG GCG CGT ACA CGG ATT CAA AGT TTA CCT CTT ACT AAC       1204
Ile Thr Ile Arg Ala Arg Thr Arg Ile Gln Ser Leu Pro Leu Thr Asn
300                     305                     310                     315

AAT ACC TGT ATC CCT AAA CAA GAC GAT GCT GAT GAT GTT GAC GAT GCT       1252
Asn Thr Cys Ile Pro Lys Gln Asp Asp Ala Asp Asp Val Asp Asp Ala
                    320                     325                     330

GAT GAT GTT GAC GAT GCT GAT GAT GCT GAC GAT GAT GAT GAT TAC GAG       1300
Asp Asp Val Asp Asp Ala Asp Asp Ala Asp Asp Asp Asp Asp Tyr Glu
            335                     340                     345

TTA TAT GTA GAA ACT ACA CCA AGA GTG CCA ACA GCG AGA AAA AAA CCC       1348
Leu Tyr Val Glu Thr Thr Pro Arg Val Pro Thr Ala Arg Lys Lys Pro
        350                     355                     360

GTT ACA GAA GAA TAT AAT GAT ATA TTT AGT AGT TTT GAT AAT TTT GAC       1396
Val Thr Glu Glu Tyr Asn Asp Ile Phe Ser Ser Phe Asp Asn Phe Asp
    365                     370                     375

ATG AAA AAG AAA TAAGACATAT TTATTAAAT CAAAAAGTCT GTCGAACTTT            1448
Met Lys Lys Lys
380

TAGTGTTTAA CCTATATCGA TTTATGATTT TTCCATGATG ATCCAGGCTA TGACTGACT      1507
```

(2) INFORMATION FOR SEQ ID NO:4:

(i) SEQUENCE CHARACTERISTICS:
        (A) LENGTH: 383 amino acids
        (B) TYPE: amino acid
        (D) TOPOLOGY: linear (ii) MOLECULE TYPE: protein (xi) SEQUENCE DESCRIPTION: SEQ ID NO:4:

```
Met Ile Arg Ile Ile Ile Leu Ser Leu Leu Phe Ile Asn Val Thr Thr
  1               5                  10                  15

Asp Ser Gln Glu Ser Ser Lys Asn Ile Gln Asn Val Leu His Val Thr
             20                  25                  30

Glu Tyr Ser Arg Thr Gly Val Thr Ala Cys Ser Leu His Cys Phe Asp
         35                  40                  45

Arg Ser Lys Gly Leu Asp Gln Pro Lys Thr Phe Ile Leu Pro Gly Lys
 50                  55                  60

Tyr Ser Asn Asn Ser Ile Lys Leu Glu Val Ala Ile Asp Thr Tyr Lys
 65                  70                  75                  80

Lys Asp Ser Asp Phe Ser Tyr Ser His Pro Cys Gln Ile Phe Gln Phe
                 85                  90                  95

Cys Val Ser Gly Asn Phe Ser Gly Lys Arg Phe Asp His Tyr Leu Tyr
            100                 105                 110

Gly Tyr Thr Ile Ser Gly Phe Ile Asp Ile Ala Pro Lys Tyr Tyr Ser
        115                 120                 125

Gly Met Ser Ile Ser Thr Ile Thr Val Met Pro Leu Gln Glu Gly Ser
130                 135                 140

Leu Lys His Asp Asp Ala Asp Asp Tyr Asp Tyr Asp Asp Asp Cys Val
145                 150                 155                 160

Pro Tyr Lys Glu Thr Gln Pro Arg His Met Pro Glu Ser Val Ile Lys
                165                 170                 175

Glu Gly Cys Lys Pro Ile Pro Leu Pro Arg Tyr Asp Glu Asn Asp Asp
            180                 185                 190

Pro Thr Cys Ile Met Tyr Trp Asp His Ser Trp Asp Asn Tyr Cys Asn
        195                 200                 205

Val Gly Phe Phe Asn Ser Leu Gln Ser Asp His Asn Pro Leu Val Phe
210                 215                 220

Pro Leu Thr Ser Tyr Ser Asp Ile Asn Asn Ala Phe His Ala Phe Gln
225                 230                 235                 240

Ser Ser Tyr Cys Arg Ser Leu Gly Phe Asn Gln Ser Tyr Ser Val Cys
                245                 250                 255

Val Ser Ile Gly Asp Thr Pro Phe Glu Val Thr Tyr His Ser Tyr Glu
            260                 265                 270

Ser Val Thr Val Asp Gln Leu Leu Gln Glu Ile Lys Thr Leu Tyr Gly
        275                 280                 285

Glu Asp Ala Val Tyr Gly Leu Pro Phe Arg Asn Ile Thr Ile Arg Ala
290                 295                 300

Arg Thr Arg Ile Gln Ser Leu Pro Leu Thr Asn Asn Thr Cys Ile Pro
305                 310                 315                 320

Lys Gln Asp Asp Ala Asp Asp Val Asp Ala Asp Asp Val Asp Asp
                325                 330                 335

Ala Asp Ala Asp Asp Asp Tyr Glu Leu Tyr Val Glu Thr
            340                 345                 350

Thr Pro Arg Val Pro Thr Ala Arg Lys Lys Pro Val Thr Glu Glu Tyr
        355                 360                 365

Asn Asp Ile Phe Ser Ser Phe Asp Asn Phe Asp Met Lys Lys Lys
370                 375                 380
```

(2) INFORMATION FOR SEQ ID NO:5:

(i) SEQUENCE CHARACTERISTICS:
        (A) LENGTH: 2849 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: CDS
        (B) LOCATION: 300..1568

(ix) FEATURE:
        (A) NAME/KEY: CDS
        (B) LOCATION: complement (1685..2848)

(xi) SEQUENCE DESCRIPTION: SEQ ID NO:5:

```
AAGCCAGTTT GAATTCAATA TTCATCGCCG ATAGTTGGTA GAAATACTAT TCATGAAATT        60

TACCTTCTTC CGTGGCTTAA AAACTTATTG TATGTACCAT TCATTATAAG ATCTGATACT       120

ATCGGCATCT TCTATTTTCC GAGTTTTTTA CATCTGGTTA CTAGTATCCA TGTTCGTCTA       180

ATAAGAGGGA AGGAATATAT CTATCTACAT AAACATCATA AGGTTCTTTG ATAGATTTAT       240

ATCGCTAATA AAATATAAAT AATAATTAAA GATTTTATGA TATATCGAGC TTTGCAAAA        299

ATG TCT GTT GAT TGG CGT ACA GAA ATC TAT TCG GGT GAT ATA TCC CTA         347
Met Ser Val Asp Trp Arg Thr Glu Ile Tyr Ser Gly Asp Ile Ser Leu
  1               5                  10                  15

GTA GAA AAA CTT ATA AAG AAT AAA GGT AAT TGC ATC AAT ATA TCT GTA         395
Val Glu Lys Leu Ile Lys Asn Lys Gly Asn Cys Ile Asn Ile Ser Val
             20                  25                  30

GAG GAA ACA ACA ACT CCG TTA ATA GAC GCT ATA AGA ACC GGA AAT GCC         443
Glu Glu Thr Thr Thr Pro Leu Ile Asp Ala Ile Arg Thr Gly Asn Ala
         35                  40                  45

AAA ATA GTA GAA CTA TTT ATC AAG CAC GGA GCG CAA GTT AAT CAT GTA         491
Lys Ile Val Glu Leu Phe Ile Lys His Gly Ala Gln Val Asn His Val
     50                  55                  60

AAT ACT AAA ATT CCT AAT CCC TTG TTA ACA GCT ATC AAA ATA GGA TCA         539
Asn Thr Lys Ile Pro Asn Pro Leu Leu Thr Ala Ile Lys Ile Gly Ser
 65                  70                  75                  80

CAC GAT ATA GTA AAA CTG CTG TTG ATT AAC GGA GTT GAT ACT TCT ATT         587
His Asp Ile Val Lys Leu Leu Leu Ile Asn Gly Val Asp Thr Ser Ile
                 85                  90                  95

TTG CCA GTC CCC TGC ATA AAT AAA GAA ATG ATA AAA ACT ATA TTA GAT         635
Leu Pro Val Pro Cys Ile Asn Lys Glu Met Ile Lys Thr Ile Leu Asp
            100                 105                 110

AGT GGT GTG AAA GTA AAC ACA AAA AAT GCT AAA TCT AAA ACT TTC TTG         683
Ser Gly Val Lys Val Asn Thr Lys Asn Ala Lys Ser Lys Thr Phe Leu
        115                 120                 125

CAT TAC GCG ATT AAG AAT AAT GAC TTA GAG GTT ATC AAA ATG CTT TTT         731
His Tyr Ala Ile Lys Asn Asn Asp Leu Glu Val Ile Lys Met Leu Phe
    130                 135                 140

GAG TAT GGA GCT GAT GTT AAT ATA AAA GAT GAT AAC ATA TGT TAT TCT         779
Glu Tyr Gly Ala Asp Val Asn Ile Lys Asp Asp Asn Ile Cys Tyr Ser
145                 150                 155                 160

ATA CAC ATA GCT ACT AGG AGT AAT TCA TAT GAA ATC ATA AAA TTA CTA         827
Ile His Ile Ala Thr Arg Ser Asn Ser Tyr Glu Ile Ile Lys Leu Leu
                165                 170                 175

TTA GAA AAA GGT GCT TAT GCA AAC GTA AAA GAC AAT TAT GGT AAT TCT         875
Leu Glu Lys Gly Ala Tyr Ala Asn Val Lys Asp Asn Tyr Gly Asn Ser
```

```
                180                 185                 190
CCG TTA CAT AAC GCG GCT AAA TAT GGC GAT TAT GCT TGT ATT AAA TTA      923
Pro Leu His Asn Ala Ala Lys Tyr Gly Asp Tyr Ala Cys Ile Lys Leu
        195                 200                 205

GTT TTA GAC CAT ACT AAT AAC ATA AGC AAT AAG TGC AAC AAC GGT GTT      971
Val Leu Asp His Thr Asn Asn Ile Ser Asn Lys Cys Asn Asn Gly Val
        210                 215                 220

ACA CCG TTA CAT AAC GCT ATA CTA TAT AAT AGA TCT GCC GTA GAA TTA     1019
Thr Pro Leu His Asn Ala Ile Leu Tyr Asn Arg Ser Ala Val Glu Leu
225                 230                 235                 240

CTG ATT AAC AAT CGA TCT ATT AAT GAT ACG GAT GTA GAC GGA TAT ACT     1067
Leu Ile Asn Asn Arg Ser Ile Asn Asp Thr Asp Val Asp Gly Tyr Thr
                245                 250                 255

CCA CTA CAT TAT GCT TTG CAA CCT CCG TGT AGT ATA GAT ATT ATA GAT     1115
Pro Leu His Tyr Ala Leu Gln Pro Pro Cys Ser Ile Asp Ile Ile Asp
                260                 265                 270

ATA CTA CTA TAT AAC AAC GCC GAT ATA TCT ATA AAA GAT AAT AAC GGA     1163
Ile Leu Leu Tyr Asn Asn Ala Asp Ile Ser Ile Lys Asp Asn Asn Gly
            275                 280                 285

CGC AAT CCT ATC GAT ACG GCG TTT AAG TAT ATT AAC AGA GAT AGC GTT     1211
Arg Asn Pro Ile Asp Thr Ala Phe Lys Tyr Ile Asn Arg Asp Ser Val
        290                 295                 300

ATA AAA GAA CTT CTC CGA AAC GCC GTG TTA ATT AAC GAG GTC GGT AAA     1259
Ile Lys Glu Leu Leu Arg Asn Ala Val Leu Ile Asn Glu Val Gly Lys
305                 310                 315                 320

TTA AAA GAT ACT ACT ATC TTA GAA CAC AAA GAA ATA AAA GAC AAT ACC     1307
Leu Lys Asp Thr Thr Ile Leu Glu His Lys Glu Ile Lys Asp Asn Thr
                325                 330                 335

GTG TTT TCA AAC TTT GTG TAC GAA TGT AAT GAA GAA ATT AAA AAA ATG     1355
Val Phe Ser Asn Phe Val Tyr Glu Cys Asn Glu Glu Ile Lys Lys Met
                340                 345                 350

AAG AAA ACT AAA TGT GTC GGT GAC TAT AGT ATG TTT GAC GTA TAC ATG     1403
Lys Lys Thr Lys Cys Val Gly Asp Tyr Ser Met Phe Asp Val Tyr Met
            355                 360                 365

ATA AGG TAT AAA CAC AAA TAT GAC GGT AAT AAG GAT AGT ATT AAA GAC     1451
Ile Arg Tyr Lys His Lys Tyr Asp Gly Asn Lys Asp Ser Ile Lys Asp
        370                 375                 380

TAT TTG CGT TGT CTT GAT GAT AAT AGT ACT CGT ATG TTA AAA ACT ATA     1499
Tyr Leu Arg Cys Leu Asp Asp Asn Ser Thr Arg Met Leu Lys Thr Ile
385                 390                 395                 400

GAT ATT AAT GAA TTT CCT ATA TAT TCT ATG TAT CTC GTA AGA TGC CTA     1547
Asp Ile Asn Glu Phe Pro Ile Tyr Ser Met Tyr Leu Val Arg Cys Leu
                405                 410                 415

TAT GAT ATG GTA ATA TAT TAAAAGAAAT GGGCTCTTGC ATACATAATC            1595
Tyr Asp Met Val Ile Tyr
                420

GGTATAAAAA ATAACGAAAT TATTAGCGGT TACATATCTT ACGGCGGCCG CGGCCCTCGA   1655

GGCCAGTAGC TCAGTATTTC CTATAAACTC TAATATTGAG AGTTTGATAT CCGGAGAAGT   1715

TTAGACCAAC CGCTAGAATC TAATATTTCA TCTAATTTTG ATCTACTTTT TTCTAATATT   1775

TTATGTCTAT TACTGGCTAA GGATATGGAA GTTTAAGAC GATCTCCGTA ATTATAGAAA    1835

TAGTAAGTAT TAATTTCCTT TATTATAGGA TTATTTACTA AGTGATGTAA CAGGTTCATG   1895

TTTTTACTAA TAACGAATAT ATCTAAAGAG TAAAACATAT TAATACGAAT TTTAGATATA   1955

TCTTTTAGTT CTTCCTTACA ACTCAACCAA ATACTTTTAA ACGTATCATC GCTTTGAATA   2015

ATTTCTCTCA AGGGGTTTAC TTCACTTCTG ATATCGTGAC GTATAAAATC TTGTATACAT   2075

ATATGTGCTA TGATATATCT AAAAGAAAAC ATATTACTGT TAAGGCTCTT ATCGATGACC   2135
```

```
CTACTATCTC TAAGTTCAGC ACCATAATGT AATAATATAT TTACTATACC ATGATATTCT    2195

AATGCTATTA ATAAAGGATA TTGATTCCTT ATGTTAATAG CATTTACATC CGCTCCGTTA    2255

TCTAATAACA TTTTTATAAC TTCTGGTTTA CAATTCTTTT TACACGCATA ATGCAACGGA    2315

GTAGATAAGT ATTTGTTTTT AGAATTAACA TTAGCTCCTC TATCTATGAG CGTTTTTACA    2375

CTCATATACG GATTTGTTCC ATATAAGGCA AAATGTAAAA CCGTTCCTAT CTTCTGCGAT    2435

AACGCTTCTA TATCGGCCCC GTAATCTAAA AGAGTGTTTA TGATAACTAC ATTGTTTCTT    2495

ACAGCGGCAT AATGAATAGG CGTCTTGTCA CAATAATCTC TAGCATTTAC GTTCGCTCCC    2555

AATTCTAACA ACGTTATAAC TGTATCTTTA TATCTATCTA GAGTAGAGGC TTGATGTAAT    2615

GGAGTGATAT ACAGACTATC AGCGGCGTTA ACATCTGCAC CCCGCATTAT TAAAGTTCTA    2675

ATGTTTTCTG TATCGTATCC ATTCTTAGCC ATGAGATACA GAGGAGTTTC TCCTTTAATG    2735

TTTTTAGCGT TAACATCTAT TCCTCTTTCC AATAACTTGG GTACTAGTCT ACTTAACGAA    2795

GGTGCTTGTA CCGTGTAATG CAAAGGAGTA TTCTTATAAA CATCTATAGA ATTC          2849
```

(2) INFORMATION FOR SEQ ID NO:6:

(i) SEQUENCE CHARACTERISTICS:
        (A) LENGTH: 422 amino acids
        (B) TYPE: amino acid
        (D) TOPOLOGY: linear (ii) MOLECULE TYPE: protein (xi) SEQUENCE DESCRIPTION: SEQ ID NO:6:

```
Met Ser Val Asp Trp Arg Thr Glu Ile Tyr Ser Gly Asp Ile Ser Leu
 1               5                  10                  15

Val Glu Lys Leu Ile Lys Asn Lys Gly Asn Cys Ile Asn Ile Ser Val
            20                  25                  30

Glu Glu Thr Thr Thr Pro Leu Ile Asp Ala Ile Arg Thr Gly Asn Ala
        35                  40                  45

Lys Ile Val Glu Leu Phe Ile Lys His Gly Ala Gln Val Asn His Val
    50                  55                  60

Asn Thr Lys Ile Pro Asn Pro Leu Leu Thr Ala Ile Lys Ile Gly Ser
65                  70                  75                  80

His Asp Ile Val Lys Leu Leu Ile Asn Gly Val Asp Thr Ser Ile
                85                  90                  95

Leu Pro Val Pro Cys Ile Asn Lys Glu Met Ile Lys Thr Ile Leu Asp
            100                 105                 110

Ser Gly Val Lys Val Asn Thr Lys Asn Ala Lys Ser Lys Thr Phe Leu
        115                 120                 125

His Tyr Ala Ile Lys Asn Asn Asp Leu Glu Val Ile Lys Met Leu Phe
    130                 135                 140

Glu Tyr Gly Ala Asp Val Asn Ile Lys Asp Asp Asn Ile Cys Tyr Ser
145                 150                 155                 160

Ile His Ile Ala Thr Arg Ser Asn Ser Tyr Glu Ile Ile Lys Leu Leu
                165                 170                 175

Leu Glu Lys Gly Ala Tyr Ala Asn Val Lys Asp Asn Tyr Gly Asn Ser
            180                 185                 190

Pro Leu His Asn Ala Ala Lys Tyr Gly Asp Tyr Ala Cys Ile Lys Leu
        195                 200                 205

Val Leu Asp His Thr Asn Asn Ile Ser Asn Lys Cys Asn Asn Gly Val
    210                 215                 220
```

```
Thr Pro Leu His Asn Ala Ile Leu Tyr Asn Arg Ser Ala Val Glu Leu
225                 230                 235                 240

Leu Ile Asn Asn Arg Ser Ile Asn Asp Thr Asp Val Asp Gly Tyr Thr
            245                 250                 255

Pro Leu His Tyr Ala Leu Gln Pro Pro Cys Ser Ile Asp Ile Ile Asp
            260                 265                 270

Ile Leu Leu Tyr Asn Asn Ala Asp Ile Ser Ile Lys Asp Asn Asn Gly
            275                 280                 285

Arg Asn Pro Ile Asp Thr Ala Phe Lys Tyr Ile Asn Arg Asp Ser Val
290                 295                 300

Ile Lys Glu Leu Leu Arg Asn Ala Val Leu Ile Asn Glu Val Gly Lys
305                 310                 315                 320

Leu Lys Asp Thr Thr Ile Leu Glu His Lys Glu Ile Lys Asp Asn Thr
            325                 330                 335

Val Phe Ser Asn Phe Val Tyr Glu Cys Asn Glu Glu Ile Lys Lys Met
            340                 345                 350

Lys Lys Thr Lys Cys Val Gly Asp Tyr Ser Met Phe Asp Val Tyr Met
            355                 360                 365

Ile Arg Tyr Lys His Lys Tyr Asp Gly Asn Lys Asp Ser Ile Lys Asp
370                 375                 380

Tyr Leu Arg Cys Leu Asp Asp Asn Ser Thr Arg Met Leu Lys Thr Ile
385                 390                 395                 400

Asp Ile Asn Glu Phe Pro Ile Tyr Ser Met Tyr Leu Val Arg Cys Leu
            405                 410                 415

Tyr Asp Met Val Ile Tyr
            420
```

(2) INFORMATION FOR SEQ ID NO:7:

(i) SEQUENCE CHARACTERISTICS:
        (A) LENGTH: 387 amino acids
        (B) TYPE: amino acid
        (D) TOPOLOGY: linear (ii) MOLECULE TYPE: protein (xi) SEQUENCE DESCRIPTION: SEQ ID NO:7:

```
Asn Ser Ile Asp Val Tyr Lys Asn Thr Pro Leu His Tyr Thr Val Gln
1                   5                   10                  15

Ala Pro Ser Leu Ser Arg Leu Val Pro Lys Leu Leu Glu Arg Gly Ile
            20                  25                  30

Asp Val Asn Ala Lys Asn Ile Lys Gly Glu Thr Pro Leu Tyr Leu Met
            35                  40                  45

Ala Lys Asn Gly Tyr Asp Thr Glu Asn Ile Arg Thr Leu Ile Met Arg
    50                  55                  60

Gly Ala Asp Val Asn Ala Ala Asp Ser Leu Tyr Ile Thr Pro Leu His
65                  70                  75                  80

Gln Ala Ser Thr Leu Asp Arg Tyr Lys Asp Thr Val Ile Thr Leu Leu
            85                  90                  95

Glu Leu Gly Ala Asn Val Asn Ala Arg Asp Tyr Cys Asp Lys Thr Pro
            100                 105                 110

Ile His Tyr Ala Ala Val Arg Asn Asn Val Val Ile Ile Asn Thr Leu
            115                 120                 125

Leu Asp Tyr Gly Ala Asp Ile Glu Ala Leu Ser Gln Lys Ile Gly Thr
    130                 135                 140

Val Leu His Phe Ala Leu Tyr Gly Thr Asn Pro Tyr Met Ser Val Lys
```

```
            145                 150                 155                 160
Thr Leu Ile Asp Arg Gly Ala Asn Val Asn Ser Lys Asn Lys Tyr Leu
                    165                 170                 175
Ser Thr Pro Leu His Tyr Ala Cys Lys Lys Asn Cys Lys Pro Glu Val
                180                 185                 190
Ile Lys Met Leu Leu Asp Asn Gly Ala Asp Val Asn Ala Ile Asn Ile
            195                 200                 205
Arg Asn Gln Tyr Pro Leu Leu Ile Ala Leu Glu Tyr His Gly Ile Val
        210                 215                 220
Asn Ile Leu Leu His Tyr Gly Ala Glu Leu Arg Asp Ser Arg Val Ile
225                 230                 235                 240
Asp Lys Ser Leu Asn Ser Asn Met Phe Ser Phe Arg Tyr Ile Ile Ala
                245                 250                 255
His Ile Cys Ile Gln Asp Phe Ile Arg His Asp Ile Arg Ser Glu Val
                260                 265                 270
Asn Pro Leu Arg Glu Ile Ile Gln Ser Asp Asp Thr Phe Lys Ser Ile
            275                 280                 285
Trp Leu Ser Cys Lys Glu Leu Lys Asp Ile Ser Lys Ile Arg Ile
        290                 295                 300
Asn Met Phe Tyr Ser Leu Asp Ile Phe Val Ile Ser Lys Asn Met Asn
305                 310                 315                 320
Leu Leu His His Leu Val Asn Asn Pro Ile Ile Lys Glu Ile Asn Thr
                325                 330                 335
Tyr Tyr Phe Tyr Asn Tyr Gly Asp Arg Leu Lys Thr Ser Ile Ser Leu
                340                 345                 350
Ala Ser Asn Arg His Lys Ile Leu Glu Lys Ser Arg Ser Lys Leu Asp
                355                 360                 365
Glu Ile Leu Asp Ser Ser Gly Trp Ser Lys Leu Leu Arg Ile Ser Asn
        370                 375                 380
Ser Gln Tyr
385

(2) INFORMATION FOR SEQ ID NO:8:

(i) SEQUENCE CHARACTERISTICS:
        (A) LENGTH: 40 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:8:

AAAAATTGAA AAACTATTCT AATTTATTGC ACGGAGATCT                              40

(2) INFORMATION FOR SEQ ID NO:9:

(i) SEQUENCE CHARACTERISTICS:
        (A) LENGTH: 32 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO
```

(iv) ANTI-SENSE: NO (xi) SEQUENCE DESCRIPTION: SEQ ID NO:9:

AATTTCATTT TGTTTTTTTC TATGCTATAA AT                              32

(2) INFORMATION FOR SEQ ID NO:10:

(i) SEQUENCE CHARACTERISTICS:
             (A) LENGTH: 37 base pairs
             (B) TYPE: nucleic acid
             (C) STRANDEDNESS: double
             (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:10:

GTATCCTAAA ATTGAATTGT AATTATCGAT AATAAAT                         37

(2) INFORMATION FOR SEQ ID NO:11:

(i) SEQUENCE CHARACTERISTICS:
             (A) LENGTH: 42 base pairs
             (B) TYPE: nucleic acid
             (C) STRANDEDNESS: double
             (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:11:

TTTTTTTTTT TTTTTTTTTT GGCATATAAA TGAATTCGGA TC                   42

(2) INFORMATION FOR SEQ ID NO:12:

(i) SEQUENCE CHARACTERISTICS:
             (A) LENGTH: 4177 base pairs
             (B) TYPE: nucleic acid
             (C) STRANDEDNESS: double
             (D) TOPOLOGY: linear (ii) MOLECULE TYPE: DNA (genomic)

(iii) HYPOTHETICAL: NO (iv) ANTI-SENSE: NO (ix) FEATURE:
             (A) NAME/KEY: CDS
             (B) LOCATION: 115..1860

(ix) FEATURE:
             (A) NAME/KEY: CDS
             (B) LOCATION: 2095..3756

(xi) SEQUENCE DESCRIPTION: SEQ ID NO:12:

CATACTGGCC TCGAGGGCCG CGGCCGCCTG CAGGTCGACT CTAGAAAAAA TTGAAAAACT      60

ATTCTAATTT ATTGCACGGA GATCTTTTTT TTTTTTTTTT TTTTTGGCAT ATAA ATG       117
                                                              Met
                                                               1

AAT TCG GAT CCG GAC CGC GCC GTT AGC CAA GTT GCG TTA GAG AAT GAT       165
Asn Ser Asp Pro Asp Arg Ala Val Ser Gln Val Ala Leu Glu Asn Asp
         5                  10                  15

-continued

| | | |
|---|---|---|
| GAA AGA GAG GCA AAA AAT ACA TGG CGC TTG ATA TTC CGG ATT GCA ATC<br>Glu Arg Glu Ala Lys Asn Thr Trp Arg Leu Ile Phe Arg Ile Ala Ile<br>20                   25                   30 | 213 | |
| TTA TTC TTA ACA GTA GTG ACC TTG GCT ATA TCT GTA GCC TCC CTT TTA<br>Leu Phe Leu Thr Val Val Thr Leu Ala Ile Ser Val Ala Ser Leu Leu<br>35                  40                  45 | 261 | |
| TAT AGC ATG GGG GCT AGC ACA CCT AGC GAT CTT GTA GGC ATA CCG ACT<br>Tyr Ser Met Gly Ala Ser Thr Pro Ser Asp Leu Val Gly Ile Pro Thr<br>50                   55                 60              65 | 309 | |
| AGG ATT TCC AGG GCA GAA GAA AAG ATT ACA TCT ACA CTT GGT TCC AAT<br>Arg Ile Ser Arg Ala Glu Glu Lys Ile Thr Ser Thr Leu Gly Ser Asn<br>70                  75                  80 | 357 | |
| CAA GAT GTA GTA GAT AGG ATA TAT AAG CAA GTG GCC CTT GAG TCT CCA<br>Gln Asp Val Val Asp Arg Ile Tyr Lys Gln Val Ala Leu Glu Ser Pro<br>85                  90                95 | 405 | |
| TTG GCA TTG TTA AAT ACT GAG ACC ACA ATT ATG AAC GCA ATA ACA TCT<br>Leu Ala Leu Leu Asn Thr Glu Thr Thr Ile Met Asn Ala Ile Thr Ser<br>100                105              110 | 453 | |
| CTC TCT TAT CAG ATT AAT GGA GCT GCA AAC AAC AGC GGG TGG GGG GCA<br>Leu Ser Tyr Gln Ile Asn Gly Ala Ala Asn Asn Ser Gly Trp Gly Ala<br>115                120              125 | 501 | |
| CCT ATT CAT GAC CCA GAT TAT ATA GGG GGG ATA GGC AAA GAA CTC ATT<br>Pro Ile His Asp Pro Asp Tyr Ile Gly Gly Ile Gly Lys Glu Leu Ile<br>130                135              140              145 | 549 | |
| GTA GAT GAT GCT AGT GAT GTC ACA TCA TTC TAT CCC TCT GCA TTT CAA<br>Val Asp Asp Ala Ser Asp Val Thr Ser Phe Tyr Pro Ser Ala Phe Gln<br>150                155              160 | 597 | |
| GAA CAT CTG AAT TTT ATC CCG GCG CCT ACT ACA GGA TCA GGT TGC ACT<br>Glu His Leu Asn Phe Ile Pro Ala Pro Thr Thr Gly Ser Gly Cys Thr<br>165                170              175 | 645 | |
| CGA ATA CCC TCA TTT GAC ATG AGT GCT ACC CAT TAC TGC TAC ACC CAT<br>Arg Ile Pro Ser Phe Asp Met Ser Ala Thr His Tyr Cys Tyr Thr His<br>180                185              190 | 693 | |
| AAT GTA ATA TTG TCT GGA TGC AGA GAT CAC TCA CAC TCA CAT CAG TAT<br>Asn Val Ile Leu Ser Gly Cys Arg Asp His Ser His Ser His Gln Tyr<br>195                200              205 | 741 | |
| TTA GCA CTT GGT GTG CTC CGG ACA TCT GCA ACA GGG AGG GTA TTC TTT<br>Leu Ala Leu Gly Val Leu Arg Thr Ser Ala Thr Gly Arg Val Phe Phe<br>210                215              220              225 | 789 | |
| TCT ACT CTG CGT TCC ATC AAC CTG GAC GAC ACC CAA AAT CGG AAG TCT<br>Ser Thr Leu Arg Ser Ile Asn Leu Asp Asp Thr Gln Asn Arg Lys Ser<br>230                235              240 | 837 | |
| TGC AGT GTG AGT GCA ACT CCC CTG GGT TGT GAT ATG CTG TGC TCG AAA<br>Cys Ser Val Ser Ala Thr Pro Leu Gly Cys Asp Met Leu Cys Ser Lys<br>245                250              255 | 885 | |
| GCC ACG GAG ACA GAG GAA GAA GAT TAT AAC TCA GCT GTC CCT ACG CGG<br>Ala Thr Glu Thr Glu Glu Glu Asp Tyr Asn Ser Ala Val Pro Thr Arg<br>260                265              270 | 933 | |
| ATG GTA CAT GGG AGG TTA GGG TTC GAC GGC CAA TAT CAC GAA AAG GAC<br>Met Val His Gly Arg Leu Gly Phe Asp Gly Gln Tyr His Glu Lys Asp<br>275                280              285 | 981 | |
| CTA GAT GTC ACA ACA TTA TTC GGG GAC TGG GTG GCC AAC TAC CCA GGA<br>Leu Asp Val Thr Thr Leu Phe Gly Asp Trp Val Ala Asn Tyr Pro Gly<br>290                295              300              305 | 1029 | |
| GTA GGG GGT GGA TCT TTT ATT GAC AGC CGC GTG TGG TTC TCA GTC TAC<br>Val Gly Gly Gly Ser Phe Ile Asp Ser Arg Val Trp Phe Ser Val Tyr<br>310                315              320 | 1077 | |
| GGA GGG TTA AAA CCC AAT ACA CCC AGT GAC ACT GTA CAG GAA GGG AAA<br>Gly Gly Leu Lys Pro Asn Thr Pro Ser Asp Thr Val Gln Glu Gly Lys<br>325                330              335 | 1125 | |

```
TAT GTG ATA TAC AAG CGA TAC AAT GAC ACA TGC CCA GAT GAG CAA GAC      1173
Tyr Val Ile Tyr Lys Arg Tyr Asn Asp Thr Cys Pro Asp Glu Gln Asp
            340                 345                 350

TAC CAG ATT CGA ATG GCC AAG TCT TCG TAT AAG CCT GGA CGG TTT GGT      1221
Tyr Gln Ile Arg Met Ala Lys Ser Ser Tyr Lys Pro Gly Arg Phe Gly
        355                 360                 365

GGG AAA CGC ATA CAG CAG GCT ATC TTA TCT ATC AAA GTG TCA ACA TCC      1269
Gly Lys Arg Ile Gln Gln Ala Ile Leu Ser Ile Lys Val Ser Thr Ser
370                 375                 380                 385

TTA GGC GAA GAC CCG GTA CTG ACT GTA CCG CCC AAC ACA GTC ACA CTC      1317
Leu Gly Glu Asp Pro Val Leu Thr Val Pro Pro Asn Thr Val Thr Leu
                390                 395                 400

ATG GGG GCC GAA GGC AGA ATT CTC ACA GTA GGG ACA TCC CAT TTC TTG      1365
Met Gly Ala Glu Gly Arg Ile Leu Thr Val Gly Thr Ser His Phe Leu
            405                 410                 415

TAT CAG CGA GGG TCA TCA TAC TTC TCT CCC GCG TTA TTA TAT CCT ATG      1413
Tyr Gln Arg Gly Ser Ser Tyr Phe Ser Pro Ala Leu Leu Tyr Pro Met
        420                 425                 430

ACA GTC AGC AAC AAA ACA GCC ACT CTT CAT AGT CCT TAT ACA TTC AAT      1461
Thr Val Ser Asn Lys Thr Ala Thr Leu His Ser Pro Tyr Thr Phe Asn
    435                 440                 445

GCC TTC ACT CGG CCA GGT AGT ATC CCT TGC CAG GCT TCA GCA AGA TGC      1509
Ala Phe Thr Arg Pro Gly Ser Ile Pro Cys Gln Ala Ser Ala Arg Cys
450                 455                 460                 465

CCC AAC TCA TGT GTT ACT GGA GTC TAT ACA GAT CCA TAT CCC CTA ATC      1557
Pro Asn Ser Cys Val Thr Gly Val Tyr Thr Asp Pro Tyr Pro Leu Ile
                470                 475                 480

TTC TAT AGA AAC CAC ACC TTG CGA GGG GTA TTC GGG ACA ATG CTT GAT      1605
Phe Tyr Arg Asn His Thr Leu Arg Gly Val Phe Gly Thr Met Leu Asp
            485                 490                 495

GGT GAA CAA GCA AGA CTT AAC CCT GCG TCT GCA GTA TTC GAT AGC ACA      1653
Gly Glu Gln Ala Arg Leu Asn Pro Ala Ser Ala Val Phe Asp Ser Thr
        500                 505                 510

TCC CGC AGT CGC ATA ACT CGA GTG AGT TCA AGC AGC ATC AAA GCA GCA      1701
Ser Arg Ser Arg Ile Thr Arg Val Ser Ser Ser Ile Lys Ala Ala
    515                 520                 525

TAC ACA ACA TCA ACT TGT TTT AAA GTG GTC AAG ACC AAT AAG ACC TAT      1749
Tyr Thr Thr Ser Thr Cys Phe Lys Val Val Lys Thr Asn Lys Thr Tyr
530                 535                 540                 545

TGT CTC AGC ATT GCT GAA ATA TCT AAT ACT CTC TTC GGA GAA TTC AGA      1797
Cys Leu Ser Ile Ala Glu Ile Ser Asn Thr Leu Phe Gly Glu Phe Arg
                550                 555                 560

ATC GTC CCG TTA CTA GTT GAG ATC CTC AAA GAT GAC GGG GTT AGA GAA      1845
Ile Val Pro Leu Leu Val Glu Ile Leu Lys Asp Asp Gly Val Arg Glu
            565                 570                 575

GCC AGG TCT GGC TAGTTGAGTC AACTATGAAA GAGTTGGAAA GATGGCATTG          1897
Ala Arg Ser Gly
        580

TATCACCTAT CTTCTGCGAC ATCAAGAATC AAACCGAATG CCCGGATCCA TAATTAATTA    1957

ATTAATTTTT ATCCCTCGAC TCTAGAAAAA ATTGAAAAAC TATTCTAATT TATTGCACGG    2017

AGATCTTTTT TTTTTTTTTT TTTTTTGGCA TATAAATGAA TTCGGATCGA TCCCGGTTGG    2077

CGCCCTCCAG GTGCAGG ATG GGC TCC AGA CCT TCT ACC AAG AAC CCA GCA       2127
                    Met Gly Ser Arg Pro Ser Thr Lys Asn Pro Ala
                     1               5                  10

CCT ATG ATG CTG ACT ATC CGG GTC GCG CTG GTA CTG AGT TGC ATC TGT      2175
Pro Met Met Leu Thr Ile Arg Val Ala Leu Val Leu Ser Cys Ile Cys
            15                  20                  25
```

```
CCG GCA AAC TCC ATT GAT GGC AGG CCT CTT GCA GCT GCA GGA ATT GTG      2223
Pro Ala Asn Ser Ile Asp Gly Arg Pro Leu Ala Ala Ala Gly Ile Val
             30                  35                  40

GTT ACA GGA GAC AAA GCA GTC AAC ATA TAC ACC TCA TCC CAG ACA GGA      2271
Val Thr Gly Asp Lys Ala Val Asn Ile Tyr Thr Ser Ser Gln Thr Gly
     45                  50                  55

TCA ATC ATA GTT AAG CTC CTC CCG AAT CTG CCA AAG GAT AAG GAG GCA      2319
Ser Ile Ile Val Lys Leu Leu Pro Asn Leu Pro Lys Asp Lys Glu Ala
 60                  65                  70                  75

TGT GCG AAA GCC CCC TTG GAT GCA TAC AAC AGG ACA TTG ACC ACT TTG      2367
Cys Ala Lys Ala Pro Leu Asp Ala Tyr Asn Arg Thr Leu Thr Thr Leu
                 80                  85                  90

CTC ACC CCC CTT GGT GAC TCT ATC CGT AGG ATA CAA GAG TCT GTG ACT      2415
Leu Thr Pro Leu Gly Asp Ser Ile Arg Arg Ile Gln Glu Ser Val Thr
             95                 100                 105

ACA TCT GGA GGG GGG AGA CAG GGG CGC CTT ATA GGC GCC ATT ATT GGC      2463
Thr Ser Gly Gly Gly Arg Gln Gly Arg Leu Ile Gly Ala Ile Ile Gly
         110                 115                 120

GGT GTG GCT CTT GGG GTT GCA ACT GCC GCA CAA ATA ACA GCG GCC GCA      2511
Gly Val Ala Leu Gly Val Ala Thr Ala Ala Gln Ile Thr Ala Ala Ala
     125                 130                 135

GCT CTG ATA CAA GCC AAA CAA AAT GCT GCC AAC ATC CTC CGA CTT AAA      2559
Ala Leu Ile Gln Ala Lys Gln Asn Ala Ala Asn Ile Leu Arg Leu Lys
140                 145                 150                 155

GAG AGC ATT GCC GCA ACC AAT GAG GCT GTG CAT GAG GTC ACT GAC GGA      2607
Glu Ser Ile Ala Ala Thr Asn Glu Ala Val His Glu Val Thr Asp Gly
                 160                 165                 170

TTA TCG CAA CTA GCA GTG GCA GTT GGG AAG ATG CAG CAG TTC GTT AAT      2655
Leu Ser Gln Leu Ala Val Ala Val Gly Lys Met Gln Gln Phe Val Asn
             175                 180                 185

GAC CAA TTT AAT AAA ACA GCT CAG GAA TTA GAC TGC ATC AAA ATT GCA      2703
Asp Gln Phe Asn Lys Thr Ala Gln Glu Leu Asp Cys Ile Lys Ile Ala
         190                 195                 200

CAG CAA GTT GGT GTA GAG CTC AAC CTG TAC CTA ACC GAA TCG ACT ACA      2751
Gln Gln Val Gly Val Glu Leu Asn Leu Tyr Leu Thr Glu Ser Thr Thr
     205                 210                 215

GTA TTC GGA CCA CAA ATC ACT TCA CCT GCC TTA AAC AAG CTG ACT ATT      2799
Val Phe Gly Pro Gln Ile Thr Ser Pro Ala Leu Asn Lys Leu Thr Ile
220                 225                 230                 235

CAG GCA CTT TAC AAT CTA GCT GGT GGG AAT ATG GAT TAC TTG ACT          2847
Gln Ala Leu Tyr Asn Leu Ala Gly Gly Asn Met Asp Tyr Leu Leu Thr
                 240                 245                 250

AAG TTA GGT ATA GGG AAC AAT CAA CTC AGC TCA TTA ATC GGT AGC GGC      2895
Lys Leu Gly Ile Gly Asn Asn Gln Leu Ser Ser Leu Ile Gly Ser Gly
             255                 260                 265

TTA ATC ACC GGT AAC CCT ATT CTA TAC GAC TCA CAG ACT CAA CTC TTG      2943
Leu Ile Thr Gly Asn Pro Ile Leu Tyr Asp Ser Gln Thr Gln Leu Leu
         270                 275                 280

GGT ATA CAG GTA ACT CTA CCT TCA GTC GGG AAC CTA AAT AAT ATG CGT      2991
Gly Ile Gln Val Thr Leu Pro Ser Val Gly Asn Leu Asn Asn Met Arg
     285                 290                 295

GCC ACC TAC TTG GAA ACC TTA TCC GTA AGC ACA ACC AGG GGA TTT GCC      3039
Ala Thr Tyr Leu Glu Thr Leu Ser Val Ser Thr Thr Arg Gly Phe Ala
300                 305                 310                 315

TCG GCA CTT GTC CCA AAA GTG GTG ACA CGG GTC GGT TCT GTG ATA GAA      3087
Ser Ala Leu Val Pro Lys Val Val Thr Arg Val Gly Ser Val Ile Glu
                 320                 325                 330

GAA CTT GAC ACC TCA TAC TGT ATA GAA ACT GAC TTA GAT TTA TAT TGT      3135
Glu Leu Asp Thr Ser Tyr Cys Ile Glu Thr Asp Leu Asp Leu Tyr Cys
             335                 340                 345
```

```
ACA AGA ATA GTA ACG TTC CCT ATG TCC CCT GGT ATT TAC TCC TGC TTG      3183
Thr Arg Ile Val Thr Phe Pro Met Ser Pro Gly Ile Tyr Ser Cys Leu
        350                 355                 360

AGC GGC AAT ACA TCG GCC TGT ATG TAC TCA AAG ACC GAA GGC GCA CTT      3231
Ser Gly Asn Thr Ser Ala Cys Met Tyr Ser Lys Thr Glu Gly Ala Leu
365                 370                 375

ACT ACA CCA TAT ATG ACT ATC AAA GGC TCA GTC ATC GCT AAC TGC AAG      3279
Thr Thr Pro Tyr Met Thr Ile Lys Gly Ser Val Ile Ala Asn Cys Lys
380                 385                 390                 395

ATG ACA ACA TGT AGA TGT GTA AAC CCC CCG GGT ATC ATA TCG CAA AAC      3327
Met Thr Thr Cys Arg Cys Val Asn Pro Pro Gly Ile Ile Ser Gln Asn
                400                 405                 410

TAT GGA GAA GCC GTG TCT CTA ATA GAT AAA CAA TCA TGC AAT GTT TTA      3375
Tyr Gly Glu Ala Val Ser Leu Ile Asp Lys Gln Ser Cys Asn Val Leu
            415                 420                 425

TCC TTA GGC GGG ATA ACT TTA AGG CTC AGT GGG GAA TTC GAT GTA ACT      3423
Ser Leu Gly Gly Ile Thr Leu Arg Leu Ser Gly Glu Phe Asp Val Thr
        430                 435                 440

TAT CAG AAG AAT ATC TCA ATA CAA GAT TCT CAA GTA ATA ATA ACA GGC      3471
Tyr Gln Lys Asn Ile Ser Ile Gln Asp Ser Gln Val Ile Ile Thr Gly
    445                 450                 455

AAT CTT GAT ATC TCA ACT GAG CTT GGG AAT GTC AAC AAC TCG ATC AGT      3519
Asn Leu Asp Ile Ser Thr Glu Leu Gly Asn Val Asn Asn Ser Ile Ser
460                 465                 470                 475

AAT GCC TTG AAT AAG TTA GAG GAA AGC AAC AGA AAA CTA GAC AAA GTC      3567
Asn Ala Leu Asn Lys Leu Glu Glu Ser Asn Arg Lys Leu Asp Lys Val
                480                 485                 490

AAT GTC AAA CTG ACC AGC ACA TCT GCT CTC ATT ACC TAT ATC GTT TTG      3615
Asn Val Lys Leu Thr Ser Thr Ser Ala Leu Ile Thr Tyr Ile Val Leu
            495                 500                 505

ACT ATC ATA TCT CTT GTT TTT GGT ATA CTT AGC CTG ATT CTA GCA TGC      3663
Thr Ile Ile Ser Leu Val Phe Gly Ile Leu Ser Leu Ile Leu Ala Cys
        510                 515                 520

TAC CTA ATG TAC AAG CAA AAG GCG CAA CAA AAG ACC TTA TTA TGG CTT      3711
Tyr Leu Met Tyr Lys Gln Lys Ala Gln Gln Lys Thr Leu Leu Trp Leu
    525                 530                 535

GGG AAT AAT ACC CTA GAT CAG ATG AGA GCC ACT ACA AAA ATG TGAACACAGA   3763
Gly Asn Asn Thr Leu Asp Gln Met Arg Ala Thr Thr Lys Met
540                 545                 550

TGAGGAACGA AGGTTTCCCT AATAGTAATT TGTGTGAAAG TTCTGGTAGT CTGTCAGTTC    3823

GGAGAGTTAA GAAAAAAAAA AAACCCCCCC CCCCCCCCCC CCCCCCCCCT GCAGGCATCG    3883

TGGTGTCACG CTCGTCGTTT GGTATGGCTT CATTCAGCTC CGGTTCCCAA CGATCAAGGC    3943

GAGTTACATG ATCCCCCATG TTGTGCAAAA AAGCGGTTAG CTCCTTCGGT CCTCCGATCG    4003

TTGTCAGAAG TAAGTTGGCC GCAGTGTTAT CACTCATGGT TATGGCAGCA CTGCATAATT    4063

CTCTTACTGT CATGCCATCC GTAAGATGCT TTTCTGTGAC TGGTGAGTGA TCCATAATTA    4123

ATTAATTAAT TTTTATCCCG GGTCGACCTG CAGGCGGCCG CGGCCCTCGA GGCC          4177

(2) INFORMATION FOR SEQ ID NO:13:

(i) SEQUENCE CHARACTERISTICS:
        (A) LENGTH: 581 amino acids
        (B) TYPE: amino acid
        (D) TOPOLOGY: linear (ii) MOLECULE TYPE: protein (xi) SEQUENCE DESCRIPTION: SEQ ID NO:13:
```

-continued

```
Met Asn Ser Asp Pro Asp Arg Ala Val Ser Gln Val Ala Leu Glu Asn
 1               5                  10                  15

Asp Glu Arg Glu Ala Lys Asn Thr Trp Arg Leu Ile Phe Arg Ile Ala
                20                  25                  30

Ile Leu Phe Leu Thr Val Val Thr Leu Ala Ile Ser Val Ala Ser Leu
                35                  40                  45

Leu Tyr Ser Met Gly Ala Ser Thr Pro Ser Asp Leu Val Gly Ile Pro
    50                  55                  60

Thr Arg Ile Ser Arg Ala Glu Glu Lys Ile Thr Ser Thr Leu Gly Ser
 65                  70                  75                  80

Asn Gln Asp Val Val Asp Arg Ile Tyr Lys Gln Val Ala Leu Glu Ser
                85                  90                  95

Pro Leu Ala Leu Leu Asn Thr Glu Thr Thr Ile Met Asn Ala Ile Thr
                100                 105                 110

Ser Leu Ser Tyr Gln Ile Asn Gly Ala Ala Asn Asn Ser Gly Trp Gly
                115                 120                 125

Ala Pro Ile His Asp Pro Asp Tyr Ile Gly Ile Gly Lys Glu Leu
130                 135                 140

Ile Val Asp Asp Ala Ser Asp Val Thr Ser Phe Tyr Pro Ser Ala Phe
145                 150                 155                 160

Gln Glu His Leu Asn Phe Ile Pro Ala Pro Thr Thr Gly Ser Gly Cys
                165                 170                 175

Thr Arg Ile Pro Ser Phe Asp Met Ser Ala Thr His Tyr Cys Tyr Thr
                180                 185                 190

His Asn Val Ile Leu Ser Gly Cys Arg Asp His Ser His Ser His Gln
                195                 200                 205

Tyr Leu Ala Leu Gly Val Leu Arg Thr Ser Ala Thr Gly Arg Val Phe
    210                 215                 220

Phe Ser Thr Leu Arg Ser Ile Asn Leu Asp Asp Thr Gln Asn Arg Lys
225                 230                 235                 240

Ser Cys Ser Val Ser Ala Thr Pro Leu Gly Cys Asp Met Leu Cys Ser
                245                 250                 255

Lys Ala Thr Glu Thr Glu Glu Asp Tyr Asn Ser Ala Val Pro Thr
                260                 265                 270

Arg Met Val His Gly Arg Leu Gly Phe Asp Gly Gln Tyr His Glu Lys
                275                 280                 285

Asp Leu Asp Val Thr Thr Leu Phe Gly Asp Trp Val Ala Asn Tyr Pro
                290                 295                 300

Gly Val Gly Gly Gly Ser Phe Ile Asp Ser Arg Val Trp Phe Ser Val
305                 310                 315                 320

Tyr Gly Gly Leu Lys Pro Asn Thr Pro Ser Asp Thr Val Gln Glu Gly
                325                 330                 335

Lys Tyr Val Ile Tyr Lys Arg Tyr Asn Asp Thr Cys Pro Asp Glu Gln
                340                 345                 350

Asp Tyr Gln Ile Arg Met Ala Lys Ser Ser Tyr Lys Pro Gly Arg Phe
                355                 360                 365

Gly Gly Lys Arg Ile Gln Gln Ala Ile Leu Ser Ile Lys Val Ser Thr
                370                 375                 380

Ser Leu Gly Glu Asp Pro Val Leu Thr Val Pro Asn Thr Val Thr
385                 390                 395                 400

Leu Met Gly Ala Glu Gly Arg Ile Leu Thr Val Gly Thr Ser His Phe
                405                 410                 415

Leu Tyr Gln Arg Gly Ser Ser Tyr Phe Ser Pro Ala Leu Leu Tyr Pro
```

```
                420                 425                 430
Met Thr Val Ser Asn Lys Thr Ala Thr Leu His Ser Pro Tyr Thr Phe
            435                 440                 445

Asn Ala Phe Thr Arg Pro Gly Ser Ile Pro Cys Gln Ala Ser Ala Arg
    450                 455                 460

Cys Pro Asn Ser Cys Val Thr Gly Val Tyr Thr Asp Pro Tyr Pro Leu
465                 470                 475                 480

Ile Phe Tyr Arg Asn His Thr Leu Arg Gly Val Phe Gly Thr Met Leu
                485                 490                 495

Asp Gly Glu Gln Ala Arg Leu Asn Pro Ala Ser Ala Val Phe Asp Ser
            500                 505                 510

Thr Ser Arg Ser Arg Ile Thr Arg Val Ser Ser Ser Ile Lys Ala
        515                 520                 525

Ala Tyr Thr Thr Ser Thr Cys Phe Lys Val Val Lys Thr Asn Lys Thr
    530                 535                 540

Tyr Cys Leu Ser Ile Ala Glu Ile Ser Asn Thr Leu Phe Gly Glu Phe
545                 550                 555                 560

Arg Ile Val Pro Leu Leu Val Glu Ile Leu Lys Asp Asp Gly Val Arg
                565                 570                 575

Glu Ala Arg Ser Gly
            580

(2) INFORMATION FOR SEQ ID NO:14:

(i) SEQUENCE CHARACTERISTICS:
        (A) LENGTH: 553 amino acids
        (B) TYPE: amino acid
        (D) TOPOLOGY: linear (ii) MOLECULE TYPE: protein (xi) SEQUENCE DESCRIPTION: SEQ ID NO:14:

Met Gly Ser Arg Pro Ser Thr Lys Asn Pro Ala Pro Met Met Leu Thr
1               5                   10                  15

Ile Arg Val Ala Leu Val Leu Ser Cys Ile Cys Pro Ala Asn Ser Ile
            20                  25                  30

Asp Gly Arg Pro Leu Ala Ala Ala Gly Ile Val Val Thr Gly Asp Lys
        35                  40                  45

Ala Val Asn Ile Tyr Thr Ser Ser Gln Thr Gly Ser Ile Ile Val Lys
    50                  55                  60

Leu Leu Pro Asn Leu Pro Lys Asp Lys Glu Ala Cys Ala Lys Ala Pro
65                  70                  75                  80

Leu Asp Ala Tyr Asn Arg Thr Leu Thr Thr Leu Leu Thr Pro Leu Gly
                85                  90                  95

Asp Ser Ile Arg Arg Ile Gln Glu Ser Val Thr Thr Ser Gly Gly Gly
            100                 105                 110

Arg Gln Gly Arg Leu Ile Gly Ala Ile Ile Gly Gly Val Ala Leu Gly
        115                 120                 125

Val Ala Thr Ala Ala Gln Ile Thr Ala Ala Ala Leu Ile Gln Ala
    130                 135                 140

Lys Gln Asn Ala Ala Asn Ile Leu Arg Leu Lys Glu Ser Ile Ala Ala
145                 150                 155                 160

Thr Asn Glu Ala Val His Glu Val Thr Asp Gly Leu Ser Gln Leu Ala
                165                 170                 175

Val Ala Val Gly Lys Met Gln Gln Phe Val Asn Asp Gln Phe Asn Lys
            180                 185                 190
```

```
Thr Ala Gln Glu Leu Asp Cys Ile Lys Ile Ala Gln Val Gly Val
        195                 200                 205

Glu Leu Asn Leu Tyr Leu Thr Glu Ser Thr Val Phe Gly Pro Gln
        210                 215                 220

Ile Thr Ser Pro Ala Leu Asn Lys Leu Thr Ile Gln Ala Leu Tyr Asn
225                 230                 235                 240

Leu Ala Gly Gly Asn Met Asp Tyr Leu Leu Thr Lys Leu Gly Ile Gly
                245                 250                 255

Asn Asn Gln Leu Ser Ser Leu Ile Gly Ser Gly Leu Ile Thr Gly Asn
                260                 265                 270

Pro Ile Leu Tyr Asp Ser Gln Thr Gln Leu Leu Gly Ile Gln Val Thr
        275                 280                 285

Leu Pro Ser Val Gly Asn Leu Asn Asn Met Arg Ala Thr Tyr Leu Glu
290                 295                 300

Thr Leu Ser Val Ser Thr Thr Arg Gly Phe Ala Ser Ala Leu Val Pro
305                 310                 315                 320

Lys Val Val Thr Arg Val Gly Ser Val Ile Glu Glu Leu Asp Thr Ser
                325                 330                 335

Tyr Cys Ile Glu Thr Asp Leu Asp Leu Tyr Cys Thr Arg Ile Val Thr
                340                 345                 350

Phe Pro Met Ser Pro Gly Ile Tyr Ser Cys Leu Ser Gly Asn Thr Ser
        355                 360                 365

Ala Cys Met Tyr Ser Lys Thr Glu Gly Ala Leu Thr Thr Pro Tyr Met
        370                 375                 380

Thr Ile Lys Gly Ser Val Ile Ala Asn Cys Lys Met Thr Thr Cys Arg
385                 390                 395                 400

Cys Val Asn Pro Pro Gly Ile Ile Ser Gln Asn Tyr Gly Glu Ala Val
                405                 410                 415

Ser Leu Ile Asp Lys Gln Ser Cys Asn Val Leu Ser Leu Gly Gly Ile
                420                 425                 430

Thr Leu Arg Leu Ser Gly Glu Phe Asp Val Thr Tyr Gln Lys Asn Ile
        435                 440                 445

Ser Ile Gln Asp Ser Gln Val Ile Ile Thr Gly Asn Leu Asp Ile Ser
450                 455                 460

Thr Glu Leu Gly Asn Val Asn Asn Ser Ile Ser Asn Ala Leu Asn Lys
465                 470                 475                 480

Leu Glu Glu Ser Asn Arg Lys Leu Asp Lys Val Asn Val Lys Leu Thr
                485                 490                 495

Ser Thr Ser Ala Leu Ile Thr Tyr Ile Val Leu Thr Ile Ile Ser Leu
                500                 505                 510

Val Phe Gly Ile Leu Ser Leu Ile Leu Ala Cys Tyr Leu Met Tyr Lys
        515                 520                 525

Gln Lys Ala Gln Gln Lys Thr Leu Leu Trp Leu Gly Asn Asn Thr Leu
530                 535                 540

Asp Gln Met Arg Ala Thr Thr Lys Met
545                 550

(2) INFORMATION FOR SEQ ID NO:15:

(i) SEQUENCE CHARACTERISTICS:
        (A) LENGTH: 182 base pairs
        (B) TYPE: nucleic acid
        (C) STRANDEDNESS: double
        (D) TOPOLOGY: linear
```

(ii) MOLECULE TYPE: DNA (genomic)

(iii) HYPOTHETICAL: NO (iv) ANTI-SENSE: NO (xi) SEQUENCE DESCRIPTION: SEQ ID NO:15:

GGCCTCGAGG GCCGCGGCCG CCTGCAGGTC GACTCTAGAA AAAATTGAAA AACTATTCTA      60

ATTTATTGCA CGGAGATCTT TTTTTTTTTT TTTTTTTTTG GCATATAAAT GAATTCGGAT     120

CCGGACCGCG CCGTTAGCCA AGTTGCGTTA GAGAATGATG AAAGAGAGGC AAAAAATACA     180

TG                                                                   182

(2) INFORMATION FOR SEQ ID NO:16:

(i) SEQUENCE CHARACTERISTICS:
            (A) LENGTH: 178 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:16:

ATCTTCTGCG ACATCAAGAA TCAAACCGAA TGCCCGGATC CATAATTAAT TAATTAATTT      60

TTATCCCTCG ACTCTAGAAA AAATTGAAAA ACTATTCTAA TTTATTGCAC GGAGATCTTT     120

TTTTTTTTTT TTTTTTTTGG CATATAAATG AATTCGGATC GATCCCGGTT GGCGCCCT      178

(2) INFORMATION FOR SEQ ID NO:17:

(i) SEQUENCE CHARACTERISTICS:
            (A) LENGTH: 60 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:17:

AAAAACCCCC CCCCCCCCCC CCCCCCCCCC CTGCAGGCAT CGTGGTGTCA CGCTCGTCGT      60

(2) INFORMATION FOR SEQ ID NO:18:

(i) SEQUENCE CHARACTERISTICS:
            (A) LENGTH: 120 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:18:

ATAATTCTCT TACTGTCATG CCATCCGTAA GATGCTTTTC TGTGACTGGT GAGTGATCCA      60

TAATTAATTA ATTAATTTTT ATCCCGGGTC GACCTGCAGG CGGCCGCGGC CCTCGAGGCC     120

(2) INFORMATION FOR SEQ ID NO:19:

(i) SEQUENCE CHARACTERISTICS:
        (A) LENGTH: 1305 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: CDS
        (B) LOCATION: 1..1305

(xi) SEQUENCE DESCRIPTION: SEQ ID NO:19:

```
ATG CAC CGT CCT CAT CTC AGA CGG CAC TCG CGT TAC TAC GCG AAA GGA      48
Met His Arg Pro His Leu Arg Arg His Ser Arg Tyr Tyr Ala Lys Gly
 1               5                  10                  15

GAG GTG CTT AAC AAA CAC ATG GAT TGC GGT GGA AAA CGG TGC TGC TCA      96
Glu Val Leu Asn Lys His Met Asp Cys Gly Gly Lys Arg Cys Cys Ser
                20                  25                  30

GGC GCA GCT GTA TTC ACT CTT TTC TGG ACT TGT GTC AGG ATT ATG CGG     144
Gly Ala Ala Val Phe Thr Leu Phe Trp Thr Cys Val Arg Ile Met Arg
            35                  40                  45

GAG CAT ATC TGC TTT GTA CGC AAC GCT ATG GAC CGC CAT TTA TTT TTG     192
Glu His Ile Cys Phe Val Arg Asn Ala Met Asp Arg His Leu Phe Leu
        50                  55                  60

AGG AAT GCT TTT TGG ACT ATC GTA CTG CTT TCT TCC TTC GCT AGC CAG     240
Arg Asn Ala Phe Trp Thr Ile Val Leu Leu Ser Ser Phe Ala Ser Gln
 65                  70                  75                  80

AGC ACC GCC GCC GTC ACG TAC GAC TAC ATT TTA GGC CGT CGC GCG CTC     288
Ser Thr Ala Ala Val Thr Tyr Asp Tyr Ile Leu Gly Arg Arg Ala Leu
                85                  90                  95

GAC GCG CTA ACC ATA CCG GCG GTT GGC CCG TAT AAC AGA TAC CTC ACT     336
Asp Ala Leu Thr Ile Pro Ala Val Gly Pro Tyr Asn Arg Tyr Leu Thr
            100                 105                 110

AGG GTA TCA AGA GGC TGC GAC GTT GTC GAG CTC AAC CCG ATT TCT AAC     384
Arg Val Ser Arg Gly Cys Asp Val Val Glu Leu Asn Pro Ile Ser Asn
        115                 120                 125

GTG GAC GAC ATG ATA TCG GCG GCC AAA GAA AAA GAG AAG GGG GGC CCT     432
Val Asp Asp Met Ile Ser Ala Ala Lys Glu Lys Glu Lys Gly Gly Pro
130                 135                 140

TTC GAG GCC TCC GTC GTC TGG TTC TAC GTG ATT AAG GGC GAC GAC GGC     480
Phe Glu Ala Ser Val Val Trp Phe Tyr Val Ile Lys Gly Asp Asp Gly
145                 150                 155                 160

GAG GAC AAG TAC TGT CCA ATC TAT AGA AAA GAG TAC AGG GAA TGT GGC     528
Glu Asp Lys Tyr Cys Pro Ile Tyr Arg Lys Glu Tyr Arg Glu Cys Gly
                165                 170                 175

GAC GTA CAA CTG CTA TCT GAA TGC GCC GTT CAA TCT GCA CAG ATG TGG     576
Asp Val Gln Leu Leu Ser Glu Cys Ala Val Gln Ser Ala Gln Met Trp
            180                 185                 190

GCA GTG GAC TAT GTT CCT AGC ACC CTT GTA TCG CGA AAT GGC GCG GGA     624
Ala Val Asp Tyr Val Pro Ser Thr Leu Val Ser Arg Asn Gly Ala Gly
        195                 200                 205

CTG ACT ATA TTC TCC CCC ACT GCT GCG CTC TCT GGC CAA TAC TTG CTG     672
Leu Thr Ile Phe Ser Pro Thr Ala Ala Leu Ser Gly Gln Tyr Leu Leu
    210                 215                 220

ACC CTG AAA ATC GGG AGA TTT GCG CAA ACA GCT CTC GTA ACT CTA GAA     720
Thr Leu Lys Ile Gly Arg Phe Ala Gln Thr Ala Leu Val Thr Leu Glu
```

```
                225                 230                 235                 240
GTT AAC GAT CGC TGT TTA AAG ATC GGG TCG CAG CTT AAC TTT TTA CCG                  768
Val Asn Asp Arg Cys Leu Lys Ile Gly Ser Gln Leu Asn Phe Leu Pro
                    245                 250                 255

TCG AAA TGC TGG ACA ACA GAA CAG TAT CAG ACT GGA TTT CAA GGC GAA                  816
Ser Lys Cys Trp Thr Thr Glu Gln Tyr Gln Thr Gly Phe Gln Gly Glu
                260                 265                 270

CAC CTT TAT CCG ATC GCA GAC ACC AAT ACA CGA CAC GCG GAC GAC GTA                  864
His Leu Tyr Pro Ile Ala Asp Thr Asn Thr Arg His Ala Asp Asp Val
            275                 280                 285

TAT CGG GGA TAC GAA GAT ATT CTG CAG CGC TGG AAT AAT TTG CTG AGG                  912
Tyr Arg Gly Tyr Glu Asp Ile Leu Gln Arg Trp Asn Asn Leu Leu Arg
        290                 295                 300

AAA AAG AAT CCT AGC GCG CCA GAC CCT CGT CCA GAT AGC GTC CCG CAA                  960
Lys Lys Asn Pro Ser Ala Pro Asp Pro Arg Pro Asp Ser Val Pro Gln
305                 310                 315                 320

GAA ATT CCC GCT GTA ACC AAG AAA GCG GAA GGG CGC ACC CCG GAC GCA                 1008
Glu Ile Pro Ala Val Thr Lys Lys Ala Glu Gly Arg Thr Pro Asp Ala
                325                 330                 335

GAA AGC AGC GAA AAG AAG GCC CCT CCA GAA GAC TCG GAG GAC GAC ATG                 1056
Glu Ser Ser Glu Lys Lys Ala Pro Pro Glu Asp Ser Glu Asp Asp Met
            340                 345                 350

CAG GCA GAG GCT TCT GGA GAA AAT CCT GCC GCC CTC CCC GAA GAC GAC                 1104
Gln Ala Glu Ala Ser Gly Glu Asn Pro Ala Ala Leu Pro Glu Asp Asp
        355                 360                 365

GAA GTC CCC GAG GAC ACC GAG CAC GAT GAT CCA AAC TCG GAT CCT GAC                 1152
Glu Val Pro Glu Asp Thr Glu His Asp Asp Pro Asn Ser Asp Pro Asp
    370                 375                 380

TAT TAC AAT GAC ATG CCC GCC GTG ATC CCG GTG GAG GAG ACT ACT AAA                 1200
Tyr Tyr Asn Asp Met Pro Ala Val Ile Pro Val Glu Glu Thr Thr Lys
385                 390                 395                 400

AGT TCT AAT GCC GTC TCC ATG CCC ATA TTC GCG GCG TTC GTA GCC TGC                 1248
Ser Ser Asn Ala Val Ser Met Pro Ile Phe Ala Ala Phe Val Ala Cys
                405                 410                 415

GCG GTC GCG CTC GTG GGG CTA CTG GTT TGG AGC ATC GTA AAA TGC GCG                 1296
Ala Val Ala Leu Val Gly Leu Leu Val Trp Ser Ile Val Lys Cys Ala
            420                 425                 430

CGT AGC TAA                                                                     1305
Arg Ser
    435

(2) INFORMATION FOR SEQ ID NO:20:

(i) SEQUENCE CHARACTERISTICS:
        (A) LENGTH: 434 amino acids
        (B) TYPE: amino acid
        (D) TOPOLOGY: linear (ii) MOLECULE TYPE: protein (xi) SEQUENCE DESCRIPTION: SEQ ID NO:20:

Met His Arg Pro His Leu Arg Arg His Ser Arg Tyr Tyr Ala Lys Gly
  1               5                  10                  15

Glu Val Leu Asn Lys His Met Asp Cys Gly Gly Lys Arg Cys Cys Ser
                20                  25                  30

Gly Ala Ala Val Phe Thr Leu Phe Trp Thr Cys Val Arg Ile Met Arg
            35                  40                  45

Glu His Ile Cys Phe Val Arg Asn Ala Met Asp Arg His Leu Phe Leu
        50                  55                  60

Arg Asn Ala Phe Trp Thr Ile Val Leu Leu Ser Ser Phe Ala Ser Gln
```

-continued

```
              65                  70                  75                  80
    Ser Thr Ala Ala Val Thr Tyr Asp Tyr Ile Leu Gly Arg Arg Ala Leu
                        85                  90                  95

Asp Ala Leu Thr Ile Pro Ala Val Gly Pro Tyr Asn Arg Tyr Leu Thr
                    100                 105                 110

Arg Val Ser Arg Gly Cys Asp Val Val Glu Leu Asn Pro Ile Ser Asn
                    115                 120                 125

Val Asp Asp Met Ile Ser Ala Ala Lys Glu Lys Glu Lys Gly Gly Pro
            130                 135                 140

Phe Glu Ala Ser Val Val Trp Phe Tyr Val Ile Lys Gly Asp Asp Gly
    145                 150                 155                 160

Glu Asp Lys Tyr Cys Pro Ile Tyr Arg Lys Glu Tyr Arg Glu Cys Gly
                    165                 170                 175

Asp Val Gln Leu Leu Ser Glu Cys Ala Val Gln Ser Ala Gln Met Trp
                    180                 185                 190

Ala Val Asp Tyr Val Pro Ser Thr Leu Val Ser Arg Asn Gly Ala Gly
                195                 200                 205

Leu Thr Ile Phe Ser Pro Thr Ala Ala Leu Ser Gly Gln Tyr Leu Leu
            210                 215                 220

Thr Leu Lys Ile Gly Arg Phe Ala Gln Thr Ala Leu Val Thr Leu Glu
    225                 230                 235                 240

Val Asn Asp Arg Cys Leu Lys Ile Gly Ser Gln Leu Asn Phe Leu Pro
                    245                 250                 255

Ser Lys Cys Trp Thr Thr Glu Gln Tyr Gln Thr Gly Phe Gln Gly Glu
                    260                 265                 270

His Leu Tyr Pro Ile Ala Asp Thr Asn Thr Arg His Ala Asp Asp Val
                275                 280                 285

Tyr Arg Gly Tyr Glu Asp Ile Leu Gln Arg Trp Asn Asn Leu Leu Arg
        290                 295                 300

Lys Lys Asn Pro Ser Ala Pro Asp Pro Arg Pro Asp Ser Val Pro Gln
    305                 310                 315                 320

Glu Ile Pro Ala Val Thr Lys Lys Ala Glu Gly Arg Thr Pro Asp Ala
                    325                 330                 335

Glu Ser Ser Glu Lys Lys Ala Pro Pro Glu Asp Ser Glu Asp Asp Met
                    340                 345                 350

Gln Ala Glu Ala Ser Gly Glu Asn Pro Ala Ala Leu Pro Glu Asp Asp
                355                 360                 365

Glu Val Pro Glu Asp Thr Glu His Asp Asp Pro Asn Ser Asp Pro Asp
        370                 375                 380

Tyr Tyr Asn Asp Met Pro Ala Val Ile Pro Val Glu Glu Thr Thr Lys
    385                 390                 395                 400

Ser Ser Asn Ala Val Ser Met Pro Ile Phe Ala Ala Phe Val Ala Cys
                    405                 410                 415

Ala Val Ala Leu Val Gly Leu Leu Val Trp Ser Ile Val Lys Cys Ala
                    420                 425                 430

Arg Ser
```

RECOMBINANT FOWLPOX VIRUSES AND USES THEREOF

This application is a continuation-in-part of PCT International Application No. PCT/US94/02252, filed Feb. 28, 1994, which is a continuation of U.S. Ser. No. 08/024,156, filed Feb. 26, 1993, now abandoned, the contents of which are hereby incorporated by reference.

Within this application several publications are referenced by arabic numerals within parentheses. Full citations for these references may be found at the end of the specification immediately preceding the claims. The disclosures of these publications in their entireties are hereby incorporated by reference into this application in order to more fully describe the state of the art to which this invention pertains.

BACKGROUND OF THE INVENTION

The present invention relates to recombinant fowlpox virus useful in live vaccine to protect fowl against Newcastle disease virus and fowlpox virus.

The ability to isolate DNA and clone this isolated DNA into bacterial plasmids has greatly expanded the approaches available to make viral vaccines. The method used to make the present invention involve modifying cloned DNA sequences by insertions, deletions and single or multiple base changes. The modified DNA is then inserted into a viral genome, and the resulting virus may then be used in a vaccine to elicit an immune response in a host animal and provide protection to the animal against disease.

Fowlpox virus (FPV) is a member of the poxviridiae family of viruses. There are two subfamilies in this classification, and they are differentiated based upon the host range (vertebrate or invertebrate) of the virus. Among the vertebrate poxviruses, there is serological cross reactivity to group specific antigens that has aided in classification of the viruses into six genera, and FPV has been placed in the avipoxvirus genera along with seven additional poxviruses that primarily infect birds. In general, poxviruses are the largest of the animal viruses and can be visualized with the light microscope. Under the electron microscope, the virus takes on a biscuit like or oval shaped appearance. The principal chemical components of the poxviruses are protein (90% by weight), deoxyribonucleic acid (DNA) (3%) and lipid (5%), but in FPV the lipid component is ~⅓ of the dry weight. Polyacrylamide gel electrophoresis (PAGE) of solubilized virions indicates that there are >100 different proteins associated with the viruses that include: structural polypeptides, enzymes associated with translation of messenger ribonucleic acid (mRNA), enzymes involved in RNA synthesis, and enzymes associated with DNA replication. The genome of poxviruses consists double-stranded DNA that varies in base composition (32% G+C to 64% G+C) and length (140 kilobasepairs [kb] to 280 kb for FPV) depending upon individual virus. The complete nucleotide sequence of the vaccina virus (VV) genome has recently been determined, and most of the essential genes have been found to lie within the highly conserved middle region of the genome while nonessential functions seem to map nearer to the termini of the DNA. The poxviruses are unique in their propensity to replicate within the cytoplasmic space of the infected cell, and in the case of VV, mature virus particles are moved out of the assembly areas and into the periphery of the cell where additional membrane encapsulation occurs. With FPV, the assembled viral particles become associated with a dense viral-derived protein matrix that occludes the virus in the form of cellular inclusions that may help protect the virion from lytic activities. Depending upon the specific poxvirus and strain (from 1% to 30% of different mature VV strains) varying levels of mature virus can be found extracellularly, but the majority of the virus population remains associated with the cell at the end of the growth cycle.

Fowlpox is unique throughout the world, but because its host-range is limited to birds it is not considered to be a public health hazard. All chickens can be infected by the virus with a resulting decline in the growth rate of the bird and temporary decreases in egg production. Usually, transmission of FPV occurs through physical contact of injured skin, but there are reports that the virus is also transmitted via arthropod vectors. After an incubation period of four to ten days, the disease is typically manifested in the following ways: skin lesions in non-feathered areas, lesions of the nasal passages, and lesions of the mouth. A normal FPV infection usually lasts three to four weeks, and afterward the bird is conferred life-long immunity to the disease.

Currently, conventionally derived FPV vaccines are being used in commercial settings to provide protection to chickens and turkeys. Typically, the vaccine viruses are attenuated by serial passage in cell culture selecting for strains that have altered growth and/or virulence properties. The modified live vaccine is prepared by growth in vitro in chicken embryo fibroblast cells or by growth on the chorioallantoic membrane of the chicken embryo. The vaccine virus is given to birds subcutaneously.

The present invention concerns the use of FPV as a vector for the delivery of specific vaccine antigens to poultry. The idea of using live viruses as delivery systems for antigens (vectoring) has a long history that is associated with introduction of the first live viral vaccines. The antigens that were delivered were not foreign but were naturally expressed by the live virus in the vaccine. The use of viruses to deliver foreign antigens in the modern sense became obvious with the recombinant DNA studies. The vaccinia virus was the vector and various antigens from other disease causing pathogens were the foreign antigens, and the vaccine was created by genetic engineering. While the concept became obvious with these disclosures, what was not obvious were the answers to more practical questions concerning what makes the best candidate viral vector and what constitutes the best foreign gene or gene to deliver. In answering these questions, details of the pathogenicity, site of replication or growth, the kind of elicited immune response, expression levels for the virus and foreign gene of interest (GOI), its suitability for genetic engineering, its probability of being licensed by regulatory agencies, etc. are all factors in the configuration. The prior art does not teach these questions of utility.

The presently preferred method for creating recombinant poxviruses uses a plasmid of bacterial origin that contains at least one cassette consisting of a poxvirus promoter followed by the gene of interest. The cassette(s) is flanked by poxvirus genomic DNA sequences that direct the gene of interest to the corresponding homologous nonessential region of the viral genome by homologous recombination. Cells are initially infected with the wild-type virus, and shortly thereafter the plasmid DNA is introduced into the infected cells. Since poxviruses have their own RNA polymerase and transcriptional apparatus, it is necessary that the gene of interest be regulated by a promoter of poxvirus origin. There are three characteristic poxvirus promoters that are differentiated based upon their temporal regulation of gene expression relative to the infective cycle of the virus: early, intermediate and late expression. Each promoter type can be identified by a typical consensus sequence that is ~30 bp in length and specific to each promoter type. In vaccinia virus, some viral genes are regulated by tandem early/late promoters that can be used by the virus to continually express the downstream gene throughout the infective cycle.

It is generally agreed that poxviruses contain non-essential regions of DNA in various parts of the genome, and that modifications of these regions can either attenuate the virus, leading to a non-pathogenic strain from which a vaccine may be derived, or give rise to genomic instabilities that yield mixed populations of virus. The degree of attenuation of the virus is important to the utility of the virus as a vaccine. Insertions or deletions which cause too much attenuation or genetic deletions which cause too much attenuation or genetic instability of the virus will result in a vaccine that fails to elicit an adequate immune response. Although several examples of deletions/insertions are known for poxviruses, the appropriate configuration is not readily apparent.

Thus far, gene expression from foreign genes of interest have been inserted into the genome of poxviruses has been obtained for five different pox viruses: vaccinia, canary pox, pigeon pox, raccoon pox and fowlpox. Vaccinia virus is the classically studied poxvirus, and it has been used extensively to vector foreign genes of interest; it is the subject of U.S. Pat. Nos. 4,603,112 and 4,722,848. Raccoon pox (Esposito, et al., 1988) and Canary pox (Taylor, et al., 1991) have bene used to express antigens from the rabies virus. More recently, FPV has been used to vector a number of different foreign gene of interest, and is the subject of patent applications (EPA 0 284 416, PCT WO 89/03429, PCT WO 89/12684, PCT WO 91/02072, PCT WO 89/03879, PCT etc.). However, these publications do not teach the vectored antigen configuration, the FPV insertion sites, or the promoter sequences and the arrangement of the present invention.

A foreign gene of interest targeted for insertion into the genome of FPV can be obtained from any pathogenic organism of interest. Typically, the gene of interest will be derived from pathogens that cause diseases in poultry that have an economic impact on the poultry industry. The genes can be derived from organisms for which there are existing vaccines, and because of the novel advantages of the vectoring technology the FPV derived vaccines will be superior. Also, the gene of interest may be derived from pathogens for which thee is currently no vaccine but where there is a requirement for control of the disease. Typically, the gene of interest encodes immunogenic polypeptides of the pathogen, and may represent surface proteins, secreted proteins and structural proteins.

One relevant avian pathogen that is a target for FPV vectoring in the present invention is Infectious Laryngotracheitis virus (ILT). ILT is a member of the herpesviridiae family, and this pathogen causes an acute disease of chickens which is characterized by respiratory depression, gasping and expectoration of bloody exudate. Viral replication is limited to cells of the respiratory tract, where in the trachea the infection gives rise to tissue erosion and hemorrhage. In chickens, no drug has been effective in reducing the degree of lesion formation or in decreasing clinical signs. Vaccination of birds with various modified forms of the ILT virus derived by cell passage and/or tedious regimes of administration have conferred acceptable protection in susceptible chickens. Because of the degree of attenuation of current ILT vaccines, care must be taken to assure that the correct level of virus is maintained; enough to provide protection, but not enough to cause disease in the flock.

An additional target for the FPV vectoring approach is Newcastle disease, an infectious, highly contagious and debilitating disease that is caused by the Newcastle disease virus (NDV), a single-stranded RNA virus of the paramyxovirus family. The various pathotypes of NDV (velongic, mesogenic, lentogenic) differ with regard to the severity of the disease, the specificity and symptoms, but most types seem to infect the respiratory system and the nervous system. NDV primarily infects chickens, turkeys and other avian species. Historically, vaccination has been used to prevent disease, but because of maternal antibody interference, life-span of the bird and route of administration, the producer needs to adapt immunization protocols to fit specific needs. Marek's disease of poultry is a lymphoproliferative tumor producing disease of poultry that primarily affects the peripheral nervous system and other visceral tissues and organs. Marek's disease exists in poultry producing countries throughout the world, and is an additional target described by the present invention for a FPV-based vectored vaccine. The causative agent of Marek's disease is a cell associated gammaherpesvirus that has been designated as Marek's disease virus (MDV). Three classes of viruses have been developed as conventional vaccines for protecting chickens against Marek's disease: attenuated serotype 1 MDV, herpesvirus of turkeys (HVT), and naturally avirulent serotype 2 isolates of MDV. Protection obtained with these vaccines is principally directed toward the tumorigenic aspect of the disease. The occurrence of excessive Marek's disease losses in such conventionally vaccinated flocks has led to the requirement for forming admixtures of the various vaccine types. Such polyvalent vaccines while generally ore effective in disease control, complicate the vaccine regime.

SUMMARY OF THE INVENTION

This invention provides a recombinant fowlpox virus comprising a foreign DNA sequence inserted into the fowlpox virus genomic DNA, wherein the foreign DNA sequence is inserted within a 3.5 kB EcoRI fragment of the fowlpox virus genomic DNA and is capable of being expressed in a fowlpox virus infected host cell.

The invention further provides homology vectors, vaccines and methods of immunization.

Numbers in parenthesis () refer to amino acids, and restriction sites in brackets [] indicate the remnants of sites which were destroyed during construction.

Figure 2A:
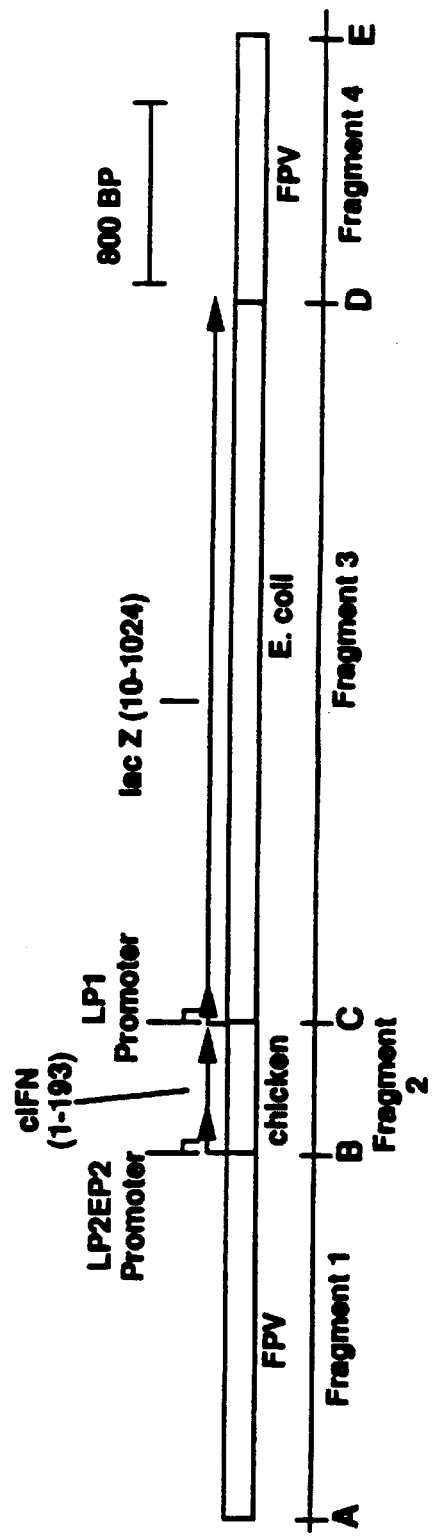
Figures 2, 2A:
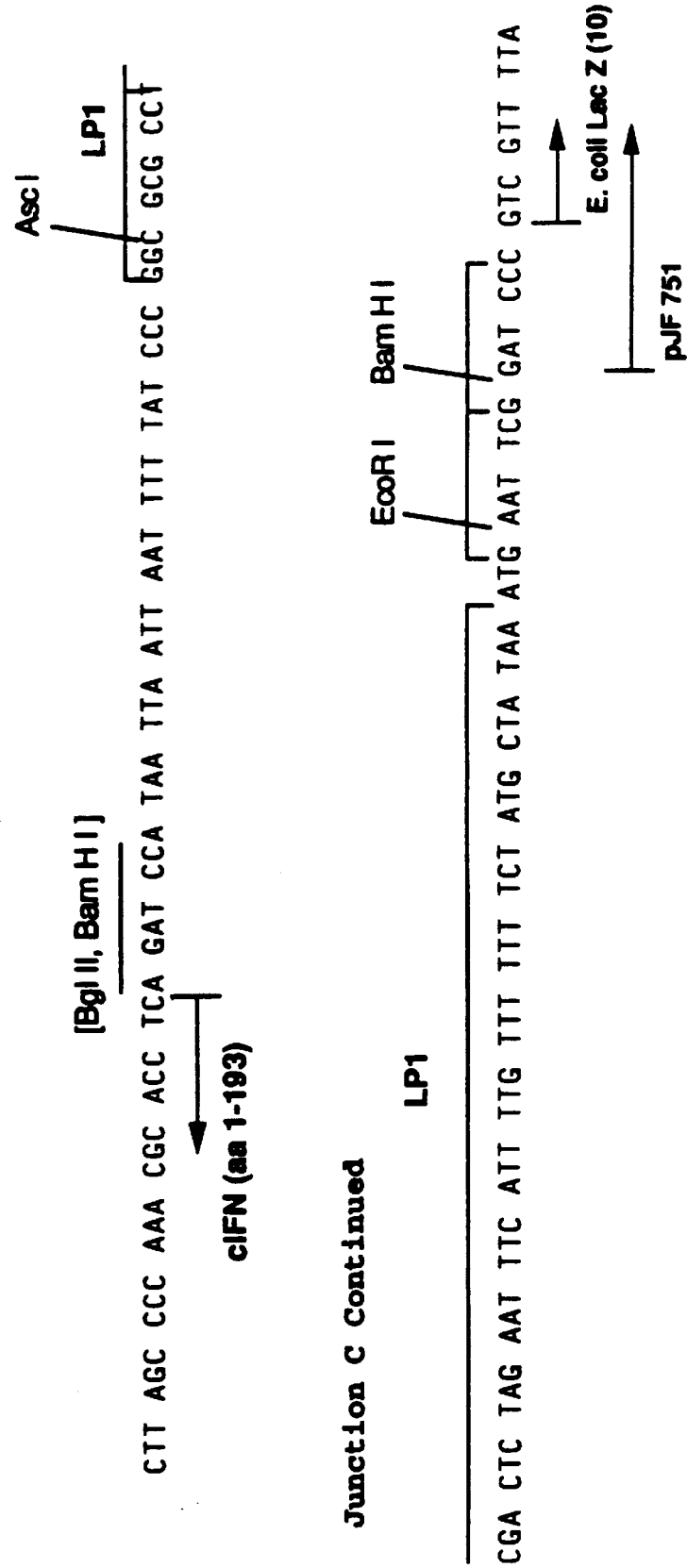
Figures 2, 2A, 3:
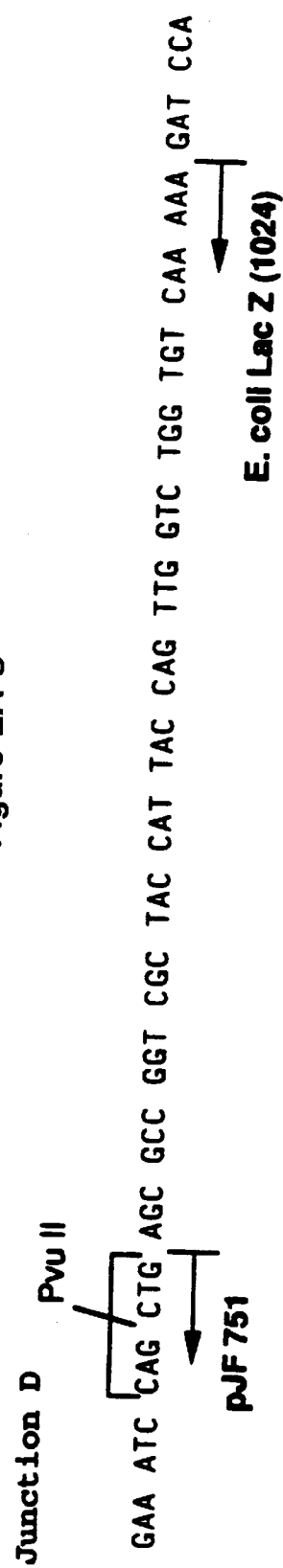
Figure 3A:
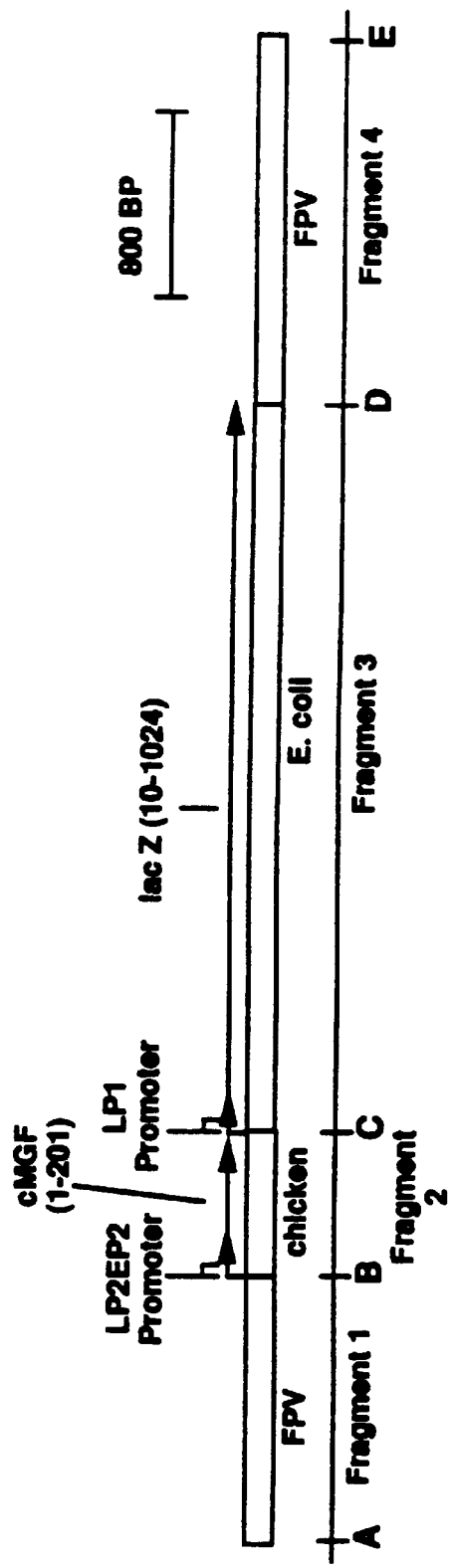
Figures 1, 3A:
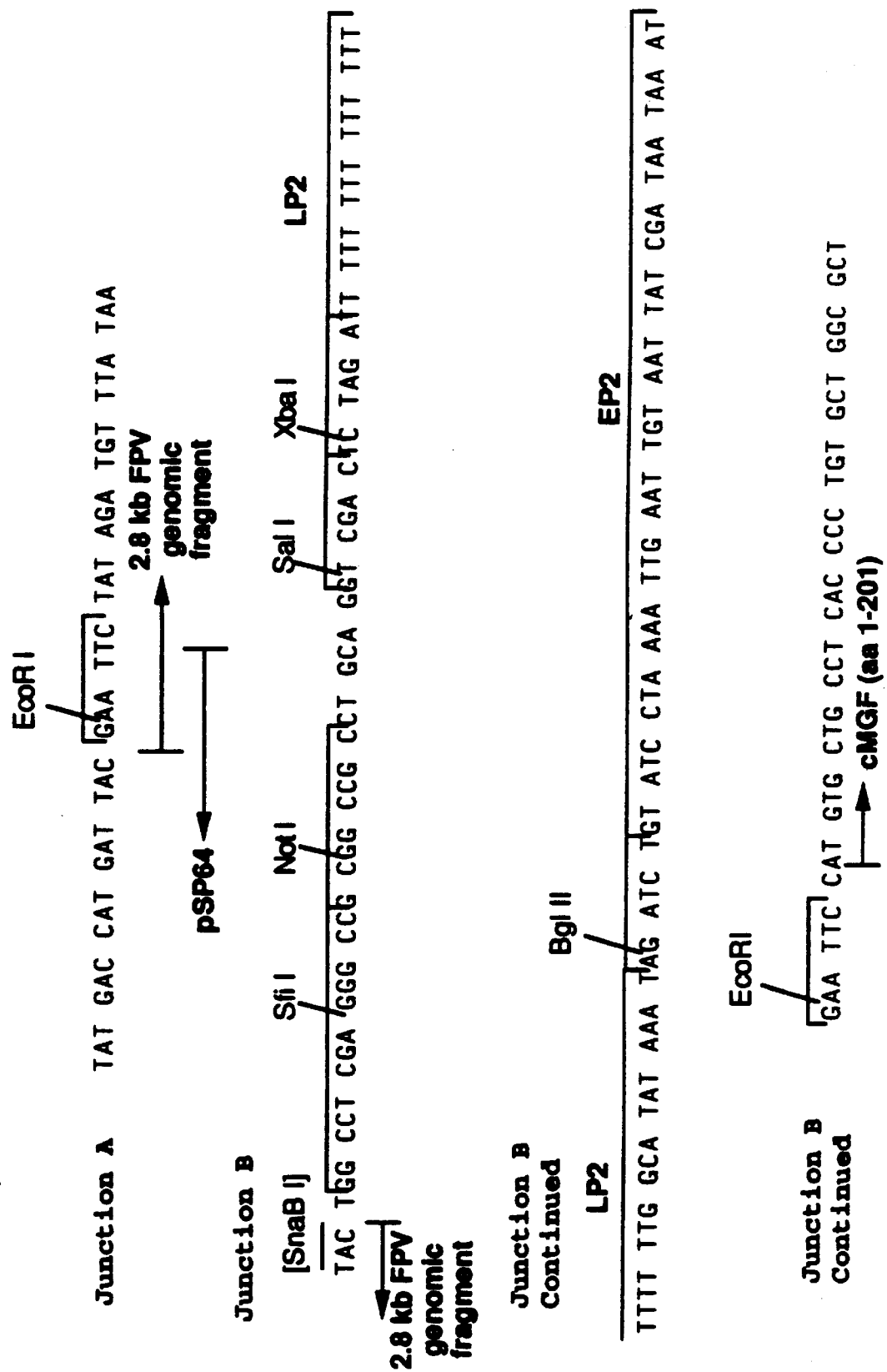
Figures 2, 3A:
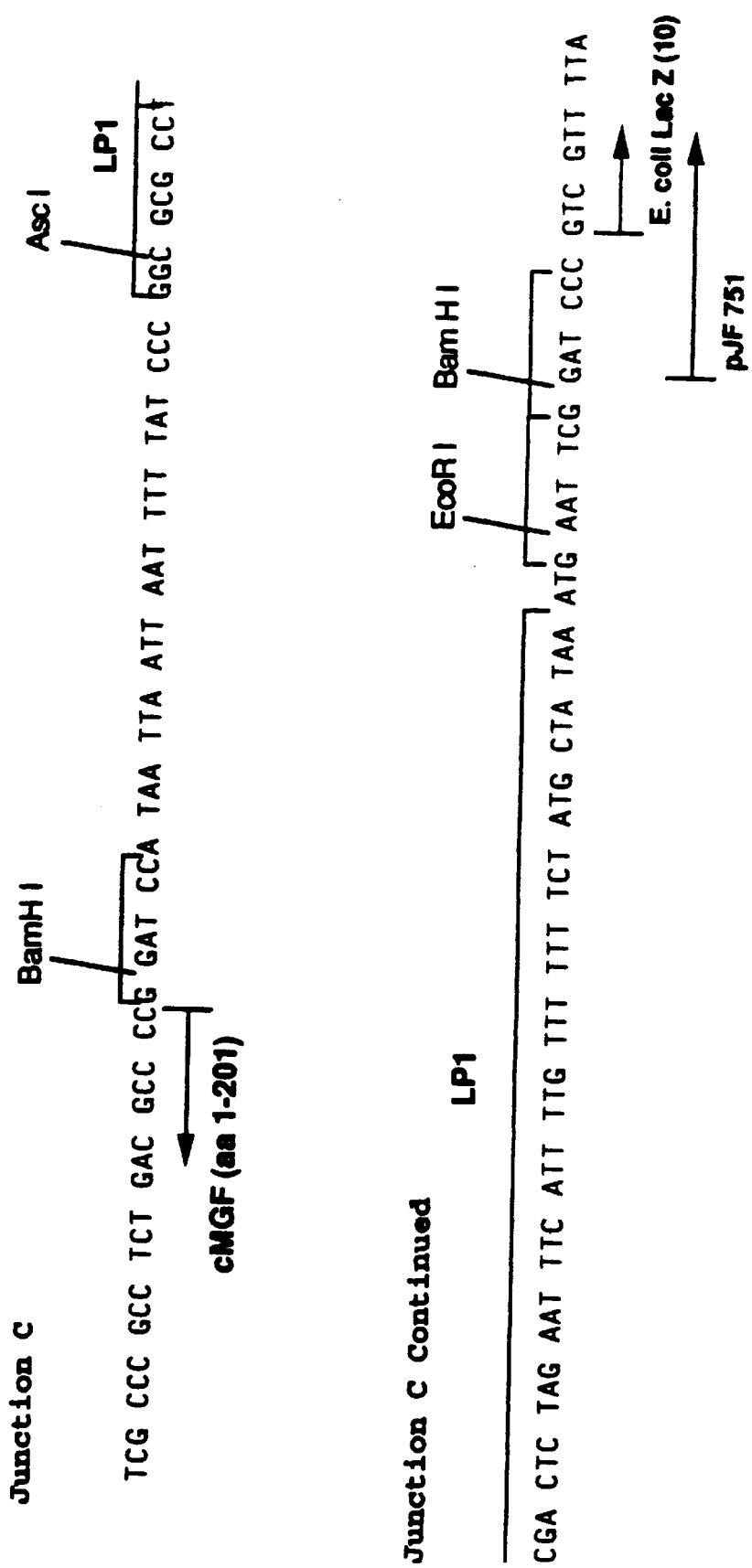
Figures 3, 3A:
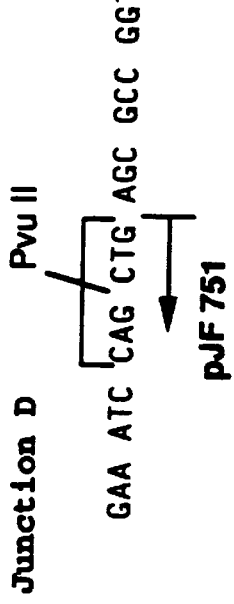

FIGS. 2A–2A-3: Detailed description of fowlpox virus S-FPV-099 and S-FPV-101 and the DNA insertion in Homology Vector 751-07.D1. Diagram showing the orientation of DNA fragments assembled in plasmid 751-07.D1. The origin of each fragment is indicated in the table. The sequences located at each of the junctions between fragments is also shown. FIGS. 2A–2A-3 show the sequences located at Junction A (SEQ ID NO: 37), B (SEQ ID NO: 38), C (SEQ ID NO:39), D (SEQ ID NO: 40) and E (SEQ ID NO: 41) between fragments and the sequences located at the junctions. The restriction sites used to generate each fragment as well as synthetic linker sequences which are used to join the fragments are described for each junction. The location of several gene coding regions and regulatory elements is also given. The following two conventions are used: numbers in parentheses, ( ), refer to amino acids, and restrictions sites in brackets, [ ], indicate the remnants of sites which are destroyed during construction. The following abbreviations are used: fowlpox virus (FPV), chicken interferon (cIFN), *Escherichia coli* (*E. coli*), pox synthetic late promoter 2 early promoter 2 (LP2EP2), pox synthetic late promoter 1 (LP1), base pairs (BP), polymerase chain reaction (PCR).

FIGS. 3A–3A-3: Detailed description of fowlpox virus S-FPV-100 and the DNA insertion in Homology Vector 751-56.C1. Diagram showing the orientation of DNA fragments assembled in plasmid 751-56.C1. The origin of each fragment is indicated in the table. The sequences located at each of the junctions between fragments is also shown. FIGS. 3A–3D show the sequences located at Junction A (SEQ ID NOS: 42), B (SEQ ID NO: 43), C (SEQ ID NO: 44), D (SEQ ID NO: 45) and E (SEQ ID NO: 46) between fragments and the sequences located at the junctions. The restriction sites used to generate each fragment as well as synthetic linker sequences which are used to join the fragments are described for each junction. The location of several gene coding regions and regulatory elements is also given. The following two conventions are used: numbers in parentheses, ( ), refer to amino acids, and restrictions sites in brackets, [ ], indicate the remnants of sites which are destroyed during construction. The following abbreviations are used: fowlpox virus (FPV), chicken myelomoncytic growth factor (cMGF), *Escherichia coli* (*E. coli*), pox synthetic late promoter 2 early promoter 2 (LP2EP2), pox synthetic late promoter 1 (LP1), base pairs (BP), polymerase chain reaction (PCR).

DETAILED DESCRIPTION OF THE INVENTION

This invention provides a recombinant fowlpox virus comprising a foreign DNA sequence inserted into the fowlpox virus genomic DNA, wherein the foreign DNA sequence is inserted within a 2.8 kB EcoRI fragment of the fowlpox virus genomic DNA and is capable of being expressed in a fowlpox virus infected host cell.

In one embodiment the foreign DNA sequence is inserted within a SnaBI restriction endonuclease site within the approximately 2.8 kB EcoRI fragment of the fowlpox virus genomic DNA.

This invention provides a recombinant fowlpox virus comprising a foreign DNA sequence inserted into the fowlpox virus genomic DNA, wherein the foreign DNA sequence is inserted within a 3.5 kB EcoRI fragment of the fowlpox virus genomic DNA and is capable of being expressed in a fowlpox virus infected host cell.

In one embodiment the recombinant fowlpox virus the foreign DNA sequence is inserted within a HpaI restriction endonuclease site within the approximately 3.5 kB EcoRI fragment of the fowlpox virus genomic DNA.

The present invention provides a recombinant fowlpox virus comprising a foreign DNA sequence inserted into the fowlpox virus genomic DNA, wherein the foreign DNA sequence is inserted within a 4.2 kB EcoRI fragment of the fowlpox virus genomic DNA and is capable of being expressed in a fowlpox virus infected host cell.

In one embodiment of the recombinant fowlpox virus foreign DNA sequence is inserted within a MluI restriction endonuclease site within the approximately 4.2 kB EcoRI fragment of the fowlpox virus genomic DNA.

The invention provides a recombinant fowlpox virus comprising a foreign DNA sequence inserted into the fowlpox virus genomic DNA, wherein the foreign DNA sequence is inserted within a non-essential region of the fowlpox virus genomic DNA and is capable of being expressed in a fowlpox virus infected host cell.

In one embodiment this invention provides a recombinant fowlpox virus wherein the foreign DNA sequence is inserted into an open reading frame within the non-essential region the fowlpox virus genomic DNA.

For purposes of this invention, "a recombinant fowlpox virus capable of replication" is a live fowlpox virus which has been generated by the recombinant methods well known to those of skill in the art, e.g., the methods set forth in HOMOLOGOUS RECOMBINATION PROCEDURE FOR GENERATING RECOMBINANT FPV in *Materials and Methods* and has not had genetic material essential for the replication of the recombinant fowlpox virus deleted.

The invention further provides a foreign DNA sequence or foreign RNA which encodes a polypeptide. Preferably, the polypeptide is antigenic in the animal. Preferably, this antigenic polypeptide is a linear polymer of more than 10 amino acids linked by peptide bonds which stimulates the animal to produce antibodies.

The invention further provides a recombinant fowlpox virus capable of replication which contains a foreign DNA encoding a polypeptide which is a detectable marker. Preferably the detectable marker is the polypeptide *E. coli* β-galactosidase or *E. coli* beta-glucuronidase.

In one embodiment of the recombinant fowlpox virus the foreign DNA sequence encodes a cytokine. In another embodiment the cytokine is chicken myelomonocytic growth factor (CMGF) or chicken interferon (cIFN). Cytokines include, but are not limited to: transforming growth factor beta, epidermal growth factor family, fibroblast growth factors, hepatocyte growth factor, insulin-like growth factor, vascular endothelial growth factor, interleukin 1, IL-1 receptor antagonist, interleukin-2, interleukin-3, interleukin-4, interleukin-5, interleukin-6, IL-6 soluble receptor, interleukin-7, interleukin-8, interleukin-9, interleukin-10, interleukin-11, interleukin-12, interleukin-13, angiogenin, chemokines, colony stimulating factors, granulocyte-macrophage colony stimulating factors, erythropoietin, interferon, interferon gamma, c-kit ligand, leukemia inhibitory factor, oncostatin M, pleiotrophin, secretory leukocyte protease inhibitor, stem cell factor, tumor necrosis factors, and soluble TNF receptors. These cytokines are from humans, bovine, equine, feline, canine, porcine or avian.

This invention provides a recombinant fowlpox virus further comprising a newcastle disease virus hemagglutinin (NDV HN), or a newcastle disease virus fusion (NDV F).

Antigenic polypeptide of a human pathogen which are derived from human herpesvirus include, but are not limited to: hepatitis B virus and hepatitis C virus hepatitis B virus surface and core antigens, hepatitis C virus, human immunodeficiency virus, herpes simplex virus-1, herpes simplex virus-2, human cytomegalovirus, Epstein-Barr virus, Varicella-Zoster virus, human herpesvirus-6, human herpesvirus-7, human influenza, measles virus, hantaan virus, pneumonia virus, rhinovirus, poliovirus, human respiratory syncytial virus, retrovirus, human T-cell leukemia virus, rabies virus, mumps virus, malaria (*Plasmodium falciparum*), Bordetella pertussis, Diptheria, *Rickettsia prowazekii, Borrelia berfdorferi*, Tetanus toxoid, malignant tumor antigens.

The antigenic polypeptide of an equine pathogen can derived from equine influenza virus, or equine herpesvirus. In one embodiment the antigenic polypeptide is equine influenza neuraminidase or hemagglutinin. Examples of such antigenic polypeptide are equine influenza virus type A/Alaska 91 neuraminidase, equine influenza virus type A/Prague 56 neuraminidase, equine influenza virus type A/Miami 63 neuraminidase, equine influenza virus type A/Kentucky 81 neuraminidase, equine influenza virus type A/Kentucky 92 neuraminidase equine herpesvirus type 1 glycoprotein B, equine herpesvirus type 1 glycoprotein D, *Streptococcus equi*, equine infectious anemia virus, equine encephalitis virus, equine rhinovirus and equine rotavirus.

The present invention further provides an antigenic polypeptide which includes, but is not limited to: hog cholera virus gE1, hog cholera virus gE2, swine influenza virus hemagglutinin, neuromanidase, matrix and nucleoprotein, pseudorabies virus gB, gC and gD, and PRRS virus ORF7.

For example, the antigenic polypeptide of derived from infectious bovine rhinotracheitis virus gE, bovine respiratory syncytial virus equine pathogen can derived from equine influenza virus is bovine respiratory syncytial virus attachment protein (BRSV G), bovine respiratory syncytial virus fusion protein (BRSV F), bovine respiratory syncytial virus nucleocapsid protein (BRSV N), bovine parainfluenza virus type 3 fusion protein, and the bovine parainfluenza virus type 3 hemagglutinin neuraminidase The present invention provides a recombinant fowlpox virus wherein the foreign DNA sequence encodes an antigenic polypeptide which is derived or derivable from a group consisting of: feline immunodeficiency virus gag, feline immunodeficiency virus env, infectious laryngotracheitis virus glycoprotein B, infectious laryngotracheitis virus gI, infectious laryngotracheitis virus gD, infectious bovine rhinotracheitis virus glycoprotein G, infectious bovine rhinotracheitis virus glycoprotein E, pseudorabies virus glycoprotein 50, pseudorabies virus II glycoprotein B, pseudorabies virus III glycoprotein C, pseudorabies virus glycoprotein E, pseudorabies virus glycoprotein H, marek's disease virus glycoprotein A, marek's disease virus glycoprotein B, marek's disease virus glycoprotein D, newcastle disease virus hemagglutinin or neuraminadase, newcastle disease virus fusion, infectious bursal disease virus VP2, infectious bursal disease virus VP3, infectious bursal disease virus VP4, infectious bursal disease virus polyprotein, infectious bronchitis virus spike, infectious bronchitis virus matrix, and chick anemia virus.

The present invention provides a recombinant fowlpox virus wherein the foreign DNA sequence is under control of a promoter. In one embodiment the foreign DNA sequence is under control of an endogenous upstream poxvirus promoter. In another embodiment the foreign DNA sequence is under control of a heterologous upstream promoter. In another embodiment the promoter is selected from a group consisting of: synthetic pox viral promoter, pox synthetic late promoter 1, pox synthetic late promoter 2 early promoter 2, pox O1L promoter, pox I4L promoter, pox I3L promoter, pox I2L promoter, pox I1L promoter, pox E10R promoter, HCMV immediate early, BHV-1.1 VP8, marek's disease virus glycoprotein A, marek's disease virus glycoprotein B, marek's disease virus glycoprotein D, laryngotracheitis virus glycoprotein I, infectious laryngotracheitis virus glycoprotein B, and infectious laryngotracheitis virus gD.

The present invention also provides a recombinant fowlpox virus designated S-FPV-097. The S-FPV-097 has been deposited on Feb. 25, 1994 pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. VR 2446.

The present invention also provides a vaccine which comprises an effective immunizing amount of the recombinant virus designated S-FPV-097 and a suitable carrier. The vaccine may contain either inactivated or live fowlpox virus S-FPV-097, although live virus is presently preferred. The present invention also provides a method of immunizing an animal, particularly poultry, against disease caused by fowlpox virus, Newcastle disease virus and infectious laryngotracheitis virus. This method comprises administering to the animal an effective immunizing dose of the vaccine of the present invention. The vaccine may be administered by any of the methods well known to those skilled in the art, for example, by intramuscular, intraperitoneal, intravenous or intradermal injection. Alternatively, the vaccine may be administered intranasally, orally, or ocularly.

The present invention also provides a recombinant fowlpox virus designated S-FPV-095. The present invention also provides a vaccine which comprises an effective immunizing amount of the recombinant virus designated S-FPV-095 and a suitable carrier. The vaccine may contain either inactivated or live fowlpox virus S-FPV-095, although live virus is presently preferred. The present invention also provides a method of immunizing an animal, particularly poultry, against disease caused by fowlpox virus, Newcastle disease virus and infectious laryngotracheitis virus. This method comprises administering to the animal an effective immunizing dose of the vaccine of the present invention. The vaccine may be administered by any of the methods well known to those skilled in the art, for example, by intramuscular, intraperitoneal, intravenous or intradermal injection. Alternatively, the vaccine may be administered intranasally, orally, or ocularly.

The present invention also provides a recombinant fowlpox virus designated S-FPV-074. The present invention also provides a vaccine which comprises an effective immunizing amount of the recombinant virus designated S-FPV-074 and a suitable carrier. The vaccine may contain either inactivated or live fowlpox virus S-FPV-074, although live virus is presently preferred. The present invention also provides a method of immunizing an animal, particularly poultry, against disease caused by fowlpox virus and Newcastle disease virus. This method comprises administering to the animal an effective immunizing dose of the vaccine of the present invention. The vaccine may be administered by any of the methods well known to those skilled in the art, for example, by intramuscular, intraperitoneal, intravenous or intradermal injection. Alternatively, the vaccine may be administered intranasally, orally, or ocularly.

The present invention also provides a recombinant fowlpox virus designated S-FPV-081. The present invention also provides a vaccine which comprises an effective immunizing amount of the recombinant virus designated S-FPV-081 and a suitable carrier. The vaccine may contain either inactivated or live fowlpox virus S-FPV-081, although live virus is presently preferred. The present invention also provides a method of immunizing an animal, particularly poultry, against disease caused by fowlpox virus and Marek's disease virus. This method comprises administering to the animal an effective immunizing dose of the vaccine of the present invention. The vaccine may be administered by any of the methods well known to those skilled in the art, for example, by intramuscular, intraperitoneal, intravenous or intradermal injection. Alternatively, the vaccine may be administered intranasally, orally, or ocularly.

The present invention also provides a recombinant fowlpox virus designated S-FPV-085. The present invention also provides a vaccine which comprises an effective immunizing amount of the recombinant virus designated S-FPV-085 and a suitable carrier. The vaccine may contain either inactivated or live fowlpox virus S-FPV-085, although live virus is presently preferred. The present invention also provides a method of immunizing an animal, particularly poultry, against disease caused by fowlpox virus, Newcastle disease virus, infectious laryngotracheitis virus and Marek's disease virus. This method comprises administering to the animal an effective immunizing dose of the vaccine of the present invention. The vaccine may be administered by any of the methods well known to those skilled in the art, for example, by intramuscular, intraperitoneal, intravenous or intradermal injection. Alternatively, the vaccine may be administered intranasally, orally, or ocularly.

The present invention also provides a recombinant fowlpox virus designated S-FPV-082, S-FPV-083, S-FPV-099, S-FPV-100, and S-FPV-101.

Suitable carriers for use with the recombinant fowlpox virus vaccines of the present invention are those well known in the art and include proteins, sugars, etc. One example of such a suitable carrier is a physiologically balanced culture medium containing one or more stabilizing agents such as stabilized, hydrolyzed proteins, lactose, etc.

An "effective immunizing amount" of the recombinant viruses of the present invention is an amount within the range of $10^2$–$10^9$ PFU/dose. Preferably, the effective immunizing amount is from about $10^3$–$10^5$ PFU/dose for the live virus vaccine. Preferable, the live vaccine is created by taking tissue culture fluids and adding stabilizing agents such as stabilized, hydrolyzed proteins.

Material and Methods
Preparation of Fowlpox Virus Stock Samples

Fowlpox virus samples were prepared by infecting chicken embryo fibroblast (CEF) cells at a multiplicity of infection of 0.01 PFU/cell in a 1:1 mixture of HAM's F10 medium and Medium 199 (F10/199) containing 2 mM glutamine and antibiotics (referred to as CEF negative medium). Prior to infection, the cell monolayers were washed once with CEF negative medium to remove fetal bovine serum. The FPV contained in the initial inoculum (0.5 ml for 10 cm plate; 10 ml for T175 cm flask) was allowed to absorb onto the cell monolayer for two hours, being redistributed every half hour. After this period, the original inoculum was brought up to an appropriate final volume by the addition of complete CEF medium (CEF negative medium plus 2% fetal bovine serum). The plates were incubated at 37° C. in 5% $CO_2$ until cytopathic effect was complete. The medium and cells were harvested, frozen at −70° C., thawed and dispensed into 1.0 ml vials and refrozen at −70° C. Virus titers typically range between $10^8$ and $10^7$ PFU/ml.

Preparation of FPV DNA

For fowlpox virus DNA isolation, a confluent monolayer of CEF cells in a T175 $cm^2$ flask was infected at a multiplicity of 0.1 and incubated 4–6 days until the cells were showing 100% cytopathic effect. The infected cells were harvested by scraping into the medium and centrifuging at 3000 rpm for 5 minutes in a clinical centrifuge. The medium was decanted, and the cell pellet was gently resuspended in 1.0 ml PBS (per T175) and subjected to two successive freeze-thaws (−70° C. to 37° C.). After the last thaw, the cells (on ice) were sonicated two times for 30 seconds each with 45 seconds cooling time in between. Cellular debris was removed by centrifuging (Sorvall RC-5B Superspeed Centrifuge) at 3000 rpm for 5 minutes in an HB4 rotor at 4° C. FPV virions, present in the supernatant, were pelleted by centrifugation at 15,000 rpm for 20 minutes at 4° C. in a SS34 rotor (Sorvall) and resuspended in 10 mM Tris (pH 7.5). This fraction was then layered onto a 36% sucrose gradient (w/v in 10 mM Tris pH 7.5) and centrifuged (Beckman L8-70M Ultracentrifuge) at 18,000 rpm for 60 minutes in a SW41 rotor at 4° C. The virion pellet was resuspended in 1.0 ml of 10 mM Tris pH 7.5 and sonicated on ice for 30 seconds. This fraction was layered onto a 20% to 50% continuous sucrose gradient and centrifuged at 16,000 rpm for 60 minutes in a SW41 rotor at 4° C. The FPV virion band located about three quarters down the gradient was harvested, diluted with 20% sucrose and pelleted by centrifugation at 18,000 rpm for 60 minutes in a SW41 rotor at 4° C. The resultant pellet was then washed once with 10 mM Tris pH 7.5 to remove traces of sucrose and finally resuspended in 10 mM Tris pH 7.5. FPV DNA was then extracted from the purified virions by lysis (four hours at 60° C.) following the addition of EDTA, SDS, and proteinase K to final concentrations of 20 mM, 0.5% and 0.5 mf/ml, respectively. After digestion, three phenol-chloroform (1:1) extractions were conducted and the sample precipitated by the addition of two volumes of absolute ethanol and incubated at −20° C. for 30 minutes. The sample was then centrifuged in an Eppendorf minifuge for five minutes at full speed. The supernatant was decanted, and the pellet air dried and rehydrated in 0.01 M Tris pH 7.5, 1 mM EDTA at 4° C.

Molecular Biological Techniques

Techniques for the manipulation of bacteria and DNA, including such procedures as digestion with restriction endonucleases, gel electrophoresis, extraction of DNA from gels, ligation, phosphorylation with kinase, treatment with phosphatase, growth of bacterial cultures, transformation of bacteria with DNA, and other molecular biological methods are described by Maniatis et al (1982) and Sambrook et al (1989). Except as noted, these were used with minor variation.

DNA Sequencing

Sequencing was performed using the SEQUENASE (U.S. Biochemical Corp. Cleveland, Ohio) genetically engineered form of T7 DNA polymerase with no 3' to 5' exonuclease activity as compared to native T7 DNA polymerase and $^{35}$S-DATP (NEN). Reactions using both the dGTP mixes and the dITP mixes were performed to clarify areas of compression. Alternatively, compressed areas were resolved on formamide gels. Templates were double-stranded plasmid subclones or single stranded M13 subclones, and primers were either made to the vector just outside the insert to be sequenced, or to previously obtained sequence. Sequence obtained was assembled and compared using Dnastar software. Manipulation and comparison of sequences obtained was performed with Superclone and Supersee programs from Coral Software.

Strategy for the Construction of Synthetic Pox Viral Promoters

For recombinant fowlpox vectors synthetic pox promoters offer several advantages including the ability to control the strength and timing of foreign gene expression. We chose to design four promoter cassettes EP1 (SEQ ID NO:8, LP1 (SEQ ID NO:9), EP2 (SEQ ID NO:10), and LP2 (SEQ ID NO:11) based on promoters that have been defined in the vaccinia virus (Bertholet et al. 1986, Davidson and Moss, 1989a, and Davidson and Moss, 1989b). Each cassette was designed to contain the DNA sequences defined in vaccina flanked by restriction sites which could be used to combine the cassettes in any order or combination. Initiator methionines were also designed into each cassette such that inframe fusions could be made at either EcoRI or BamHi sites. A set of translational stop codons in all three reading frames and an early transcriptional termination signal (Earl, et al., 1990) was also engineered downstream of the inframe fusion site. DNA encoding each cassette was synthesized according to standard techniques and cloned into the appropriate homology vectors.

cDNA Cloning Procedure cDNA cloning refers to the methods used to convert RNA molecules into DNA molecules following state of the art procedures. Applicants' methods are described in (Gubler and Hoffman, 1983). Bethesda Research Laboratories (Gaithersburg, Md.) have designed a cDNA Cloning Kit that is very similar to the procedures used by applicants, and contains a set of reagents and protocols that may be used to duplicate our results.

For cloning virus mRNA species, a host cell line sensitive to infection by the virus was infected at 5–10 plaque forming units per cell. When cytopathic effect was evident, but before total destruction, the medium was removed and the cells were lysed in 10 mls lysis buffer (4 M guanidine thiocyanate, 0.1% antifoam A, 25 mM sodium citrate pH 7.0, 0.5% N-lauroyl sarcosine, 0.1 M beta-mercaptoethanol). The cell lysate was poured into a sterilized Dounce homogenizer and homogenized on ice 8–10 times until the solution was homogenous. For RNA purification, 8 mls of cell lysate were gently layered over 3.5 mls of CsCl solution (5.7 M CsCl, 25 mM sodium citrate pH 7.0) in a Beckman SW41 centrifuge tube. The samples were centrifuged for 18 hrs at 20° C. at 36000 rpm in a Beckman SW41 rotor. The tubes were put on ice and the supernatants from the tubes were carefully removed by aspiration to leave the RNA pellet undisturbed. The pellet was resuspended in 400 µl glass distilled water, and 2.6 mls of guanidine solution (7.5 M guanidine-HCl, 25 mM sodium citrate pH 7.0, 5 mM dithiothreitol) were added. Then 0.37 volumes of 1 M acetic acid were added, followed by 0.75 volumes of cold ethanol and the sample was put at −20° C. for 18 hrs to precipitate RNA. The precipitate was collected by centrifugation in a Sorvall centrifuge for 10 min at 4° C. at 10000 rpm in an SS34 rotor. The pellet was dissolved in 1.0 ml distilled water, recentrifuged at 13000 rpm, and the supernatant saved. RNA was re-extracted from the pellet 2 more times as above with 0.5 ml distilled water, and the supernatants were pooled. A 0.1 volume of 2 M potassium acetate solution was added to the sample followed by 2 volumes of cold ethanol and the sample was put at −20° C. for 18 hrs. The precipitated RNA was collected by centrifugation in the SS34 rotor at 4° C. for 10 min at 10000 rpm. The pellet was dissolved in 1 ml distilled water and the concentration taken by adsorption at A260/280. The RNA was stored at −70° C.

mRNA containing polyadenylate tails (poly-A) was selected using oligo-dT cellulose (Pharmacia #27 5543-0). Three mg of total RNA was boiled and chilled and applied to a 100 mg oligo-dT cellulose column in binding buffer (0.1 M Tris pH 7.5, 0.5 M LiCl, 5 mM EDTA pH 8.0, 0.1% lithium dodecyl sulfate). The retained poly-A+ RNA was eluted from the column with elution buffer (5 mM Tris pH 7.5, 1 mM EDTA pH 8.0, 0.1% sodium dodecyl sulfate). This mRNA was reapplied to an oligo-dT column in binding buffer and eluted again in elution buffer. The sample was precipitated with 200 mM sodium acetate and 2 volumes cold ethanol at −20° C. for 18 hrs. The RNA was resuspended in 50 µl distilled water.

Ten µg poly-A+ RNA was denatured in 20 mM methyl mercury hydroxide for 6 min at 22° C. β-mercaptoethanol was added to 75 mM and the sample was incubated for 5 min at 22° C. The reaction mixture for first strand cDNA synthesis in 0.25 ml contained 1 µg oligo-dT primer (P-L Biochemicals) or 1 µg synthetic primer, 28 units placental ribonuclease inhibitor (Bethesda Research Labs #5518SA), 100 mM Tris pH 8.3, 140 mM KCl, 10 mM MgCl2, 0.8 mM dATP, dCTP, dGTP, and dTTP (Pharmacia), 100 microcuries 32P-labeled dCTP (New England Nuclear #NEG-013H), and 180 units AMV reverse transcriptase (Molecular Genetics Resources #MG 101). The reaction was incubated at 42° C. for 90 min, and then was terminated with 20 mM EDTA pH 8.0. The sample was extracted with an equal volume of phenol/chloroform (1:1) and precipitated with 2 M ammonium acetate and 2 volumes of cold ethanol −20° C. for 3 hrs. After precipitation and centrifugation, the pellet was dissolved in 100 µl distilled water. The sample was loaded onto a 15 ml SEPHADEX G-100 (Pharmacia, Inc. Piscataway, N.J.) Gel filtration media; fractionation range for globular proteins 4,000 to 1000,000 daltons in buffer (100 mM Tris pH 7.5, 1 mM EDTA pH 8.0, 100 mM NaCl). The leading edge of the eluted DNA fractions were pooled, and DNA was concentrated by lyophilization until the volume was about 100 μl, then the DNA was precipitated with ammonium acetate plus ethanol as above.

The entire first strand sample was used for second strand reaction which followed the Gubler and Hoffman (1983) method except that 50 μg/ml dNTP's, 5.4 units DNA polymerase I (Boerhinger Mannheim #642-711), and 100 units/ml *E. coli* DNA ligase (New England Biolabs #205) in a total volume of 50 microliters were used. After second strand synthesis, the cDNA was phenol/chloroform extracted and precipitated. The DNA was resuspended in 10 μl distilled water, treated with 1 μg RNase A for 10 min at 22° C., and electrophoresed through a 1% agarose gel (Sigma Type II agarose) in 40 mM Tris-acetate buffer pH 6.85. The gel was strained with ethidium bromide, and DNA in the expected size range was excised from the gel and electroeluted in 8 mM Tris-acetate pH 6.85. Electroeluted DNA was lyophilized to about 100 microliters, and precipitated with ammonium acetate and ethanol as above. The DNA was resuspended in 20 μl water.

Oligo-dC tails were added to the DNA to facilitate cloning. The reaction contained the DNA, 100 mM potassium cacodylate pH 7.2, 0.2 mM dithiothreitol, 2 mM $CaCl_2$, 80 μmoles dCTP, and 25 units terminal deoxynucleotidyl transferase (Molecular Genetic Resources #S1001) in 50 μl. After 30 min at 37° C., the reaction was terminated with 10 mM EDTA, and the sample was phenol/chloroform extracted and precipitated as above.

The dC-tailed DNA sample was annealed to 200 ng plasmid vector pBR322 that contained oligo-dG tails (Bethesda Research Labs #5355 SA/SB) in 200 μl of 0.01 M Tris pH 7.5, 0.1 M NaCl, 1 mM EDTA pH 8.0 at 65° C. for 2 min and then 57° C. for 2 hrs. Fresh competent *E. coli*

DH-1 cells were prepared and transformed as described by Hanahan (1983) using half the annealed cDNA sample in twenty 200 μl aliquots of cells. Transformed cells were plated on L-broth agar plates plus 10 μg/ml tetracycline. Colonies were screened for the presence of inserts into the ampicillin gene using AMPSCREEN (Life Technologies, Inc. Gaethersburg, Md.) Ampicillin resistance screening disks, and the positive colonies were picked for analysis.

Homologous Recombination Procedure for Generating Recombinant FPV

This method relies upon the homologous recombination between FPV DNA and the plasmid homology vector DNA which occurs in the tissue culture cells containing both FPV DNA and transfected plasmid homology vector. For homologous recombination to occur, monolayers of CEF cells are infected with S-FPV-001 (A mild fowlpox vaccine strain available as BIOPOX, a mild fowlpox vaccine strain from Agri-Bio Corporation, Gainsville, Ga.) at a multiplicity of infection of 0.01 PFU/cell to introduce replicating FPV (i.e. DNA synthesis) into the cells. The plasmid homology vector DNA is then transfected into these cells according to the "Infection-Transfection Procedure".

Infection-Transfection Procedure

CEF cells in 6 cm plates (about 80% confluent) were infected with S-FPV-001 at a multiplicity of infection of 0.01 PFU/cell in CEF negative medium and incubated at 37° C. in a humidified 5% $CO_2$ incubator for five hours. The transfection procedure used is essentially that recommended for LIPOFECTIN (Life Technologies, Inc. Gaithersburg, Md.) 1:1 (w/w) liposome formulation of cationic lipid N-[1-(2,3-dioleyoxy)propyl]-N,N,N-trimethylammonium chloride (DOTMA) and dioleoyl phosphatidylethanolamine (DOPE). Briefly, for each 6 cm plate, 15 micrograms of plasmid DNA were diluted up to 100 microliters with $H_2O$. Separately, 50 micrograms of LIPOFECTIN (Life Technologies, Inc. Gaithersburg, Md.) 1:1 (w/w) liposome formulation of cationic lipid N-[1-(2,3-dioleyoxy)propyl]-N,N,N-trimethylammonium chloride (DOTMA) and dioleoyl phosphatidylethanolamine (DOPE) were diluted to 100 microliters with $H_2O$. The 100 microliters of diluted LIPOFECTIN (Life Technologies, Inc. Gaithersburg, Md.) 1:1 (w/w) liposome formulation of cationic lipid N-[1-(2,3-dioleyoxy)propyl]-N,N,N-trimethylammonium chloride (DOTMA) and dioleoyl phosphatidylethanolamine (DOPE) were added dropwise to the diluted plasmid DNA contained in a polystyrene, 5 ml, snap cap tube and mixed gently. The mixture was then incubated for 15–20 minutes at room temperature. During this time, the virus inoculum was removed from the 6 cm plates and the cell monolayers washed once with CEF negative medium. Three mls of CEF negative medium were added to the plasmid DNA/lipofectin mixture and the contents pipetted onto the cell monolayer. Following overnight (about 16 hours) incubation at 37° C. in a humidified 5% $CO_2$ incubator, the medium was removed and replaced with 5 ml CEF complete medium. The cells were incubated at 37° C. in 5% $CO_2$ for 3–7 days until cytopathic effect from the virus was 80–100%. Virus was harvested as described above for the preparation of virus stocks. This stock was referred to as a transfection stock and was subsequently screened for recombinant virus by the "Plaque Hybridization Procedure For Purifying Recombinant FPV".

Plaque Hybridization Procedure for Purifying Recombinant FPV

CEF cell monolayers were infected with various dilutions of the infection/transfection viral stocks, overlaid with nutrient agarose media (equal volumes of 1.2%–1.4% agarose and 2×M199) and incubated 6–7 days for plaque development to occur. The agarose overlay and plate were marked with the same three asymmetrical dots (India ink) to aid in positioning the Nitrocellulose (NC) membrane (cell monolayer) and agarose overlay. The agarose overlay was transferred to the lid of the 10 cm dish and stored at 4° C. The CEF monolayer was overlaid with a pre-wetted (PBS) NC membrane and pressure applied to transfer the monolayer to the NC membrane. Cells contained on the NC membrane were then lysed by placing the membranes in 1.5 ml of 1.5 M NaCl and 0.5 M NaOH for five minutes. The membranes were placed in 1.5 ml of 3 M sodium acetate (pH 5.2) for five minutes. DNA from the lysed cells was bound to the NC membrane by baking at 80° C. for one hour. After this period the membranes were prehybridized with a solution containing 6× SSC, 3% skim milk, 0.5% SDS, salmon sperm DNA (50 μg/ml) and incubated at 65° C. for one hour. Radio-labeled probe DNA (alpha$^{32}$P-dCTP) was added and incubated at 65° C. overnight (12 hours). After hybridization the NC membranes were washed two times (30 minutes each) with 2× SSC at 65° C., followed by two additional washes at 65° C. with 0.5× SSC. The NC membranes were dried and exposed to X-ray film (Kodak X-OMAT, AR) at −70° C. for 12 hours. Plaques corresponding to positive signals seen on the autoradiogram were picked from the agarose overlay, using a pasteur pipette, and were resuspended into 1 ml of CEF media and stored at −70° C. Typically, 5–6 rounds of plaque purification were required to ensure purity of the recombinant virus.

Screen for Foreign Gene Expression in Recombinant FPV using Black Plaque Assays

To analyze expression of foreign antigens expressed by recombinant fowlpox viruses, monolayers of CEF cells were infected with recombinant FPV, overlaid with nutrient agarose media and incubated for 6–7 days at 37° C. for plaque development to occur. The agarose overlay was removed from the dish, the cells fixed with 100% methanol for 10 minutes at room temperature and air dried. The primary antibody was diluted to an appropriate concentration with PBS and incubated on the cell monolayer for two hours at room temperature. Unbound antibody was removed from the cells by washing three times with PBS at room temperature. A horseradish peroxidase conjugated secondary antibody was diluted with PBS and incubated on the cell monolayer for two hours at room temperature. Unbound secondary antibody was then removed by washing the cells three times with PBS at room temperature. The cells were incubated 15–30 minutes at room temperature with freshly prepared substrate solution (100 μg/ml 4-chloro-1-naphthol, 0.003% $H_2O_2$ in PBS). Plaques expressing the correct antigen stain black.

Screen for Recombinant FPV Expressing Enzymatic Marker Genes

When the *E. coli* β-galactosidase (lacZ) or β-glucuronidase (uidA) marker gene was incorporated into a recombinant virus the plaques containing recombinants were visualized by a simple assay. The enzymatic substrate was incorporated (300 μg/ml) into the agarose overlay during the plaque assay. For the lacZ marker gene the substrates BLUOGAL (halogenated indolyl-β-D-galactoside (Life Technologies, Inc. Gaithersburg, Md.) for blue plaques or CPRG (chlorophenol Red Galactopyranoside, Boehringer mannheim) for red plaques were used. For the uidA marker gene the substrate X-Glucuro Chx (5-bromo-4-chloro-3-indolyl-β-D-glucuronic acid Cyclohexylammonium salt, Biosynth AG) was used. Plaques that expressed active marker enzyme turned either red or blue. The plaques were then picked onto fresh cells and purified by further plaque isolation.

RNA Isolated from Concanavalin A Stimulated Chicken Spleen Cells

Chicken spleens were dissected from 3 week old SPAFAS hatched chicks, washed, and disrupted through a syringe/needle to release cells. After allowing stroma and debri to settle out, the cells were pelleted and washed twice with PBS. The cell pellet was treated with a hypotonic lysis buffer to lyse red blood cells, and splenocytes were recovered and washed twice with PBS. Splenocytes were resuspended at $5\times106$ cells/ml in RPMI containing 5% FBS and 5 µg/ml Concanavalin A and incubated at 39° for 48 hours. Total RNA was isolated from the cells using guanidine isothionate lysis reagents and protocols from the Promega RNA isolation kit (Promega Corporation, Madison Wis.). 4 µg of total RNA was used in each 1st strand reaction containing the appropriate antisense primers and AMV reverse transcriptase (Promega Corporation, Madison Wis.). cDNA synthesis was performed in the same tube following the reverse transcriptase reaction, using the appropriate sense primers and VENT DNA polymerase (New England Biolabs, Inc. Beverly, Mass.) DNA polymerase from archaea *Thermococcus litoralis*.

Homology Vector 451-79.95

The plasmid 451-79.95 was constructed for the purpose of inserting the NDV HN gene into FPV. A lacZ marker gene followed by the NDV HN gene was inserted as a cassette into the homology vector 443-88.14 at the unique SfiI site. The cassette may be constructed utilizing standard recombinant DNA techniques (Maniatis et al., 1982 and Sambrook et al., 1989), by joining restriction fragments from the following sources with the synthetic DNA sequences indicated. The first fragment is the synthetic late promoter LP1 (SEQ ID NO:9). The second fragment contains the coding region of *E. coli* lacZ and is derived from plasmid pJF751 (Ferrari et al., 1985). Note that the promoter and lacZ gene are fused so as to express a hybrid protein consisting of 4 amino acids derived from the synthetic promoter followed by amino acids 10 to 1024 of the lacZ gene. The third fragment is another copy of the synthetic late promoter LP1. the fourth fragment contains the coding region of the NDV HN gene and was derived from the full length HN cDNA clone. Note that the promoter and HN gene are fused so as to express a hybrid protein consisting of 4 amino acids derived from the synthetic promoter followed by amino acids 2 to 577 of the HN gene. Both genes are in the opposite transcriptional orientation relative to the ORF1 gene in the parental homology vector.

Homology Vector 489-21.1

The plasmid 489-21.1 was constructed for the purpose of inserting the NDV HN gene into FPV. The NDV HN gene was inserted as a cassette into the homology vector 443-88.8 at the unique SfiI site. The cassette may be constructed utilizing standard recombinant DNA techniques (Maniatis et al., 1982 and Sambrook et al., 1989), by joining restriction fragments from the following sources with the synthetic DNA sequences indicated. The first fragment is the synthetic early/late promoter EP1LP2 (SEQ ID NO:8/SEQ ID NO:11). The second fragment contains the coding region of the NDV HN gene and was derived from the full length HN cDNA clone. Note that the promoter and HN gene are fused so as to express a hybrid protein consisting of 4 amino acids derived from the synthetic promoter followed by amino acids 2 to 577 of the HN gene. The HN gene is in the opposite transcriptional orientation relative to the ORF in the parental homology vector.

Homology Vectors 502-26.22

Figure 1B:
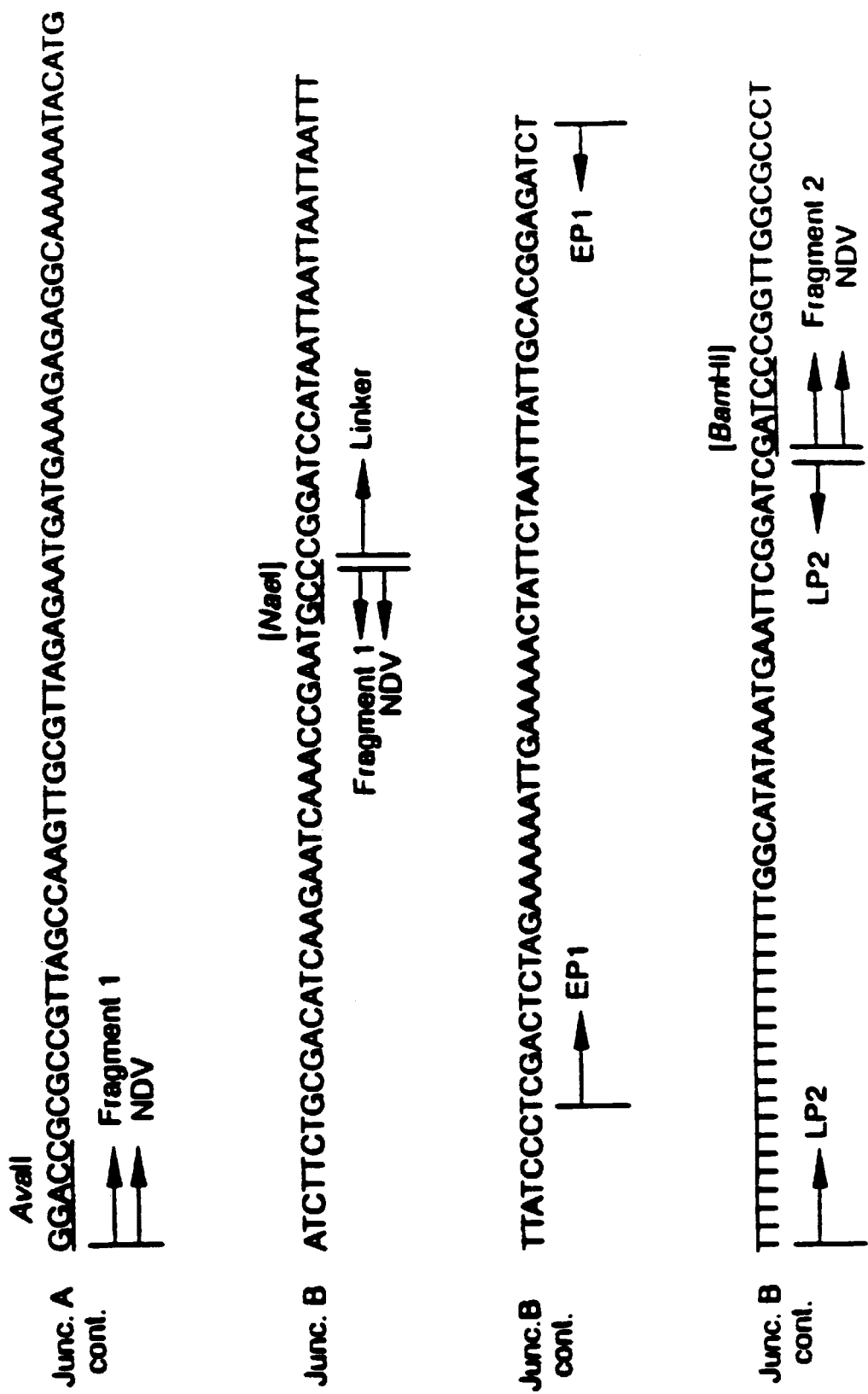
FIGS. 1A–1C: Detailed description of the SfiI fragment insert in Homology Vector 502-26.22. The diagram shows the orientation of DNA fragments assembled in the cassette. The origin of each fragment is described in the Materials and Methods section. The sequences located at the junctions between each fragment and at the ends of the marker gene are shown, including junction A (SEQ ID NO: 15), junction B (SEQ ID NO: 16), junction C (SEQ ID NO: 17), and junction D (SEQ ID NO: 18). The restriction sites used to generate each fragment are indicated at the appropriate junction. The location of the NDV F and HN genes is shown.

The plasmid 502-26.22 was constructed for the purpose of inserting the NDV HN and F genes into FPV. The NDV HN and F genes were inserted as a SfiI fragment (SEQ ID NO:12) into the homology vector 443-88.8 at the unique SfiI site. The NDV HN and F genes were inserted in the same transcriptional orientation as the ORF in the parental homology vector. A detailed description of the SfiI is shown in FIGS. 1A–1C. The inserted SfiI fragment may be constructed utilizing standard recombinant DNA techniques (Maniatis et al. and Sambrook et al., 1989), by joining restriction fragments from the following sources with the synthetic DNA sequences indicated in FIGS. 1A–1C. Fragment 1 is approximately 1811 base pair AvaII to NaeI restriction fragment of the full length NDV HN cDNA clone (B1 strain). Fragment 2 is an approximately 1812 base pair BamHI to PstI restriction fragment of the full length NDV F CDNA (B1 strain). Fragment 3 is an approximately 235 base pair PstI and ScaI restriction fragment of the plasmid pBR322.

Homology Vector 502-27.5

The plasmid 502-27.5 was constructed for the purpose of inserting the NDV F gene into FPV. A LacZ marker gene followed by the NDV F gene was inserted as a cassette into the homology vector 443-88.14 at the unique SfiI site. The cassette may be constructed utilizing standard recombinant DNA techniques (Maniatis et al., 1982 and Sambrook et al., 1989), joining restriction fragments from the following sources with the synthetic DNA sequences indicated. The first fragment is the synthetic late promoter LP1 (SEQ ID NO:9). The second fragment contains the coding region of *E. coli* LacZ and is derived from plasmid pJF751 (Ferrari et al., 1985). Note that the promoter and LacZ gene are fused so as to express a hybrid protein consisting of 4 amino acids derived from the synthetic promoter followed by amino acids 10 to 1024 of the LacZ gene. The third fragment is the synthetic early/late promoter EP1LP2 (SEQ ID NO:8/SEQ ID NO:11). The fourth fragment contains the coding region of the NDV F gene and was derived from the full length F cDNA clone. Note that the promoter and F gene are fused so as to express a hybrid protein consisting of 4 amino acids derived from the synthetic promoter followed by 10 amino acids derived from the F gene 5' untranslated region followed by amino acid 1 to 544 of the F gene. Both genes are in the opposite transcriptional orientation relative to the ORF in the parental homology vector.

Homology Vector 586-36.6

The plasmid 586-36.6 was constructed for the purpose of inserting the infectious laryngotracheitis virus (ILT) gB and gD genes into the FPV. An *E. coli* β-glucuronidase uidA marker gene preceeded by the ILT gB and gD genes was inserted as a cassette into the homology vector 451-08.22 at the unique SfiI site. The cassette may be constructed utilizing standard recombinant DNA techniques (Maniatis et al., 1982 and Sambrook et al., 1989), by joining restriction fragments from the following sources with the synthetic DNA sequences indicated. The first fragment is the synthetic early/late promoter EP1LP2 (SEQ ID NO:8/SEQ ID NO:11). The second fragment contains the coding region of ILT gB and is derived from an approximately 3000 base pair ILT virus genomic EcoRI fragment. Note that the promoter and gB gene are fused so as to express the complete coding region of the gB gene (amino acids 1–883). The third fragment is the synthetic early/late promoter EP1LP2 (SEQ ID NO:8/SEQ ID NO:11). The fourth fragment contains the coding region of the ILT gD gene (SEQ ID NO:19) and was derived from an approximately 2060 base pair EcoRI to BclI restriction sub-fragment of the ILT KpnI genomic restriction fragment #8 (10.6 KB). Note that the promoter and gD gene are fused so as to express a hybrid protein consisting of 3 amino acids derived from the synthetic promoter followed by amino acids 3 to 434 of the gD gene. The fifth fragment is the synthetic late promoter LP1 (SEQ ID NO:9). The last fragment contains the coding region of E. coli uidA and is derived from plasmid pRAJ260 (Clonetech). Note that the promoter and uidA gene are fused so as to express a hybrid protein consisting of 3 amino acids derived from the synthetic promoter followed by amino acids 1 to 602 of the uidA gene. All three genes are in the opposite transcriptional orientation relative to ORF1 in the parental homology vector.

Homology Vector 608-10.3

The plasmid 608-10.3 was constructed for the purpose of inserting the Marek's Disease virus (MDV) gD and gB genes into FPV. A LacZ marker gene preceeded by the MDV gD and gB genes was inserted as a cassette into the homology vector 443-88.14 at the unique sfiI site. The cassette may be constructed utilizing standard recombinant DNA techniques (Maniatis et al., 1982 and Sambrook et al., 1989), by joining restriction fragments from the following sources with the synthetic DNA sequences indicated. The first fragment is the synthetic late/early promoter LP2EP2 (SEQ ID NO:11/SEQ ID NO:10). The second fragment contains the coding region of MDV gD and is derived from an approximately 2177 base pair NcoI to SalI sub-fragment of the MDV BglII 4.2 KB genomic restriction fragment (Ross, et al., 1991). Note that the promoter and gD are fused so as to express a hybrid protein consisting of 3 amino acids derived from the synthetic promoter followed by amino acids 3 to 403 of the gD gene. The third fragment is the synthetic early/late promoter EP1LP2 (SEQ ID NO:8/SEQ ID NO:11). The fourth fragment contains the coding region of the MDV gB gene and was derived from an approximately 3898 base pair SalI to EcoRI genomic MDV fragment (Ross, et al., 1989). Note that the promoter and gB gene are fused so as to express a hybrid protein consisting of 3 amino acids derived from the synthetic promoter followed by amino acids 3 to 865 of the gB gene. The fifth fragment is the synthetic late promoter LP1 (SEQ ID NO:9). The sixth fragment contains the coding region of E. coli LacZ and is derived from plasmid pJF751 (Ferrari, et al., 1985). Note that the promoter and LacZ gene are fused so as to express a hybrid protein consisting of 4 amino acids derived from the synthetic promoter followed by amino acids 10 to 1024 of the LacZ gene. All three genes are in the opposite transcriptional orientation relative to ORF1 in the parental homology vector.

Homology Vector 538-51.27

The plasmid 538-51.27 was constructed for the purpose of inserting the genes for Infectious Bronchitis virus (IBV) Massachusetts Spike protein (Mass Spike) and Massachusetts Matrix protein (Mass Matrix) into FPV. A lacz marker gene and the genes for IBV Mass Spike and Mass Matrix were inserted as a cassette into the homology vector 443-88.14 at the unique SfiI site. The inserted SfiI fragment is constructed utilizing standard recombinant DNA techniques (Maniatis et al., 1982 and Sambrook et al., 1989), by joining restriction fragments from the following sources. The first fragment is the synthetic early/late promoter EP1LP2 (SEQ ID NO: 8/ SEQ ID NO: 11). The second fragment contains the coding region for the IBV Mass Spike gene and (amino acids 3–1162) is derived from an approximately 3500 base pair BsmI to PvuI IBV cDNA fragment. The third fragment is the synthetic early/late promoter EP1LP2 (SEQ ID NO: 8/ SEQ ID NO: 11). The fourth fragment contains the coding region for the IBV Mass Matrix gene (amino acids 1–232) and is derived from an approximately 1500 base pair XbaI to SpeI IBV cDNA fragment. The fifth fragment is the synthetic late promoter LP1 (SEQ ID NO: 9). The sixth fragment contains the coding region of E. coli lacZ and is derived from plasmid pJF751 (Ferrari, et al. 1985).

Homology Vector 622-49.1

The plasmid 622-49.1 was constructed for the purpose of inserting the IBV Massachusetts (Mass) Nucleocapsid gene into FPV. A uidA marker gene and the IEV Mass Nucleocapsid gene was inserted as a cassette into the homology vector 451-08.22 at the unique Sfi1 site. The inserted SfiI fragment was constructed utilizing standard recombinant DNA techniques (Maniatis et al., 1982 and Sambrook et al., 1989), by joining restriction fragments from the following sources. The first fragment is the synthetic early/late promoter EP1LP2 (SEQ ID NO: 8/ SEQ ID NO: 11). The second fragment contains the coding region for the IBV Mass Nucleocapsid gene and is derived from an approximately 3800 base pair PstI to IBV cDNA fragment. The third fragment is the synthetic late promoter LP1 (SEQ ID NO: 9). The fourth fragment contains the coding region of E. coli uidA and is derived from plasmid pRAJ260 (Clonetech).

Homology Vectors 584-36.12

The plasmid 584-36.12 was constructed for the purpose of inserting the NDV HN and F genes into FPV. The NDV HN and F genes were inserted as a SfiI fragment into the homology vector 443-88.14 (see example 1B) at the unique SfiI site. The NDV HN and F genes were inserted in the same transcriptional orientation as the ORF in the parental homology vector. A detailed description of the SfiI fragment is shown in FIGS. 1A–1C. The inserted SfiI fragment was constructed utilizing standard recombinant DNA techniques (Maniatis et al, 1982 and Sambrook et al, 1989), by joining restriction fragments from the following sources with the synthetic DNA sequences indicated in FIGS. 1A–1C. Fragment 1 is an approximately 1811 base pair AvaII to NaeI restriction fragment of the full length NDV HN cDNA clone (B1 strain). Fragment 2 is an approximately 1812 base pair BamHI to PstI restriction fragment of the full length NDV F cDNA (B1 strain). Fragment 3 is an approximately 235 base pair PstI to ScaI restriction fragment of the plasmid pBR322.

Homology Vector 694-10.4

The plasmid 694-10.4 was constructed for the purpose of inserting the infectious laryngotracheitis virus (ILTV) gB and gD genes into FPV. An E.coli β-glucuronidase uidA marker gene preceded by the ILTV gB and gD genes was inserted as a cassette into the homology vector 451-08.22 at the unique SfiI site. The cassette was constructed utilizing standard recombinant DNA techniques (Maniatis et al, 1982 and Sambrook et al, 1989), by joining restriction fragments from the following sources with the synthetic DNA sequences indicated. The first fragment is the synthetic early/late promoter EP1LP2 (SEQ ID NO:8/SEQ ID NO:11)

The second fragment contains the coding region of ILTV gB and is derived from an approximately 3000 base pair ILT virus genomic EcoRI fragment. Note that the promoter and gB gene are fused so as to express the complete coding region of the gB gene (amino acids 1–883). The third fragment is the synthetic early/late promoter EP1LP2 (SEQ ID NO:8/SEQ ID NO:11). The fourth fragment contains the coding region of the ILTV gD gene and was derived from an approximately 2060 base pair EcoRI to BclI restriction sub-fragment of the ILTV KpnI genomic restriction fragment #8 (10.6 KB). Note that the promoter and gD gene are fused so as to express a hybrid protein consisting of 3 amino acids derived from the synthetic promoter followed by amino acids 3 to 434 of the gD gene. The fifth fragment is the synthetic late promoter LP1 (SEQ ID NO:9). The last fragment contains the coding region of E.coli uidA and is derived from plasmid pRAJ260 (Clonetech). Note that the promoter and uidA gene are fused so as to express a hybrid protein consisting of 3 amino acids derived from the synthetic promoter followed by amino acids 1 to 602 of the uidA gene.

Homology Vector 749-75.82

The plasmid 749-75.82 was used to insert foreign DNA into FPV. It incorporates an E. coli β-galactosidase (lacZ) marker gene and the infectious bursal disease virus (IBDV) polymerase gene flanked by FPV DNA. When this plasmid was used according to the HOMOLOGOUS RECOMBINATION PROCEDURE FOR GENERATING RECOMBINANT FPV a virus containing DNA coding for the foreign genes results. Note that the β-galactosidase (lacZ) marker gene is under the control of a synthetic late pox promoter (LP1) and the IBDV polymerase gene is under the control of a synthetic late/early pox promoter (LP2EP2). The homology vector was constructed utilizing standard recombinant DNA techniques (11 and 14), by joining restriction fragments from the following sources with the appropriate synthetic DNA sequences. The plasmid vector was derived from an approximately 2999 base pair EcoRI restriction fragment of pSP64 (Promega). Fragment 1 is an approximately 1184 base pair EcoRI to SnaBI restriction subfragment of the 2.8 kb EcoRI FPV genomic fragment (SEQ ID NO. 5). Fragment 2 is an approximately 2700 EcoRI to AscI restriction fragment synthesized by cDNA cloning and polymerase chain reaction (PCR) from an IBDV RNA template. cDNA and PCR primers (5'-CAC GAATTCTGACATTTTCAACAGTCCACAGGCGC-3'; 12/93.4) (SEQ ID NO: 22) and 5'-GCTGTTGGACAT CACGGGCCAGG-3'; 9/93.28) (SEQ ID NO: 23) were used to synthesize an approximately 1100 base pair EcoRI to BclI fragment at the 5' end of the IBDV polymerase gene. cDNA and PCR primers (5'-ACCCGGAACATATGGTCA GCTCCAT-3'; 12/93.2) (SEQ ID NO: 24) and 5'-GGCGCGCCAGGCGAAGGCCGGGGATACGG-3'; 12/93.3) (SEQ ID NO: 25) were used to synthesize an approximately 1700 base pair BclI to AscI fragment at the 3' end of the IBDV polymerase gene. The two fragments were ligated at the BclI site to form the approximately 2800 base pair EcoRI to BclI fragment. Fragment 3 is an approximately 3002 base pair BamHI to PvuII restriction fragment of plasmid pJF751 (7). Fragment 4 is an approximately 1626 base pair SnaBI to EcoRI restriction sub-fragment of the 2.8 kb EcoRI FPV genomic fragment (SEQ ID NO. 5).

Homology Vector 751-07. D1

The plasmid 751-07.D1 was used to insert foreign DNA into FPV. It incorporates an *E. coli* β-galactosidase (lacZ) marker gene and the chicken interferon (cIFN) gene flanked by FPV DNA. When this plasmid was used according to the HOMOLOGOUS RECOMBINATION PROCEDURE FOR GENERATING RECOMBINANT FPV a virus containing DNA coding for the foreign genes results. Note that the β-galactosidase (lacZ) marker gene is under the control of a synthetic late pox promoter (LP1) and the cIFN gene is under the control of a synthetic late/early pox promoter (LP2EP2). The homology vector was constructed utilizing standard recombinant DNA techniques (17), by joining restriction fragments from the following sources with the appropriate synthetic DNA sequences. The plasmid vector was derived from an approximately 2999 base pair EcoRI restriction fragment of pSP64 (Promega). Fragment 1 is an approximately 1626 base pair EcoRI to SnaBI restriction sub-fragment of the 2.8 kb EcoRI FPV genomic fragment (SEQ ID NO. 5). Fragment 2 is an approximately 577 base pair EcoRI to BglII fragment coding for the cIFN gene (17) derived by reverse transcription and polymerase chain reaction (PCR) (Sambrook, et al., 1989) of RNA ISOLATED FROM CONCANAVALIN A STIMULATED CHICKEN SPLEEN CELLS. The antisense primer (6/94.13) used for reverse transcription and PCR was 5'CGACGGATCCGAGGTGCGTTTGGGGCTAAGTGC-3' (SEQ ID NO: 26). The sense primer (6/94.12) used for PCR was 5'CCACGGATCCAGCACAACGCG AGTCCCACCATGGCT-3' (SEQ ID NO: 27). The BamHI fragment resulting from reverse transcription and PCR was gel purified and used as a template for a second PCR reaction to introduce a unique EcoRI site at the 5' end and a unique BglII site at the 3' end. The second PCR reaction used primer 6/94.22 (5'CCACGAATTCGATGGCTGTGC CTGCAAGCCCACAG-3'; SEQ ID NO: 28) at the 5' end and primer 6/94.34 (5'-CGAAGATCTGAGGTGCGTTTG GGGCTAAGTGC-3'; SEQ ID NO: 29) at the 3' end to yield an approximately 577 base pair fragment. The DNA fragment contains the coding sequence from amino acid 1 to amino acid 193 of the chicken interferon protein (17) which includes a 31 amino acid signal sequence at the amino terminus and 162 amino acids of the mature protein encoding chicken interferon. Fragment 3 is an approximately 3002 base pair BamHI to PvuII restriction fragment of plasmid pJF751 (7). Fragment 4 is an approximately 1184 base pair SnaBI to EcoRI restriction sub-fragment of the 2.8 kb EcoRI FPV genomic fragment (SEQ ID NO. 5).

Homology Vector 751-56.C1

The plasmid 751-56.C1 was used to insert foreign DNA into FPV. It incorporates an *E. coli* β-galactosidase (lacZ) marker gene and the chicken myelomonocytic growth factor (cMGF) gene flanked by FPV DNA. When this plasmid was used according to the HOMOLOGOUS RECOMBINATION PROCEDURE FOR GENERATING RECOMBINANT FPV a virus containing DNA coding for the foreign genes results. Note that the β-galactosidase (lacZ) marker gene is under the control of a synthetic late pox promoter (LP1) and the cMGF gene is under the control of a synthetic late/early pox promoter (LP2EP2). The homology vector was constructed utilizing standard recombinant DNA techniques (11 and 14), by joining restriction fragments from the following sources with the appropriate synthetic DNA sequences. The plasmid vector was derived from an approximately 2999 base pair EcoRI restriction fragment of pSP64 (Promega). Fragment 1 is an approximately 1184 base pair EcoRI to SnaBI restriction sub-fragment of the 2.8 kb EcoRI FPV genomic fragment (SEQ ID NO. 5). Fragment 2 is an approximately 640 base pair EcoRI to BamHI fragment coding for the cMGF gene (16) derived by reverse transcription and polymerase chain reaction (PCR) (Sambrook, et al., 1989) of RNA ISOLATED FROM CONCANAVALIN A STIMULATED CHICKEN SPLEEN CELLS. The antisense primer (6/94.20) used for reverse transcription and PCR was 5' CGCAGGATCCGGGGCGTCAGA GGCGGGCGAGGTG-3' (SEQ ID NO: 30). The sense primer (5/94.5) used for PCR was 5' GAGCGGATCCTG-CAGGAGGAG ACACAGAGCTG-3' (SEQ ID NO: 31). The BamHI fragment derived from PCR was subcloned into a plasmid and used as a template for a second PCR reaction using primer 6/94.16 (5'-GCGCGAATTCCATGTGCT GCCTCACCCCTGTG 3'; SEQ ID NO: 32) at the 5' end and primer 6/94.20 (5' CGCAGGATCCGGGGCGTCAGA GGCGGGCGAGGTG-3'; SEQ ID NO: 30) at the 3' end to yield an approximately 640 base pair fragment. The DNA fragment contains the coding sequence from amino acid 1 to amino acid 201 of the cMGF protein (16) which includes a 23 amino acid signal sequence at the amino terminus and 178 amino acids of the mature protein encoding cMGF. Fragment 3 is an approximately 3002 base pair BamHI to PvuII restriction fragment of plasmid pJF751 (7). Fragment 4 is an approximately 1626 base pair SnaBI to EcoRI restriction sub-fragment of the 2.8 kb EcoRI FPV genomic fragment (SEQ ID NO. 5).

EXAMPLE 1
Sites for Insertion of Foreign DNA into FPV

In order to define appropriate insertion sites, a library of FPV EcoRI restriction fragments was generated in the plasmid vector pSP64 (Promega). Several of these restriction fragments were subjected to restriction mapping analysis. Unique blunt cutting restriction endonuclease sites were identified and mapped within the cloned FPV DNA regions. The blunt restriction sites were converted to Not I and Sfi I sites through the use of synthetic DNA linkers (oligo 66.04; 5'-GGCGGCCGCGGCCCTCGAGGCCA-3' SEQ ID NO: 33 and oligo 66.05; 5' TGGCCTCGAGGGCCGCGGC-CGCC 3' SEQ ID NO: 34). A β-galactosidase (lacZ) marker gene was inserted in each of the potential sites. A plasmid containing such a foreign DNA insert may be used according to the HOMOLOGOUS RECOMBINATION PROCEDURE FOR GENERATING RECOMBINANT FPV to construct a FPV containing the foreign DNA. For this procedure to be successful it is important that the insertion site be in a region non-essential to the replication of the FPV and that the site be flanked with FPV DNA appropriate for mediating homologous recombination between virus and plasmid DNAs. The plasmids containing the lacZ marker gene were utilized in the HOMOLOGOUS RECOMBINATION PROCEDURE FOR GENERATING RECOMBINANT FPV. The generation of recombinant virus was determined by the SCREEN FOR RECOMBINANT FPV EXPRESSING ENZYMATIC MARKER GENES. Three sites were successfully used to generate a recombinant viruses. In each case the resulting virus was easily purified to 100%, clearly defining an appropriate site for the insertion of foreign DNA. The three homology vectors used to define these sites are described below.

EXAMPLE 1A
Homology Vector 443-88.8

The homology vector 443-88.8 contains a 3.5 KB FPV genomic EcoRI fragment and is useful for the insertion of foreign DNA into FPV. This EcoRI fragment maps to the approximately 5.5 KB overlap of FPV genomic fragments SalI C and PstI F (Coupar et al., 1990). The NotI/SfiI linker described above was inserted into a unique HpaI site in this fragment. This site is designated the 680 insertion site.

The homology vector 443-88.8 was characterized by DNA sequence analysis. Approximately 1495 base pairs of DNA sequence flanking the HpaI site was determined (SEQ ID NO: 3). This sequence indicates that the open reading frame of 383 amino acids spans the HpaI insertion site. The HpaI site interrupts this ORF at amino acid 226. This ORF shows no amino acid sequence homology to any known pox virus genes.

EXAMPLE 1B
Homology Vector 443-88.14

The homology vector 443-88.14 contains a 2.8 KB FPV genomic EcoRI fragment and is useful for the insertion of foreign DNA into FPV. The NotI/SfiI linker described above was inserted into a unique SnaBI site in this fragment. This site is designated the 681 insertion site.

The homology vector 443-88.14 was characterized by DNA sequence analysis. The entire sequence of the 2.8 KB fragment was determined (SEQ ID NO: 5). This sequence indicates that the SnaBI site is flanked on one side by a complete ORF of 422 amino acids (ORF1) reading toward the restriction site and on the other side by an incomplete ORF of 387 amino acids (ORF2) also reading toward the restriction site. Both ORF1 and ORF2 share homology with the vaccinia virus M1L gene (ref). The M1L gene shares homology with the vaccinia virus K1L gene which has been shown to be involved in viral host-range functions.

EXAMPLE 1C
Homology Vector 451-08.22

The homology vector 451-08.22 contains a 4.2 KB FPV genomic EcoRI fragment and is useful for the insertion of foreign DNA into FPV. The NotI/SfiI linker described above was inserted into a unique StuI site in this fragment. A unique MluI site is located approximately 500 base pairs away from the StuI insertion site. This site is designated the 540 insertion site.

EXAMPLE 2
Bivalent Vaccines Against Newcastle Disease and Fowlpox

Recombinant FPV expressing proteins from NDV make bivalent vaccines protecting against both Marek's Disease and Newcastle disease. We have constructed several recombinant FPV expressing NDV proteins: S-FPV-013 (example 2A), S-FPV-035 (example 2B), S-FPV-041 (example 2C), S-FPV-042 (example 2D), and S-FPV-043 (example 2E).

EXAMPLE 2A
S-FPV-013

S-FPV-013 is a recombinant fowlpox virus that expresses two foreign genes. The gene for *E. coli* β-galactosidase (lacZ gene) and the gene for Newcastle Disease virus hemagglutinin-neuraminidase (HN) protein were inserted into the 681 insertion site. The lacZ gene is under the control of a synthetic late promoter LP1 and the HN gene is under the control of the synthetic late promoter LP2.

S-FPV-013 was derived from S-FPV-001. This was accomplished utilizing the homology vector 451-79.95 (see Materials and Methods) and virus S-FPV-001 in the HOMOLOGOUS RECOMBINATION PROCEDURE FOR GENERATING RECOMBINANT FPV. The transfection stock was screened by the SCREEN FOR RECOMBINANT FPV EXPRESSING ENZYMATIC MARKER GENES. The final result of red plaque purification was the recombinant virus designated S-FPV-013. This virus was assayed for β-galactosidase expression, purity, and insert stability by multiple passages monitored by the blue plaque assay as described in the materials and methods. After the initial three rounds of purification all plaques observed were blue indicating that the virus was pure, stable and expressing the marker gene.

S-FPV-013 was assayed for expression of NDV specific antigens using the BLACK PLAQUE SCREEN FOR FOREIGN GENE EXPRESSION IN RECOMBINANT FPV. An NDV HN specific monoclonal antibody (3-1G-5) was shown to react specifically with S-FPV-013 plaques and not with S-FPV-001 negative control plaques. All S-FPV-013 observed plaques reacted with the monoclonal antibody antiserum indicating that the virus was stably expressing the NDV foreign gene.

EXAMPLE 2B

S-FPV-035

S-FPV-035 is a recombinant fowlpox virus that express a foreign gene. The Newcastle Disease virus HN gene was inserted at the 680 insertion site (see example 1A). The HN gene is under the control of the synthetic early/late promoter EP1LP2.

S-FPV-035 was derived from S-FPV-001. This was accomplished utilizing the homology vector 489-21.1 (see Materials and Methods) and virus S-FPV-001 in the HOMOLOGOUS RECOMBINATION PROCEDURE FOR GENERATING RECOMBINANT FPV. The transfection stock was screened by the PLAQUE HYBRIDIZATION PROCEDURE FOR PURIFYING RECOMBINANT FPV. The final result of plaque hybridization purification was the recombinant virus designated S-FPV-035.

S-FPV-035 was assayed for expression of NDV specific antigens using the BLACK PLAQUE SCREEN FOR FOREIGN GENE EXPRESSION IN RECOMBINANT FPV. An NDV HN specific monoclonal antibody (3-1G-5) was shown to react specifically with S-FPV-035 plaques and not with S-FPV-001 negative control plaques. All S-FPV-035 observed plaques reacted with the monoclonal antibody indicating that the virus was stably expressing the NDV foreign gene.

EXAMPLE 2C

S-FPV-041

S-FPV-041 is a recombinant fowlpox virus that expresses two foreign genes. The gene for $E.\ coli$ β-galactosidase (lacZ gene) and the gene for Newcastle Disease virus fusion (F) protein were inserted into the 681 insertion site. The lacZ gene is under the control of a synthetic late promoter LP1 and the F gene is under the control of the synthetic early/late promoter EP1LP2.

S-FPV-041 was derived from S-FPV-001. This was accomplished utilizing the homology vector 502-27.5 (see Materials and Methods) and virus S-FPV-001 in the HOMOLOGOUS RECOMBINATION PROCEDURE FOR GENERATING RECOMBINANT FPV. The transfection stock was screened by the SCREEN FOR RECOMBINANT FPV EXPRESSING ENZYMATIC MARKER GENES. The final result of red plaque purification was the recombinant virus designated S-FPV-041. This virus was assayed for β-galactosidase expression, purity, and insert stability by multiple passages monitored by the blue plaque assay as described in the materials and methods. After the initial three rounds of purification all plaques observed were blue indicating that the virus was pure, stable and expressing the marker gene.

S-FPV-041 was assayed for expression of NDV specific antigens using the BLACK PLAQUE SCREEN FOR FOREIGN GENE EXPRESSION IN RECOMBINANT FPV. An NDV F specific monoclonal antibody (5-3F-2) was shown to react specifically with S-FPV-041 plaques and not with S-FPV-001 negative control plaques. All S-FPV-041 observed plaques reacted with the monoclonal antibody indicating that the virus was stably expressing the NDV foreign gene.

EXAMPLE 2D

S-FPV-042

S-FPV-042 is a recombinant fowlpox virus that expresses three foreign genes. The gene for $E.\ coli$ β-galactosidase (lacZ gene) and the gene for Newcastle Disease virus fusion (F) protein was inserted into the 681 insertion site. The lacZ gene is under the control of a synthetic late promoter LP1 and the F gene is under the control of the synthetic early/late promoter EP1LP2. The Newcastle Disease virus hemagglutinin (HN) gene were inserted at the 680 insertion site. The HN gene is under the control of the synthetic early/late promoter EP1LP2.

S-FPV-042 was derived from S-FPV-035. This was accomplished utilizing the homology vector 502-27.5 (see Materials and Methods) and virus S-FPV-035 in the HOMOLOGOUS RECOMBINATION PROCEDURE FOR GENERATING RECOMBINANT FPV. The transfection stock was screened by the SCREEN FOR RECOMBINANT FPV EXPRESSING ENZYMATIC MARKER GENES. The final result of red plaque purification was the recombinant virus designated S-FPV-042. This virus was assayed for β-galactosidase expression, purity, and insert stability by multiple passages monitored by the blue plaque assay as described in the materials and methods. After the initial three rounds of purification all plaques observed were blue indicating that the virus was pure, stable and expressing the marker gene.

S-FPV-042 was assayed for expression of NDV specific antigens using the BLACK PLAQUE SCREEN FOR FOREIGN GENE EXPRESSION IN RECOMBINANT FPV. Monoclonal antibodies specific for both HN (3-1G-5) and F (5-3F-2) were shown to react specifically with S-FPV-042 plaques and not with S-FPV-001 negative control plaques. All S-FPV-042 observed plaques reacted with the monoclonal antibodies indicating that the virus was stably expressing the NDV foreign genes.

EXAMPLE 2E

S-FPV-043

S-FPV-043 is a recombinant fowlpox virus that expresses two foreign genes. The genes for Newcastle Disease virus F protein and HN protein were inserted at the 680 insertion site. The F and HN genes are each under the control of a synthetic early/late promoter EP1LP2.

S-FPV-043 was derived from S-FPV-001. This was accomplished utilizing the homology vector 502-26.22 (see Materials and Methods) and virus S-FPV-001 in the HOMOLOGOUS RECOMBINATION PROCEDURE FOR GENERATING RECOMBINANT FPV. The transfection stock was screened by the PLAQUE HYBRIDIZATION PROCEDURE FOR PURIFYING RECOMBINANT FPV. The final result of plaque hybridization purification was the recombinant virus designated S-FPV-043. The S-FPV-043 has been deposited pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. VR 2395.

S-FPV-043 was assayed for expression of NDV specific antigens using the BLACK PLAQUE SCREEN FOR FOREIGN GENE EXPRESSION IN RECOMBINANT FPV. Monoclonal antibodies specific for both HN (3-1G-5) and F (5-3F-2) were shown to react specifically with S-FPV-043 plaques and not with S-FPV-001 negative control plaques. All S-FPV-043 observed plaques reacted with the monoclonal antibodies antiserum indicating that the virus was stably expressing the NDV foreign genes.

Testing of Recombinant FPV Expressing NDV Antigens

Groups of one day old SPF chicks (HyVac Inc.) were immunized with recombinant fowlpox viruses S-FPV-035, S-FPV-041, or S-FPV-043. Non vaccinated controls were also included. Three weeks post-vaccination, the birds were challenged intramuscularly with either virulent NDV or virulent FPV (Table 1). The challenged chicks were observed daily for 14 days for clinical signs and death due to NDV. Non vaccinated control birds showed 100% mortality. S-FPV-043 vaccinated birds showed 100% protection against FPV challenge. Birds vaccinated with S-FPV-035 showed 95% protection compared with 85% seen with birds immunized with S-FPV-041. These results suggest that recombinants expressing HN or F alone provide only partial protection. When both NDV proteins are combined into the same virus S-FPV-043, an enhancement of protection against lethal NDV challenge is obtained, resulting in a lower protective dose. The chicks that were challenged with FPV were scored for pox lesions. Non vaccinated control birds showed no protection against FPV lesions. Birds vaccinated with S-FPV-043 were completely protected from FPV lesions.

The duration of immunity conferred by vaccination with S-FPV-043 was examined. A group of SPF chicks was immunized with S-FPV-043 at one day of age and then challenged six weeks post-vaccination with either NDV or FPV. Complete protection was observed against both NDV and FPV challenge in S-FPV-043 vaccinated birds, whereas non vaccinated controls were totally susceptible to both challenge viruses. These results suggest that the duration of immunity afforded by vaccination with S-FPV-043 would span the life of a broiler bird (~6 weeks).

The effect of vaccinating hens in lay with the recombinant S-FPV-043 was evaluated by assessing egg production post-vaccination. One group of 50 hens was vaccinated and a second group of 50 hens, housed under conditions identical to the vaccinated group, served as non vaccinated controls. Daily egg production was monitored for four weeks post-vaccination. No differences were observed in egg production between the two groups of hens, indicating this vaccine will not adversely affect egg production in laying hens.

A study was conducted to determine whether S-FPV-043 could actively immunize chicks in the presence of maternal antibodies to both NDV and FPV. Chicks obtained from NDV and FPV immunized flocks were vaccinated with S-FPV-043 and three weeks after vaccination, they were challenged with either virulent NDV or virulent FPV. Clinical responses were compared with non vaccinated chicks from the same flock and with non-vaccinated chicks from an antibody negative flock (Table 2). Chicks derived from antibody negative flocks showed 100% mortality after NDV challenge. Protection against NDV challenge, in non-vaccinated chicks known to have maternally derived anti-body against NDV, ranged from 30 to 60%. Protection levels increased, to a range of 75 to 85%, when the maternal antibody positive chicks were vaccinated with S-FPV-043 suggesting an active immunization. The increase in NDV protection from 30% to 75% (flock 1) and 55% to 85% (flock 2) clearly demonstrate the ability of S-FPV-043 to partially overcome maternal antibody to both NDV and FPV. A decrease in FPV protection (90%) was observed in flock 1, suggesting some inhibition of FPV replication.

TABLE 1

Immunity conferred by Fowlpox recombinant vaccines vectoring different genes from Newcastle disease virus

| VIRUS | DOSE[b] | Challenge[a] | |
|---|---|---|---|
| | | NDV | FPV |
| FPV/NDV-HN | 8 × 10^5 | 95 | NT[c] |
| FPV/NDV-F | 2 × 10^4 | 85 | NT |

TABLE 1-continued

Immunity conferred by Fowlpox recombinant vaccines vectoring different genes from Newcastle disease virus

| VIRUS | DOSE[b] | Challenge[a] | |
|---|---|---|---|
| | | NDV | FPV |
| FPV/NDV-HN + F | 2 × 10^3 | 100 | 100 |
| Controls | none | 0 | 0 |

[a]Percent protection following challenge 3 weeks post-vaccination
[b]PFU/0.1 ml dose
[c]Not tested

TABLE 2

Ability of recombinant vaccine FPV/NDV-HN + F (S-FPV-043) to vaccinate chicks with maternal antibody

| History Flock Vaccination | Hen Antibody[b] | | | Challenge[a] | | | |
|---|---|---|---|---|---|---|---|
| | | | | NDV | | FPV | |
| | NDV-HI[c] | NDV ELISA | FPV-AGP[d] | Vacc. | Con. | Vacc. | Con. |
| 1 NDV + FPV | 1:36 | 1:1738 | Neg | 75 | 30 | 90 | 0 |
| 2 NDV + FPV | 1:64 | 1:2852 | Neg | 85 | 55 | 100 | 0 |
| 3 NDV only | 1:92 | 1:4324 | Neg | 80 | 60 | 95 | 0 |
| 4 None | Neg | Neg | Neg | — | 0 | — | 0 |

[a]Percent protection following challenge 3 weeks post-vaccination.
[b]Every flock antibody.
[c]HI - Hemagglutination Inhibition Assay
[d]AGP - Agar Gel Precipitation Assay

EXAMPLE 2F

S-FPV-074

S-FPV-074 is a recombinant fowlpox virus that expresses two foreign genes. The genes for Newcastle Disease virus F protein and HN protein were inserted at the 681 insertion site. The F and HN genes are each under the control of a synthetic late/early promoter LP2EP2.

S-FPV-074 was derived from S-FPV-001. This was accomplished utilizing the homology vector 584-36.12 (see Materials and Methods) and virus S-FPV-001 in the HOMOLOGOUS RECOMBINATION PROCEDURE FOR GENERATING RECOMBINANT FPV. The transfection stock was screened by the PLAQUE HYBRIDIZATION PROCEDURE FOR PURIFYING RECOMBINANT FPV. The final result of plaque hybridization purification was the recombinant virus designated S-FPV-074.

S-FPV-074 was assayed for expression of NDV specific antigens using the BLACK PLAQUE SCREEN FOR FOREIGN GENE EXPRESSION IN RECOMBINANT FPV. Monoclonal antibodies specific for NDV HN (3-1G-5) and F (5-3F-2) were shown to react specifically with S-FPV-074 plaques and not with S-FPV-001 negative control plaques. All S-FPV-074 observed plaques reacted with the monoclonal antibodies indicating that the virus was stably expressing the NDV foreign genes.

S-FPV-074 expresses foreign antigens from NDV. This virus is useful as a multi-valent vaccine against Newcastle Diseases and Fowlpox.

EXAMPLE 3

Recombinant fowlpox viruses expressing proteins from Marek's disease virus (MDV) make vaccines protecting against both fowlpox virus and Marek's disease virus. We have constructed several recombinant FPV expressing MDV proteins: S-FPV-081, S-FPV-082 and S-FPV-085. Of these S-FPV-082 and S-FPV-085 also express proteins from Newcastle disease virus. These viruses are useful for vaccinating against fowlpox virus, Marek's disease virus, and Newcastle disease virus.

S-FPV-085 further expresses proteins from infectious laryngotracheitis virus (ILTV), making them useful as vaccines against ILTV.

EXAMPLE 3A
S-FPV-081

S-FPV-081 is a recombinant fowlpox virus that expresses three foreign genes. The gene for *E.coli* β-galactosidase (lacZ gene) and the genes for Marek's Disease virus (MDV) glycoprotein D (gD) and glycoprotein B (gB) were inserted into the 681 insertion site. The lac Z gene is under the control of a synthetic late promoter LP1 and the MDV gD and gB genes are under the control of the synthetic early/late promoters LP2EP2 and EP1LP2 respectively.

S-FPV-081 was derived from S-FPV-001. This was accomplished utilizing the homology vector 608-10.3 (see Materials and Methods) and virus S-FPV-001 in the HOMOLOGOUS RECOMBINATION PROCEDURE FOR GENERATING RECOMBINANT FPV. The transfection stock was screened by the SCREEN FOR RECOMBINANT FPV EXPRESSING ENZYMATIC MARKER GENES. The final result of red plaque purification was the recombinant virus designated S-FPV-081. This virus was assayed for β-galactosidase expression, purity, and insert stability by multiple passages monitored by the blue plaque assay as described in the materials and methods. After the initial three rounds of purification all plaques observed were blue indicating that the virus was pure, stable and expressing the marker gene.

S-FPV-081 was assayed for expression of MDV specific antigens using the BLACK PLAQUE SCREEN FOR FOREIGN GENE EXPRESSION IN RECOMBINANT FPV. Convalescent sera from MDV infected chickens was shown to react specifically with S-FPV-081 plaques and not with S-FPV-001 negative control plaques. All S-FPV-081 observed plaques reacted with the chicken antiserum indicating that the virus was stably expressing the MDV foreign genes. Western blot assays of infected cell lysates using convalescent sera from MDV-infected chickens indicated that S-FPV-081 was expressing a MDV glycoprotein B and MDV glycoprotein D.

S-FPV-081 expresses foreign antigens from MDV. This virus is useful as a multi-valent vaccine against Marek's Disease and Fowlpox.

EXAMPLE 3B
S-FPV-082

S-FPV-082 is a recombinant fowlpox virus that expresses five foreign genes. The genes for Newcastle Disease virus F protein and HN protein were inserted at the 680 insertion site. The F and HN genes are each under the control of a synthetic early/late promoter EP1LP2. The gene for *E. coli* β-galactosidase (lacZ gene) and the genes for Marek's Disease virus (MDV) gD and gB were inserted into the 681 insertion site. The lacZ gene is under the control of a synthetic late promoter LP1 and the MDV gD and gB genes are under the control of the synthetic early/late promoters LP2EP2 and EP1LP2 respectively.

S-FPV-082 was derived from S-FPV-043. This was accomplished utilizing the homology vector 608-10.3 (see Materials and Methods) and virus S-FPV-043 in the HOMOLOGOUS RECOMBINATION PROCEDURE FOR GENERATING RECOMBINANT FPV. The transfection stock was screened by the SCREEN FOR RECOMBINANT FPV EXPRESSING ENZYMATIC MARKER GENES. The final result of red plaque purification was the recombinant virus designated S-FPV-082. This virus was assayed for β-galactosidase expression, purity, and insert stability by multiple passages monitored by the blue plaque assay as described in the materials and methods. After the initial three rounds of purification all plaques observed were blue indicating that the virus was pure, stable and expressing the marker gene.

S-FPV-082 was assayed for expression of MDV specific antigens using the BLACK PLAQUE SCREEN FOR FOREIGN GENE EXPRESSION IN RECOMBINANT FPV. Convalescent sera from MDV infected chickens was shown to react specifically with S-FPV-082 plaques and not with S-FPV-001 negative control plaques. All S-FPV-082 observed plaques reacted with the chicken antiserum indicating that the virus was stably expressing the MDV foreign genes.

S-FPV-082 expresses foreign antigens from NDV and MDV. This virus will be valuable as a multi-valent vaccine against Newcastle Disease, Marek's Disease and Fowlpox.

EXAMPLE 3C
S-FPV-085

S-FPV-085 is a recombinant fowlpox virus that expresses eight foreign genes. The genes for Newcastle Disease virus F protein and HN protein are inserted at the 680 insertion site. The F and HN genes are each under the control of a synthetic early/late promoter EP1LP2. The gene for *E.coli* β-galactosidase (lacZ gene) and the genes for Marek's Disease virus (MDV) gD and gB are inserted into the 681 insertion site. The lac Z gene is under the control of a synthetic late promoter LP1 and the MDV gD and gB genes are under the control of the synthetic early/late promoters LP2EP2 and EP1LP2 respectively. The gene for *E.coli* β-glucuronidase (uidA gene) and the genes for Infectious Laryngotracheitis virus (ILTV) gD and gB are inserted into the 540 insertion site. The uidA gene is under the control of a synthetic late promoter LP1 and the ILTV gD and gB genes are each under the control of a synthetic early/late promoter EP1LP2.

S-FPV-085 is derived from S-FPV-082. This is accomplished utilizing the homology vector 586-36.6 (see Materials and Methods) and virus S-FPV-082 in the HOMOLOGOUS RECOMBINATION PROCEDURE FOR GENERATING RECOMBINANT FPV. The transfection stock is screened by the SCREEN FOR RECOMBINANT FPV EXPRESSING ENZYMATIC MARKER GENES. The final result of blue plaque (β-glucuronidase) purification is the recombinant virus designated S-FPV-085. This virus is assayed for β-glucuronidase expression, purity, and insert stability by multiple passages monitored by the blue plaque assay as described in the materials and methods. After the initial three rounds of purification all plaques observed are blue indicating that the virus is pure, stable and expressing the marker gene.

S-FPV-085 is assayed for expression of MDV specific antigens using the BLACK PLAQUE SCREEN FOR FOREIGN GENE EXPRESSION IN RECOMBINANT FPV. S-FPV-085 expresses foreign antigens from NDV, MDV and ILTV. This virus is useful as a multi-valent vaccine against Newcastle Disease, Marek's Disease, Infectious Laryngotracheitis and Fowlpox.

EXAMPLE 4

Recombinant fowlpox virus (FPV) expressing proteins from infectious laryngotracheitis virus (ILTV) make vaccines protecting against both FPV and ILTV. We have constructed several recombinant FPV expressing ILTV proteins: S-FPV-095, S-FPV-083, and S-FPV-097. Of these, S-FPV-083 and S-FPV-097 also express proteins from Newcastle disease virus (NDV), making them useful as vaccines against NDV sa well.

EXAMPLE 4B
S-FPV-095

S-FPV-095 is a recombinant fowlpox virus that expresses three foreign genes. The gene for E.coli β-glucuronidase (uidA gene) and the genes for Infectious Laryngotracheitis virus (ILTV) glycoprotein D (gD) and glycoprotein B (gB) were inserted into the 540 insertion site. The uidA gene is under the control of a synthetic late promoter LP1 and the ILTV gD and gB genes are each under the control of a synthetic early/late promoter EP1LP2.

S-FPV-095 was derived from S-FPV-001. This was accomplished utilizing the homology vector 694-10.4 (see Materials and Methods) and virus S-FPV-001 in the HOMOLOGOUS RECOMBINATION PROCEDURE FOR GENERATING RECOMBINANT FPV. The transfection stock was screened by the SCREEN FOR RECOMBINANT FPV EXPRESSING ENZYMATIC MARKER GENES. The final result of blue plaque purification (β-glucuronidase) was the recombinant virus designated S-FPV-095. This virus was assayed for β-glucuronidase expression, purity, and insert stability by multiple passages monitored by the blue plaque assay as described in the materials and methods. After the initial three rounds of purification all plaques observed were blue indicating that the virus was pure, stable and expressing the marker gene.

S-FPV-095 was assayed for expression of ILTV specific antigens using the BLACK PLAQUE SCREEN FOR FOREIGN GENE EXPRESSION IN RECOMBINANT FPV. Antibodies to ILTV gB and gD was shown to react specifically with S-FPV-095 plaques and not with S-FPV-001 negative control plaques. All S-FPV-095 observed plaques reacted with the antiserum indicating that the virus was stably expressing the ILTV foreign genes.

S-FPV-095 expresses foreign antigens from ILTV. This virus is useful as a multi-valent vaccine against Infectious Laryngotracheitis and Fowlpox.

EXAMPLE 4B
S-FPV-083

S-FPV-083 is a recombinant fowlpox virus that expresses five foreign genes. The genes for Newcastle Disease virus F protein and HN protein were inserted at the 680 insertion site. The F and HN genes are each under the control of a synthetic early/late promoter EP1LP2. The gene for E. coli β-glucuronidase (uidA gene) and the genes for Infectious Laryngotracheitis virus (ILT) gD and gB were inserted into the 540 insertion site. The uidA gene is under the control of a synthetic late promoter LP1 and the ILT gD and gB genes are each under the control of a synthetic early/late promoter (EP1LP2).

S-FPV-083 was derived from S-FPV-043. This was accomplished utilizing the homology vector 586-36.6 (see Materials and Methods) and virus S-FPV-043 in the HOMOLOGOUS RECOMBINATION PROCEDURE FOR GENERATING RECOMBINANT FPV. The transfection stock was screened by the SCREEN FOR RECOMBINANT FPV EXPRESSING ENZYMATIC MARKER GENES. The final result of blue plaque purification was the recombinant virus designated S-FPV-083. This virus was assayed for β-glucuronidase expression, purity, and insert stability by multiple passages monitored by the blue plaque assay as described in the materials and methods. After the initial three rounds of purification all plaques observed were blue indicating that the virus was pure, stable and expressing the marker gene.

S-FPV-083 was assayed for expression of ILTV specific antigens using the BLACK PLAQUE SCREEN FOR FOREIGN GENE EXPRESSION IN RECOMBINANT FPV. Convalescent sera from ILTV infected chickens was shown to react specifically with S-FPV-083 plaques and not with S-FPV-001 negative control plaques. All S-FPV-083 observed plaques reacted with the chicken antiserum indicating that the virus was stably expressing the ILTV foreign genes.

S-FPV-083 expresses foreign antigens from NDV and ILTV. This virus will be valuable as a multi-valent vaccine against Newcastle Disease, Infectious Laryngotracheitis and Fowlpox.

EXAMPLE 4C
S-FPV-097

S-FPV-097 is a recombinant fowlpox virus that expresses five foreign genes. The genes for Newcastle Disease virus F protein and HN protein were inserted at the 680 insertion site. The F and HN genes are each under the control of a synthetic early/late promoter EP1LP2. The gene for E.coli β-glucuronidase (uidA gene) and the genes for Infectious Laryngotracheitis virus (ILTV) glycoprotein D (gD) and glycoprotein B (gB) were inserted into the 540 insertion site. The uidA gene is under the control of a synthetic late promoter LP1 and the ILTV gD and gB genes are each under the control of a synthetic early/late promoter EP1LP2.

S-FPV-097 was derived from S-FPV-043. This was accomplished utilizing the homology vector 694-10.4 (see Materials and Methods) and virus S-FPV-043 in the HOMOLOGOUS RECOMBINATION PROCEDURE FOR GENERATING RECOMBINANT FPV. The transfection stock was screened by the SCREEN FOR RECOMBINANT FPV EXPRESSING ENZYMATIC MARKER GENES. The final result of blue plaque purification was the recombinant virus designated S-FPV-097. This virus was assayed for β-glucuronidase expression, purity, and insert stability by multiple passages monitored by the blue plaque assay as described in the materials and methods. After the initial three rounds of purification all plaques observed were blue indicating that the virus was pure, stable and expressing the marker gene.

S-FPV-097 was assayed for expression of ILTV specific antigens using the BLACK PLAQUE SCREEN FOR FOREIGN GENE EXPRESSION IN RECOMBINANT FPV. Antibodies to ILTV gB and gD was shown to react specifically with S-FPV-097 plaques and not with S-FPV-001 negative control plaques. All S-FPV-097 observed plaques reacted with the antiserum indicating that the virus was stably expressing the ILTV foreign genes. All S-FPV-097 observed plaques reacted with the chicken antiserum to ILTV indicating that the virus was stably expressing the ILTV foreign genes. Monoclonal antibodies specific for NDV HN (3-1G-5) and F (5-3F-2) were shown to react specifically with S-FPV-097 plaques and not with S-FPV-001 negative control plaques. All S-FPV-097 observed plaques reacted with the monoclonal antibodies indicating that the virus was stably expressing the NDV foreign genes.

S-FPV-097 expresses foreign antigens from NDV and ILTV. This virus is useful as a multi-valent vaccine against Newcastle Disease, Infectious Laryngotracheitis and Fowlpox.

EXAMPLE 5

Recombinant fowlpox virus (FPV) expressing proteins from infectious bronchitis virus (IBV) make vaccines protecting against both FPV and IBV. We have constructed two recombinant FPV expressing IBV proteins: S-FPV-072 and S-FPV-079. Both of these viruses also express proteins from Newcastle disease virus (NDV), making them useful as vaccines against NDV.

EXAMPLE 5A

S-FPV-072

S-FPV-072 is a recombinant fowlpox virus that expresses five foreign genes. The genes for Newcastle Disease virus F protein and HN protein were inserted at the 680 insertion site. The F and HN genes are each under the control of a synthetic early/late promoter EP1LP2. The gene for *E.coli* β-galactosidase (lacZ gene) and the genes for Infectious Bronchitis virus (IBV) Massachusetts Spike protein (Mass Spike) and Massachusetts Matrix protein (Mass Matrix) were inserted into the 681 insertion site. The lac Z gene is under the control of a synthetic late promoter LP1 and the IBV Mass Spike and Mass Matrix genes are each under the control of the synthetic early/late promoter EP1LP2.

S-FPV-072 was derived from S-FPV-043. This was accomplished utilizing the homology vector 538-51.27 (see Materials and Methods) and virus S-FPV-043 in the HOMOLOGOUS RECOMBINATION PROCEDURE FOR GENERATING RECOMBINANT FPV. The transfection stock was screened by the SCREEN FOR RECOMBINANT FPV EXPRESSING ENZYMATIC MARKER GENES. The final result of red plaque purification was the recombinant virus designated S-FPV-072. This virus was assayed for B-galactosidase expression, purity, and insert stability by multiple passages monitored by the blue plaque assay as described in the materials and methods. After the initial three rounds of purification, all plaques observed were blue indicating that the virus was pure, stable and expressing the marker gene.

S-FPV-072 was assayed for expression of NDV and IBV specific antigens using the BLACK PLAQUE SCREEN FOR FOREIGN GENE EXPRESSION IN RECOMBINANT FPV. Monoclonal antibody 15-88 to the IBV Mass Spike protein was shown to react specifically with S-FPV-072 plaques and not with S-FPV-001 negative control plaques. All S-FPV-072 observed plaques reacted with the monoclonal antibodies indicating that the virus was stably expressing the IBV foreign gene. Western blot assays of infected cell lysates using monoclonal antibody 15-88 to the IBV Mass Spike protein indicated that S-FPV-072 was expressing a 90 kD IBV Mass Spike protein. Monoclonal antibodies specific for both HN (3-1G-5) and F (5-3F-2) were shown to react specifically with S-FPV-072 plaques and not with S-FPV-001 negative control plaques. All S-FPV-072 observed plaques reacted with the monoclonal antibodies indicating that the virus was stably expressing the NDV foreign genes.

S-FPV-072 expresses foreign antigens from NDV and IBV. This virus is useful as a multi-valent vaccine against Newcastle Diseases, Infectious Bronchitis, and Fowlpox.

EXAMPLE 5B

S-FPV-079 is a recombinant fowlpox virus that expresses seven foreign genes. The genes for Newcastle Disease virus F protein and HN protein were inserted at the 680 insertion site. The F and HN genes are each under the control of a synthetic early/late promoter EP1LP2. The gene for *E.coli* β-galactosidase (lacZ gene) and the genes for Infectious Bronchitis virus (IBV) Massachusetts Spike protein (Mass Spike) and Massachusetts Matrix protein (Mass Matrix) were inserted into the 681 insertion site. The lac Z gene is under the control of a synthetic late promoter LP1 and the IBV Mass Spike and Mass Matrix genes are each under the control of the synthetic early/late promoter EP1LP2. The gene for the *E. coli* β-glucuronidase (uidA) gene and the gene for the IBV Mass Nucleocapsid protein were inserted into the 540 insertion site. The uidA gene is under the control of the synthetic late/early promoter LP2EP2 and the IBV Mass Nucleocapsid gene is under the control of the synthetic early/late promoter EP1LP2.

S-FPV-079 was derived from S-FPV-072. This was accomplished utilizing the Homology Vector 611-49.1 (see Materials and Methods) and virus S-FPV-072 in the HOMOLOGOUS RECOMBINATION PROCEDURE FOR GENERATING RECOMBINANT FPV. The transfection stock was screened by the SCREEN FOR RECOMBINANT FPV EXPRESSING ENZYMATIC MARKER GENES. The final result of red plaque purification was the recombinant virus designated S-FPV-079. This virus was assayed for B-galactosidase expression, purity, and insert stability by multiple passages monitored by the blue plaque assay as described in the materials and methods. After the initial three rounds of purification, all plaques observed were blue indicating that the virus was pure, stable and expressing the marker gene.

S-FPV-079 was assayed for expression of NDV and IBV specific antigens using the BLACK PLAQUE SCREEN FOR FOREIGN GENE EXPRESSION IN RECOMBINANT FPV. Monoclonal antibody 15-88 to the IBV Mass Spike protein was shown to react specifically with S-FPV-072 plaques and not with S-FPV-001 negative control plaques. All S-FPV-079 observed plaques reacted with the monoclonal antibody antiserum to IBV indicating that the virus was stably expressing the IBV foreign gene. Western blot assays of infected cell lysates using monoclonal antibody 15-88 to the IBV Mass Spike protein indicated that S-FPV-079 was expressing a 90 kD IBV Mass Spike protein. Monoclonal antibodies specific for both HN (3-1G-5) and F (5-3F-2) were shown to react specifically with S-FPV-079 plaques and not with S-FPV-001 negative control plaques. All S-FPV-079 observed plaques reacted with the monoclonal antibodies indicating that the virus was stably expressing the NDV foreign genes.

S-FPV-079 expresses foreign antigens from NDV and IBV. This virus is useful as a multi-valent vaccine against Newcastle Diseases, Infectious Bronchitis, and Fowlpox.

EXAMPLE 6

Recombinant fowlpox virus, S-FPV-099 or S-FPV-101, expressing chicken interferon (cIFN) or S-FPV-100, expressing chicken myelomonocytic growth factor (cMGF), are useful to enhance the immune response when added to vaccines against diseases of poultry. Chicken myelomonocytic growth factor (cMGF) is homologous to mammalian interleukin-6 protein, and chicken interferon (cIFN) is homologous to mammalian interferon Type I. When used alone or in combination with vaccines against specific avian diseases, S-FPV-099, S-FPV-100 and S-FPV-101 provide enhanced mucosal, humoral, or cell mediated immunity against avian disease-causing viruses including, but not limited to, Marek's disease virus, Newcastle disease virus, infectious laryngotracheitis virus, infectious bronchitis virus, infectious bursal disease virus.

S-FPV-099

S-FPV-099 is a recombinant fowlpox virus that expresses two foreign genes. The genes for chicken interferon (CIFN) and *E. coli* lacZ were inserted at the uniqe SnaBI restriction endonuclease site in the 2.8 kB EcoRI FPV genomic fragment (681 insertion site). The cIFN gene is under the control of a synthetic late/early promoter LP2EP2, and the *E. coli* lacZ gene is under the control of a synthetic late promoter LP1.

S-FPV-099 was derived from S-FPV-001. This was accomplished utilizing the homology vector 751-07.D1 (see Materials and Methods) and virus S-FPV-001 in the HOMOLOGOUS RECOMBINATION PROCEDURE FOR GENERATING RECOMBINANT FPV. The transfection stock was screened by the SCREEN FOR RECOMBINANT FPV EXPRESSING ENZYMATIC MARKER GENES. The final result of red plaque purification was the recombinant virus designated S-FPV-099. This virus was assayed for β-galactosidase expression, purity, and insert stability by multiple passages monitored by the blue plaque assay as described in Materials and Methods. After the initial three rounds of purification, all plaques observed were blue indicating that the virus S-FPV-099 was pure, stable, and expressing the foreign gene.

Supernatants from S-FPV-099 have interferon activity in cell culture. Addition of S-FPV-099 conditioned media to chicken embryo fibroblast (CEF) cell culture inhibits infection of the CEF cells by vesicular stomatitis virus or by herpesvirus of turkeys. S-FPV-099 is useful to enhance the immune response alone or when added to vaccines against diseases of poultry.

S-FPV-100

S-FPV-100 is a recombinant fowlpox virus that expresses two foreign genes. The genes for chicken myelomonocytic growth factor (cMGF) and *E. coli* lacZ were inserted at the uniqe SnaBI restriction endonuclease site in the 2.8 kB EcoRI FPV genomic fragment (681 insertion site). The cMGF gene is under the control of a synthetic late/early promoter LP2EP2, and the *E. coli* lacZ gene is under the control of a synthetic late promoter LP1.

S-FPV-100 was derived from S-FPV-001. This was accomplished utilizing the homology vector 751-56.C1 (see Materials and Methods) and virus S-FPV-001 in the HOMOLOGOUS RECOMBINATION PROCEDURE FOR GENERATING RECOMBINANT FPV. The transfection stock was screened by the SCREEN FOR RECOMBINANT FPV EXPRESSING ENZYMATIC MARKER GENES. The final result of red plaque purification was the recombinant virus designated S-FPV-100. This virus was assayed for β-galactosidase expression, purity, and insert stability by multiple passages monitored by the blue plaque assay as described in Materials and Methods. After the initial three rounds of purification, all plaques observed were blue indicating that the virus S-FPV-100 was pure, stable, and expressing the foreign gene.

S-FPV-100 is useful to enhance the immune response alone or when added to vaccines against diseases of poultry.

S-FPV-101

S-FPV-101 is a recombinant fowlpox virus that expresses four foreign genes. The genes for chicken interferon (cIFN) and *E. coli* lacZ were inserted at the uniqe SnaBI restriction endonuclease site in the 2.8 kB EcoRI FPV genomic fragment (681 insertion site). The cIFN gene is under the control of a synthetic late/early promoter LP2EP2, and the *E. coli* lacZ gene is under the control of a synthetic late promoter LP1. The genes for Newcastle Disease virus F protein and HN protein were inserted at the 680 insertion site. The F and HN genes are each under the control of a synthetic early/late promoter EP1LP2.

S-FPV-101 was derived from S-FPV-043. This was accomplished utilizing the homology vector 751-07.D1 (see Materials and Methods) and virus S-FPV-043 in the HOMOLOGOUS RECOMBINATION PROCEDURE FOR GENERATING RECOMBINANT FPV. The transfection stock was screened by the SCREEN FOR RECOMBINANT FPV EXPRESSING ENZYMATIC MARKER GENES. The final result of red plaque purification was the recombinant virus designated S-FPV-101. This virus was assayed for β-galactosidase expression, purity, and insert stability by multiple passages monitored by the blue plaque assay as described in Materials and Methods. After the initial three rounds of purification, all plaques observed were blue indicating that the virus S-FPV-101 was pure, stable, and expressing the foreign gene.

Supernatants from S-FPV-101 have interferon activity in cell culture. Addition of S-FPV-101 conditioned media to chicken embryo fibroblast (CEF) cell culture inhibits infection of the CEF cells by vesicular stomatitis virus or by herpesvirus of turkeys. S-FPV-101 is useful to enhance the immune response alone or when added to vaccines against diseases of poultry. S-FPV-101 is useful as a multi-valent vaccine against Newcastle Diseases and Fowlpox.

EXAMPLE 7

Recombinant fowlpox virus expressing Newcastle's disease virus HN and F proteins lacking the membrane anchor sequences is a superior vaccine against fowlpox and Newcastle's disease.

Day old chicks from hens which have been exposed to or vaccinated against Newcastle's disease virus carry antibodies to NDV which may neutralize a vaccine containing a recombinant fowlpox virus expressing the NDV HN and F proteins. In vitro virus neutralization (VN) assays using VN monoclonal antibodies specific for either NDV HN or F proteins have been shown to neutralize recombinant fowlpox virus expressing the NDV HN and F proteins. These results suggest that the NDV HN and F glycoproteins are incorporated into the fowlpox virus virion. To increase the efficacy of a vaccine in the presence on maternal antibodies against Newcastle's disease virus, a recombinant fowlpox virus is constructed which expresses the NDV HN and F proteins lacking the membrane anchor domains of each protein. The resulting recombinant virus produces NDV HN and F proteins secreted into the serum of the vaccinated animal producing a strong humoral and cell mediated immune response to the Newcastle's disease virus. The NDV HN and F proteins are not presented on the surface of the FPV particle and thus evade neutralization by maternal antibodies present in the vaccinated day old chicks.

The hemagglutinin-Neuraminidase (HN) and Fusion (F) genes from the B1 strain of Newcastle Disease Virus (ATCC VR-108) were isolated as cDNA clones, using oligo dT primed poly A selected mRNA.

The fusion (F) protein mediates penetration of NDV into host cells by fusion of the viral envelope with the host cell plasma membrane. A posttranslational cleavage of inactive precursors $F_0$ into two disulfide-bonded polypeptides, F1 and F2, is necessary to produce fusion active F protein and thereby yield infectious virions. The new hydrophobic N-terminus of F1 generated after cleavage of $F_0$ is responsible for the fusion characteristic of paramyxoviruses and thus determines virulence. The required proteolytic cleavage signal (paired basic residues) in the NDV B1 strain is altered, thereby preventing cleavage of $F_0$ into F1 and F2, resulting in an attenuated NDV strain.

The addition of the NDV F signal sequence (aa1-25) to VP2 (vFP147), resulted in the secretion of VP2 in the TC fluid, but abolished its protective response (Paoletti, et. al WO 93/03145). Three hydrophobic domains exist within the F glycoprotein which interact with the lipid bilayer: 1). The signal sequence at the N-terminus of the primary translation product $F_0$; 2). the N-terminus of F1; and 3). the transmembrane anchor domain near the C-terminus of F1. The F glycoprotein of the B1 strain of NDV is 544 amino acids in length with the transmembrane anchor domain spanning 27 amino acids from position 500 to 526 (LITYIVLTIISLVFGILSLILACYLMY) (SEQ ID NO: 35). Amino acids 1-499 of the NDV F protein are expressed under the control of a synthetic promoter element which functions as both an early and late promoter, such as EP1LP2 or LP2EP2, directing expression throughout the reproduction cycle. This results in the deletion of amino acids 527-544, the cytoplasmic tail, thought to interact with the inner membrane protein (M) before or during virus assembly. A recombinant fowlpox virus is constructed which expresses the NDV F protein lacking the C-terminal membrane anchor domain from a synthetic early/late promoter.

The hemagglutinin-neuraminidase (HN) glycoprotein provides NDV with the ability to agglutinate and elute erythrocytes. The process consists of two stages: attachment of the virus to the receptor on the red blood cell surface (agglutination) and destruction of the receptor by the neuraminidase enzyme activity (elution). The major hydrophobic anchor domain is present near the N-terminus of HN, supporting the view that the N-terminus is anchored to the lipid bilayer. The HN glycoprotein of the B1 strain of NDV is 577 amino acids in length with the transmembrane anchor domain spanning 28 amino acids from position 27 to 54 (IAILFLTWTLAISVASLLYSMGASTPS) (SEQ ID NO: 36). The extreme N-terminal amino acids (1 to 26) are relatively hydrophilic. Amino acids 55 to 577 of the HN protein are expressed under the control of a synthetic promoter element which functions as both an early and late promoter, such as EP1LP2 or LP2EP2, directing expression throughout the reproduction cycle. THE NDV HN polypeptide has a membrane transport signal sequence, such as the PRV gX signal sequence, at its amino terminus to direct the protein to be secreted into the serum of a vaccinated animal. A recombinant fowlpox virus is constructed which expresses the NDV HN protein lacking the N-terminal membrane anchor domain and containing an N-terminal PRV gX signal sequence from a synthetic early/late promoter. Alternatively the NDV HN polypeptide contains a deletion of the transmembrane anchor domain spanning 28 amino acids from position 27 to 54 and retains amino acids 1 to 26 and 55 to 577. A recombinant fowlpox virus is constructed which expresses the NDV HN protein lacking the membrane anchor domain (amino acids 27 to 54) from a synthetic early/late promoter.

A recombinant fowlpox virus is constructed which expresses both the NDV HN and F proteins lacking the membrane anchor domains of each protein from a synthetic early/late promoter. The resulting recombinant virus produces NDV HN and F proteins secreted into the serum of the vaccinated animal producing a strong humoral and cell mediated immune response to the Newcastle's disease virus. The NDV HN and F proteins are not presented on the surface of the FPV particle and thus evade neutralization by maternal antibodies present in the vaccinated day old chicks.

EXAMPLE 8

Recombinant fowlpox virus expressing cell surface receptors on the surface of the FPV viral particle useful for targeting gene products to specific tissues or organs.

Serum from chickens carrying maternal antibodies to Newcastle's disease virus inhibits productive infection and plaque formation by S-FPV-043 on chicken embryo fibroblasts in cell culture. One explanation for this result is that the antigenic epitopes of the NDV HN and F proteins expressed in S-FPV-043 are displayed on the surface of the fowlpox viral particle. Display of proteins on the surface of the FPV particle is useful to target specific gene products to specific normal cell types or tumor cell types. Proteins which are displayed on the surface of the FPV particle include but are not limited to integrins which would target the virus to integrin receptors on the cell surface; erythropoetin which would target the virus to erythropoetin receptors on the surface of red blood cells; antibodies or other proteins which would target to specific proteins or receptors on the surface of normal or tumor cells. The fowlpox virus also delivers cytokines, interleukins, interferons, or colony stimulating factors which stimulate a strong humoral or cell mediated immune response against a tumor or disease causing organism. The proteins displayed on the surface of the fowlpox virus are expressed from the fowlpox genome as fusion proteins to the membrane anchor domains of the NDV HN or F proteins, or to other proteins containing membrane anchor domains. The cytokines, interleukins, interferons, or colony stimulating factors are expressed as fusion proteins to PRV gX, E. coli β-galactosidase or another protein in a soluble, not membrane bound, form. The fusion protein stabilizes the cytokine protein and allows it to diffuse in the serum of the animal to reach its cellular target.

EXAMPLE 9

S-FPV-098

S-FPV-098 is a recombinant fowlpox virus that expresses two foreign genes. The genes for infectious bursal disease virus (IBDV) polymerase gene and E. coli lacZ were inserted at the 681 insertion site. The IBDV polymerase gene is under the control of a synthetic late/early promoter LP2EP2, and the E. coli lacZ gene is under the control of a synthetic late promoter LP1.

S-FPV-098 was derived from S-FPV-001. This was accomplished utilizing the homology vector 749-75.82 (see Materials and Methods) and virus S-FPV-001 in the HOMOLOGOUS RECOMBINATION PROCEDURE FOR GENERATING RECOMBINANT FPV. The transfection stock was screened by the SCREEN FOR RECOMBINANT FPV EXPRESSING ENZYMATIC MARKER GENES. The final result of red plaque purification was the recombinant virus designated S-FPV-098. This virus was assayed for β-galactosidase expression, purity, and insert stability by multiple passages monitored by the blue plaque assay as described in Materials and Methods. After the initial three rounds of purification, all plaques observed were blue indicating that the virus S-FPV-098 was pure, stable, and expressing the foreign gene.

S-FPV-098 is useful for expression of IBDV polymerase protein. S-FPV-098 is useful in an in vitro approach to a recombinant IBDV attenuated vaccine. RNA strands from the attenuated IBDV strain are synthesized in a bacterial expression system using T3 or T7 promoters (pBlueScript plasmid; Stratagene, Inc.) to synthesize double stranded short and long segments of the IBDV genome. The IBDV double stranded RNA segments and S-FPV-098 are transfected into Vero cells. The fowlpox virus expresses the IBDV polymerase but does not replicate in Vero cells. The IBDV polymerase produced from S-FPV-098 synthesizes infectious attenuated IBDV virus from the double stranded RNA genomic templates. The resulting attenuated IBDV virus is useful as a vaccine against infectious bursal disease in chickens.

As an alternative to the construction of a IBD vaccine using a viral vectored delivery system and/or subunit approaches, IBD virus RNA is directly manipulated re-constructing the virus using full length RNA derived from cDNA clones representing both the large (segment A) and small (segment B) double-stranded RNA subunits. Generation of IBD virus is this manner offers several advantages over the first two approaches. First, if IBD virus is re-generated using RNA templates, one is able to manipulate the cloned cDNA copies of the viral genome prior to transcription (generation of RNA). Using this approach, it is possible to either attenuate a virulent IBD strain or replace the VP2 variable region of the attenuated vaccine backbone with that of virulent strains. In doing so, the present invention provides protection against the virulent IBDV strain while providing the safety and efficacy of the vaccine strain. Furthermore, using this approach, the present invention constructs and tests temperature sensitive IBD viruses generated using the RNA polymerase derived from the related birnavirus infectious pancreatic necrosis virus (IPNV) and the polyprotein derived from IBDV. The IPNV polymerase has optimum activity at a temperature lower than that of IBDV. If the IPNV polymerase recognizes the regulatory signals present on IBDV, the hybrid virus is expected to be attenuated at the elevated temperature present in chickens. Alternatively, it is possible to construct and test IBD viruses generated using the RNA polymerase derived from IBDV serotype 2 viruse and the polyprotein derived from IBDv-serotype 1 virus.

cDNA clones representing the complete genome of IBDV (double stranded RNA segments A and B) is constructed, initially using the BursaVac vaccine strain (Sterwin Labs). Once cDNA clones representing full length copies of segment A and B are constructed, template RNA is prepared. Since IBDV exists as a bisegmented double-stranded RNA virus, both the sense and anti-sense RNA strands of each segment are produced using the pBlueScript plasmid; Stratagene, Inc.). These vectors utilize the highly specific phage promoters SP6 or T7 to produce substrate amounts of RNA in vitro. A unique restriction endonuclease site is engineered into the 3' PCR primer to linearize the DNA for the generation of run-off transcripts during transcription.

The purified RNA transcripts (4 strands) are transfected into Vero cells to determine whether the RNA is infectious. If IBD virus is generated, as determined by black plaque assays using IBDV specific Mabs, no further manipulations are required and engineering of the vaccine strain can commence. The advantage of this method is that engineered IBD viruses generated in this manner will be pure and require little/no purification, greatly decreasing the time required to generate new vaccines. If negative results are obtained using the purified RNA's, functional viral RNA polymerase is required by use of a helper virus. Birnaviruses replicate their nucleic acid by a strand displacement (semi-conservative) mechanism, with the RNA polymerase binding to the ends of the double-stranded RNA molecules forming circularized ring structures (Muller & Nitschke, Virology 159, 174–177, 1987). RNA polymerase open reading frame of about 878 amino acids in fowlpox virus is expressed and this recombinant virus (S-FPV-098) is used to provide functional IBDV RNA polymerase in trans. Fowlpox virus expressed immunologically recognizable foreign antigens in non-avian cells (vero cells), where there are no signs of productive replication of the viral vector (Paoletti et al., Technological Advances in Vaccine Development, 321–334, 1988, Alan R. Liss, Inc.). In the present invention the IBDV polymerase protein is expressed in the same cells as the transfected RNA using the fowlpox virus vector without contaminating the cells with FPV replication.

With the demonstration that IBD virus is generated in vitro using genomic RNA, an improved live attenuated virus vaccines against infectious bursal disease is developed. Using recombinant DNA technology along with the newly defined system of generating IBD virus, specific deletions within the viral genome, facilitating the construction of attenuated viruses are made. Using this technology, the region of IBDV responsible for virulence and generate attenuated, immunogenic IBDV vaccines are identified. The present invention provides a virulent IBD strain or replacement of the VP2 variable region of the attenuated vaccine backbone with that of a virulent strain, thus protecting against the virulent strain while providing the safety and efficacy of the vaccine strain.

EXAMPLE 10

The chicken interferon (cIFN) gene was cloned into wild type (FPV) viruses by homologous recombinant techniques. Briefly, the entire coding region of cIFN was isolated from activated chicken spleen cell RNA by RT/PCR using primer sequences from the recently published cIFN sequence (Sekellick, M., et al., 1994). Recombinant FPV viruses containing CIFN, and FPV/cIFN (S-FPV-099), were engineered to contain the entire cIFN ORF under the control of a synthetic pox virus promoter (LP2EP2), which functions as both an early and late promoter, directing expression throughout the entire viral replication cycle. A third recombinant virus, FPV/cIFN+NDV, (S-FPV-101) was made in a similar manner, except that a FPV virus previously engineered to contain the Newcastle Disease (NDV) antigens HN and F was used as the parent virus during homologous recombination, thus yielding a recombinant fowlpox virus co-expressing the cIFN and NDV genes. All recombinant viruses contain the lac Z gene engineered in tandem with cIFN under the control of a synthetic late (LP1) pox promoter. All promoter/gene constructs were sequenced at the promoter/cIFN junction to confirm the integrity of the proper DNA coding frame. Co-expression of β-galactosidase facilitated the isolation and plaque purification of the recombinant viruses. Independent viral insertion sites were used for insertion of the cIFN gene and the NDV genes in the fowlpox virus. The insertion sites were found to interrupt nonessential virus genes in both SPV and FPV.

To confirm the presence of the cIFN gene, recombinant viral DNAs were analyzed by PCR, using cIFN specific primers flanking the coding region. All viral DNA's yielded the expected 600 bp amplified cIFN DNA product. In addition, southern blot analysis on the viral DNA was performed using a non-radioactive labeled cIFN cDNA probe. Plasmid constructs containing the cIFN gene cassettes were sequenced across the transcriptional and translational initiation/termination signals, to confirm the integrity of the ORF.

Growth Properties of Recombinant Viruses in Cell Culture

Recombinant FPV/cIFN and FPV/cIFN+NDV were found to be attenuated with respect to their growth in chicken embryo fibroblast (CEF) cells. Plaque size was decreased significantly and viral titers were 0.9–1.4 logs less when compared to wild type FPV. We suggest that fowlpox virus has anti-IFN mechanisms, similar to anti-IFN mechanisms reported for other pox viruses, e.g. vaccinia, cowpox. And that these mechanisms help the virus to overcome the inhibitory effects of exogenously expressed CIFN. Therefore, fowlpox virus is able to infect, replicate and retain a productive infectious state.

In Vivo Properties of Recombinant FPV/cIFN Virus in Chicks 10-day old chicks were inoculated, subcutaneously, with recombinant FPV/cIFN (S-FPV-099) virus at increasing dosages. At 10 days post inoculation, all chicks were inoculated with a mixture of sheep red blood cells (SRBC) and *Brucella abortus* (BA). At 15 days post FPV/cIFN virus inoculation, sera was collected, total body weights and antibody responses to SRBC's and BA were measured, and chicks were sacrificed for necropsy analysis. These data show that there were no significant differences in chick body weight, SRBC and BA antibody responses or gross pathology[c] associated with inoculation of recombinant FPV/cIFN virus, as compared to chicks inoculated with PBS alone. Therefore, this virus appears to be safe in 10-day old chicks.

TABLE 3

Determination of safety of recombinant FPV/cIFN virus in 10-day old chicks

| FPV/cIFN (pfu/chick) | Total body weight (grams)[a,b] | Antibody titers[a,d] BA | SRBC |
|---|---|---|---|
| 0 (PBS) | 438 | 4.66 | 2.16 |
| 600 | 460 | 4.00 | 2.00 |
| 6,000 | 461 | 4.25 | 2.00 |
| 60,000 | 460 | 4.62 | 2.00 |

[a]Measured 15 days post FPV/cIFN virus inoculation
[b]Mean body weight (n = 8).
[c]There were no detectable gross pathological changes in any of the groups.
[d]Mean antibody titers were determined by agglutination assay and expressed as $\log_2$ (n = 8).

One-day old chicks were inoculated intranasally/intraocularly with NDV B1 ($10^6$ ELD$_{50}$/chick) alone or in addition to subcutaneous inoculation with FPV/cIFN ($10^3$ pfu/chick). Chick mortality was recorded 2 weeks post vaccination. Chicks vaccinated with NDV B1 alone or with NDV B1 plus FPV wild-type virus showed 20–30% mortality compared to chickens co-vaccinated with NDV-B1 and FPV/cIFN, in which group, all chicks remained alive. Subsequently, all chicks were challenged at 4 weeks post vaccination with a pathogenic strain of NDV (GB-TX). All chicks were protected, except for those in the "no treatment" control group. These data show that NDV B1 vaccine induced mortality was reduced without affecting the vaccine's protective ability.

TABLE 4

Effect of recombinant FPV/cIFN virus on NVD B1 vaccine induced chick mortality and NDV B1 induced protection from NDV challenge

| Treatment | Vaccine induced mortality.[a] Dead/Total | Challenge induced mortality.[b,c] Dead/Total | Post vaccination anti-NDV antibody responses. 2 weeks[d] | 4 weeks |
|---|---|---|---|---|
| No treatment | 0/25 | 15/15 | <1 | <1 |
| NDVB1 alone | 7/30 | 0/12 | 1.87 (0.31) | 2.15 (0.32) |
| NDVB1 + FPV | 9/30 | 0/10 | 1.96 (0.54) | 1.99 (0.35) |
| NDVB1 + FPV/cIFN | 0/30 | 0/19 | 2.00 (0.42) | 2.15 (0.37) |

[a]Mortality was measured 2 weeks post vaccination.
[b]Chicks were challenged 4 weeks post vaccination, intramuscularly, with 10,000 ELD$_{50}$NDV GB-TX.
[c]Mortality was measured 2 weeks post challenge
[d]Antibody titers were determined by NDV virus neutralization and expressed as group mean ($\log_{10}$).

17-day-old chicken embryos were inoculated with 500 pfu/embryo with FPV/cIFN/NDV virus, FPV wild-type virus or PBS diluent (0.2 ml). Chicks were allowed to hatch and then placed in an isolation unit and observed for mortality for one week. These data show that inoculation of chicken embryos with FPV/cIFN+NDV or FPV wild-type does not interfere with normal hatching.

TABLE 5

Effect of FPV/cIFN/NDV virus in ovo

| Treatment | Number of Eggs Hatched/Total | Mortality (Dead/Total)[a] |
|---|---|---|
| Diluent (PBS) | 15/17 | 1/15 |
| FPV (wild-type) | 15/17 | 3/15 |
| FPV/cIFN/NDV | 14/18 | 0/14 |

[a]1 week post hatch

Three week old SPF chicks were vaccinated, subcutaneously, with 500 pfu/chick of FPV/cIFN/NDV recombinant virus. Sera were collected 9 days and 28 days post vaccination to measure neutralizing antibody responses raised against NDV. All chickens were challenged 28 days post vaccination with a pathogenic strain of NDV and observed for NDV induced mortality for 15 days. These data show that vaccinated chicks developed detectable anti-NDV antibody responses as little as 9 days post vaccination with FPV/NDV/cIFN recombinant virus. These antibody levels were maintained for at least 28 days. In addition, chickens vaccinated with FPV/cIFN/NDV recombinant virus were all protected against challenge with a virulent strain of NDV.

TABLE 6

Protective efficacy of FPV/cIFN/NDV vaccine in 3-week-old-chickens

| Vaccine | Post Challenge Mortality[a] Dead/Total | Post Vaccination Antibody Responses 9 days | 28 days |
|---|---|---|---|
| None | 19/19 | <1[b] | <1[c] |
| FPV-IFN-NDV | 0/20 | 1.36 (0.12) | 1.33 (0.31) |

[a]Chicks were challenged intramuscularly, 28 days post vaccination, with 10,000 ELD$_{50}$NDV GB-TX.
[b]Antibody responses were determined by VN test and expressed as geometric mean titer (log10) of 5 chickens
[c]Antibody responses were determined by VN test and expressed as geometric mean titer (log10) of 10 chickens One day old SPF chicks were vaccinated, subcutaneously, with 500 pfu/chick of FPV/cIFN/NDV recombinant virus.

Chicks were challenged intranasally/intraocularly at 4, 7 and 15 days post vaccination with virulent NDV (GB-TX), and observed for NDV induced mortality for 15 days in each case. These data show that vaccinated chicks are resistant to virulent NDV when challenged at 7 days post vaccination, but not as early as 4 days post vaccination. Thus, onset of immunity to NDV following vaccination with FPV/cIFN/NDV recombinant virus occurs between 4 and 7 days post vaccination.

TABLE 6

Protective efficacy of FPV/cIFN/NDV vaccine in one day old chicks

| Experiment No. | Vaccine | Mortality following challenge at 4, 7, and 15 days post vaccination. | | |
|---|---|---|---|---|
| | | 4-days Dead/Total | 7-days Dead/Total | 15-days Dead/Total |
| 1 | None | ND[a] | 10/10 | 10/10 |
| | FPV-IFN-NDV | ND | 0/10 | 0/10 |
| 2 | None | 10/10 | 10/10 | 10/10 |
| | FPV-IFN-NDV | 10/10 | 1/10 | 0/10 |
| | NDV-B1 | 4/10 | 0/10 | 0/10 |

[a]Not Done

Conclusions

1. Recombinant fowlpox viruses express biologically active chicken interferon into the supernatants of infected cells, as measured by protection of CEF cells from VSV infection.
2. Chicken interferon expressed in supernatants from recombinant SPV/cIFN infected cells has been shown to protect CEF cells against infection with HVT in a dose dependent manner.
3. Chicken interferon expressed from SPV/cIFN acted synergistically with LPS to activate chicken macrophages as detected by nitric oxide induction.
4. Recombinant FPV/cIFN virus was found to be safe in 10 day old chicks at a dosage of $6 \times 10^4$ pfu/chick.
5. Recombinant FPV/cIFN virus was shown to reduce NDV B1 vaccine induced mortality without affecting the vaccine's ability to protect chicks against NDV infection.
6. Inoculation of recombinant FPV/cIFN/NDV virus in ovo does not appear to interfere with normal hatching.
7. Recombinant FPV/cIFN/NDV virus was shown to induce anti-NDV neutralizing antibody in 3-week-old chicks as early as 9 days post vaccination with sustained immunity thru 28 days post vaccination. Furthermore, three-week-old chicks were fully protected against virulent NDV challenge at 28 days post vaccination.
8. Recombinant FPV/cIFN/NDV virus was shown to protect one-day-old chicks from virulent NDV challenge as early as 7 days post vaccination.
9. The foregoing data indicate that recombinant fowlpox viruses expressing chicken IFN may have beneficial applications as immune modulating agents in vitro, in vivo and in ovo.

References

1. C. Bertholet, et al., *EMBO Journal* 5, 1951–1957, 1986.
2. B. H. Coupar, et al., *Virology* 179, 159–167, 1990.
3. A. J. Davidson and B. Moss, *J. Mol. Biol.* 210, 749–769.
4. A. J. Davidson and B. Moss, *J. Mol. Biol.*, 210, 771–784.
5. P. L. Earl, et al., *Journal of Virology* 64, 2448–2451, 1990.
6. J. Esposito, et al., *Virology* 165, 313.
7. F. A. Ferrari, et al., *Journal of Bacteriology* 161, 55–562, 1985.
8. U. Gubler and B. J. Hoffman, *Gene* 25, 263–269.
9. D. Hanahan, *Molecular Biology* 166, 557–580, 1983.
10. M. A. Innis, et al., *PCR Protocols A Guide to Methods and Applications*, 84–91, Academic Press, Inc., San Diego 1990.
11. Maniatis, et al., *Molecular Cloning*, Cold Spring Harbor Laboratory, New York 1982.
12. L. J. N. Ross, et al., *Journal of General Virology*, 70, 1789–1804 (1989).
13. L. J. N. Ross, et al., *Journal of General Virology*, 72, 949–954 (1991).
14. J. Sambrook, et al., *Molecular Cloning A Laboratory Manual Second Edition*, Cold Spring Harbor Press, 1989.
15. J. Taylor, et al., *Vaccine* 9, 190–193, 1991.
16. A. Leutz, et al., *EMBO Journal* 8: 175–182 (1989).
17. M. J. Sekellick, et al., Journal of Interferon Reserch 14: 71–79 (1994).

What is claimed is:

1. A recombinant fowlpox virus comprising a foreign DNA inserted into a fowlpox virus genome, wherein the foreign DNA is inserted within a region of the genome which corresponds to a 3.5 kb EcoRI fragment within a SalI C fragment and PstI F fragment of the fowlpox virus genome and is capable of being expressed in a host cell into which the virus is introduced.

2. The recombinant fowlpox virus of claim 1, wherein the foreign DNA is inserted within a HpaI site within the region of the genome which corresponds to the 3.5 kb EcoRI fragment.

3. The recombinant fowlpox virus of claim 1, wherein the foreign DNA sequence encodes a polypeptide.

4. The recombinant fowlpox virus of claim 3, wherein the polypeptide is antigenic.

5. The recombinant fowlpox virus of claim 3, further comprising a foreign DNA sequence which encodes a detectable marker.

6. The recombinant fowlpox virus of claim 5, wherein the detectable marker is *E. coli* beta-galactosidase.

7. The recombinant fowlpox virus of claim 5, wherein the detectable marker is *E. coli* beta-glucuronidase.

8. The recombinant fowlpox virus of claim 1, wherein the foreign DNA sequence encodes a cytokine.

9. The recombinant fowlpox virus of claim 8, wherein the cytokine is chicken myelomonocytic growth factor (cMGF) or chicken interferon (cIFN).

10. The recombinant fowlpox virus of claim 4, wherein the foreign DNA sequence encodes an antigenic polypeptide which is selected from the group consisting of: infectious laryngotracheitis virus glycoprotein B, infectious laryngotracheitis virus glycoprotein D, Marek's disease virus glycoprotein D, Marek's disease virus glycoprotein B, Newcastle disease virus hemagglutinin, Newcastle disease virus neuraminidase, and Newcastle disease virus fusion protein.

11. The recombinant fowlpox virus of claim 1, wherein the foreign DNA sequence is under control of an endogenous upstream poxvirus promoter.

12. The recombinant fowlpox virus of claim 1, wherein the foreign DNA sequence is under control of a heterologous upstream promoter.

13. The recombinant fowlpox virus of claim 12, wherein the promoter is a synthetic pox viral promoter.

14. The recombinant fowlpox virus of claim 1, designated S-FPV-082.

15. A vaccine for immunizing an animal which comprises an effective immunizing amount of the recombinant fowlpox virus of claim 1 and a suitable carrier.

16. A method of immunizing an animal against an animal pathogen which comprises administering to the animal an effective immunizing dose of the vaccine of claim 15.

17. A method of enhancing an avian immune response which comprises administering to an avian an effective dose of the recombinant fowlpox virus of claim 1 and a suitable carrier.

18. The recombinant fowlpox virus of claim 3, wherein the synthetic pox viral promoter is selected from the group consisting of: pox synthetic late promoter 1, pox synthetic late promoter 2 early promoter 2, pox synthetic early promoter 1 late promoter 2, and pox synthetic early promoter 1.

19. A recombinant fowlpox virus designated S-FPV-085.

20. A recombinant fowlpox virus designated S-FPV-097, ATCC Accession No. VR 2446.

21. A recombinant fowlpox virus designated S-FPV-101.

22. A vaccine which comprises an effective immunizing amount of the recombinant fowlpox virus of any of claims 14, 19, 20, or 24 and a suitable carrier.

23. The vaccine of claim 22, wherein the carrier is a physiologically balanced culture medium containing stabilizing agents.

24. The vaccine of claim 22, wherein the effective immunizing amount is about $10^2$ to about $10^9$ PFU/dose.

25. The vaccine of claim 22, wherein the effective immunizing amount is about $10^3$ to about $10^5$ PFU/dose.

26. A method of immunizing an animal against fowlpox virus and Newcastle disease virus which comprises administering to the animal an effective immunizing dose of the vaccine of claim 22.

27. The method of claim 26, wherein the animal is an avian.

28. The method of claim 27, wherein the avian is a chicken.

29. The method of claim 26, wherein the vaccine is administered intramuscularly, intraperitoneally, intravenously, intradermal, intranasally, orally, ocularly, or inovo.

* * * * *